(12) United States Patent
Killard et al.

(10) Patent No.: US 9,347,931 B2
(45) Date of Patent: May 24, 2016

(54) LATERAL FLOW ASSAY DEVICE FOR COAGULATION MONITORING AND METHOD THEREOF

(75) Inventors: Anthony Joseph Killard, Wiltshire (GB); Magdalena Maria Dudek, Podkarpackie (PL); Brian MacCraith, Portmarnock (IE); Ib Mendel-Hartvig, Uppsala (SE); Ove Öhman, Uppsala (SE)

(73) Assignees: DUBLIN CITY UNIVERSITY, Dublin (IE); ÅMIC AB, Uppsala (SE)

( * ) Notice: Subject to any disclaimer, the term of this patent is extended or adjusted under 35 U.S.C. 154(b) by 161 days.

(21) Appl. No.: 13/265,813

(22) PCT Filed: Apr. 23, 2010

(86) PCT No.: PCT/EP2010/055470
§ 371 (c)(1),
(2), (4) Date: Jan. 13, 2012

(87) PCT Pub. No.: WO2010/122158
PCT Pub. Date: Oct. 28, 2010

(65) Prior Publication Data
US 2012/0107851 A1 May 3, 2012

(30) Foreign Application Priority Data
Apr. 23, 2009 (GB) .................................. 0906967.5
Nov. 26, 2009 (IE) .................................... 2009/0896

(51) Int. Cl.
*G01N 33/00* (2006.01)
*G01N 33/49* (2006.01)
(Continued)

(52) U.S. Cl.
CPC ...... *G01N 33/4905* (2013.01); *B01L 3/502753* (2013.01); *G01N 33/545* (2013.01);
(Continued)

(58) Field of Classification Search
CPC ... G01N 33/86; G01N 33/4905; G01N 11/14; G01N 11/105
USPC ............ 422/69, 73, 502, 503, 507, 527, 534, 422/535, 551
See application file for complete search history.

(56) References Cited

U.S. PATENT DOCUMENTS

| 4,094,647 A | 6/1978 | Deutsch et al. |
| 4,632,901 A | 12/1986 | Valkirs et al. |

(Continued)

FOREIGN PATENT DOCUMENTS

| WO | WO 92/01065 | 1/1992 |
| WO | WO 03/103835 | 12/2003 |

(Continued)

OTHER PUBLICATIONS

Adams, A.C., Alexander, F.B., Capio, C.D., Smith, T.E. (1981). Characterization of Plasma-Deposited Silicon Dioxide, *Journal of the Electrochemical Society*, 128 (7): 1545.

(Continued)

*Primary Examiner* — Jill Warden
*Assistant Examiner* — Brittany Fisher
(74) *Attorney, Agent, or Firm* — Knobbe Martens Olson & Bear, LLP

(57) ABSTRACT

The present invention is directed to a lateral flow assay device for the monitoring and measuring of coagulation and method thereof. Ideally, the invention is directed to a lateral capillary flow device for the monitoring and/or measurement of coagulation in a liquid sample wherein the device comprises a non-porous substrate with a zone for receiving a sample and a defined flow path zone wherein a clotting agent is deposited on at least part of the defined flow path zone to accelerate the coagulation of the liquid sample, enable the formation of an evenly distributed clot along the defined flow path zone and to result in the change in flow rate or cessation of flow of the liquid sample along the defined flow path zone.

21 Claims, 34 Drawing Sheets

(51) Int. Cl.
G01N 33/543 (2006.01)
G01N 33/545 (2006.01)
G01N 33/558 (2006.01)
G01N 33/86 (2006.01)
B01L 3/00 (2006.01)

(52) U.S. Cl.
CPC ........ *G01N33/54353* (2013.01); *G01N 33/558* (2013.01); *G01N 33/86* (2013.01); *B01L 3/502707* (2013.01); *B01L 2300/161* (2013.01); *B01L 2400/0406* (2013.01); *B01L 2400/086* (2013.01)

(56) References Cited

U.S. PATENT DOCUMENTS

| | | | |
|---|---|---|---|
| 4,756,884 | A | 7/1988 | Hillman et al. |
| 4,861,711 | A | 8/1989 | Friesen et al. |
| 4,943,522 | A | 7/1990 | Eisinger et al. |
| 5,039,617 | A | 8/1991 | McDonald et al. |
| 5,110,727 | A | 5/1992 | Oberhardt |
| 5,372,946 | A | 12/1994 | Cusak et al. |
| 5,601,995 | A | 2/1997 | Exner |
| 5,656,448 | A | 8/1997 | Kang et al. |
| 6,156,273 | A * | 12/2000 | Regnier et al. .................. 422/70 |
| 6,451,264 | B1 * | 9/2002 | Bhullar et al. ................. 422/507 |
| 2002/0119486 | A1 | 8/2002 | Oberhardt |
| 2002/0187071 | A1 | 12/2002 | Law |
| 2004/0072357 | A1 | 4/2004 | Stiene et al. |
| 2006/0239859 | A1 * | 10/2006 | Ohman et al. ................. 422/100 |
| 2008/0176272 | A1 * | 7/2008 | Bergman et al. ................. 435/29 |
| 2010/0248394 | A1 * | 9/2010 | Ohman et al. ................. 436/518 |

FOREIGN PATENT DOCUMENTS

| WO | WO 2005/089082 | 9/2005 |
|---|---|---|
| WO | WO 2006/137785 | 12/2006 |

OTHER PUBLICATIONS

Bellel, A., Sahli, S., Ziari, Z., Raynaud, P., Segui, Y., Escaich, D. (2006). Wettability of polypropylene films coated with SiOx plasma deposited layers, *Surface & Coatings Technology*, 201 (1-2): 129.
Bhattacharyya, A., Klapperich, C.M. (2006). Thermoplastic microfluidic device for on-chip purification of nucleic acids for disposable diagnostics, *Analytical Chemistry*, 78 (3): 788.
Bhurke, A.S., Askeland, P.A., Drzal, L.T. (2007). Surface modification of polycarbonate by ultraviolet radiation and ozone, *Journal of Adhesion*, 83 (1-3): 43.
Bieder, A., Gruniger, A., von Rohr, P.R. (2005). Deposition of SiOx diffusion barriers on flexible packaging materials by PECVD, *Surface & Coatings Technology*, 200 (1-4): 928.
Chan, C.M., Ko, T.M., Hiraoka, H. (1996). Polymer surface modification by plasmas and photons, *Surface Science Reports*, 24 (1-2): 3.
Chen, K.S., Lin, H.R., Chen, S.C., Tsai, J.C., Ku, Y.A. (2006). Long term water adsorption ratio improvement of polypropylene fabric by plasma pre-treatment and graft polymerization, *Polymer Journal*, 38 (9): 905.
Favia, P., d'Agostino, R. (1998). Plasma treatments and plasma deposition of polymers for biomedical applications, *Surface & Coatings Technology*, 98 (1-3): 1102.
Granier, A., Nicolazo, F., Vallee, C., Goullet, A., Turban, G., Grolleau, B. (1997). Diagnostics in O-2 helicon plasmas for SiO2 deposition, *Plasma Sources Science & Technology*, 6 (2): 147.
Greenwood, O.D., Hopkins, J., Badyal, J.P.S. (1997). Non-isothermal O-2 plasma treatment of phenyl-containing polymers, *Macromolecules*, 30 (4): 1091.
Inagaki, N., Tasaka, S., Nakajima, T. (2000). Preparation of oxygen gas barrier polypropylene films by deposition of SiOx films plasma-polymerized from mixture of tetramethoxysilane and oxygen, *Journal of Applied Polymer Science*, 78 (13): 2389.
International Search Report and Written Opinion for PCT/EP2010/055470 dated Sep. 14, 2010.
Johansson, B.L., Larsson, A., Ocklind, A., Ohrlund, A. (2002). Characterization of air plasma-treated polymer surfaces by ESCA and contact angle measurements for optimization of surface stability and cell growth, *Journal of Applied Polymer Science*, 86 (10): 2618.
Kitayama, D., Nagasawa, H., Kitajima, H., Okamoto, Y., Ikoma, H. (1995). Helicon-Wave-Excited Plasma Treatment of $SiO_x$ Films Evaporated on Si Substrate, *Japanese Journal of Applied Physics Part 1—Regular Papers Short Notes & Review Papers*, 34 (9A): 4747).
Kohler, L., Scaglione, S., Flori, D., Riga, J., Caudano, R. (2001). Ability of a gridless ion source to functionalize polypropylene surfaces by low-energy (60-100 eV) nitrogen ion bombardment. Effects of ageing in air and in water, *Nuclear Instruments & Methods in Physics Research Section B—Beam Interactions with Materials and Atoms*, 185 267.
Leterrier, Y. (2003). Durability of nanosized oxygen-barrier coatings on polymers—Internal stresses, *Progress in Materials Science*, 48 (1): 1.
Loh, F.C., Tan, K.L., Kang, E.T., Neoh, K.G., Pun, M.Y. (1995). Near-UV Radiation-Induced Surface Graft Copolymerization of Some O-3-pretreated Conventional Polymer Films, *European Polymer Journal*, 31 (5): 481.
Martinez-Garcia, A., Sanchez-Reche, A., Gisbert-Soler, S., Cepeda-Jimenez, C.M., Torregrosa-Macia, R., Martin-Martinez, J.M. (2003). Treatment of EVA with corona discharge to improve its adhesion to polychloroprene adhesive, *Journal of Adhesion Science and Technology*, 17 (1): 47.
Giroult-Matlakowski, G., Charles, C., Durandet, A., Boswell, R.W., Armand, S., Persing, H.M., Perry, A.J., Lloyd, P.D., Hyde, S.R., Bogsanyi, D. (1994). Deposition of Silicon Dioxide Films Using the Helicon Diffusion Reactor for Integrated Optics Applications, *Journal of Vacuum Science & Technology a—Vacuum Surfaces and Films*, 12 (5): 2754.
Nakao, A., Kaibara, M., Iwaki, M., Suzuki, Y., Kusakabe, M. (1996). *Applied Surface Science*, 101 112.
Pappas, D., Bujanda, A., Demaree, J.D., Hirvonen, J.K., Kosik, W., Jensen, R., McKnight, S. (2006). Surface modification of polyamide fibers and films using atmospheric plasmas, *Surface & Coatings Technology*, 201 (7): 4384.
Strobel, M., Lyons, C.S. (2003). The role of low-molecular-weight oxidized materials in the adhesion properties of corona-treated polypropylene film, *Journal of Adhesion Science and Technology*, 17 (1): 15.
Suh, H., Hwang, Y.S., Lee, J.E., Han, C.D., Park, J.C. (2001). Behavior of osteoblasts on a type I atelocollagen grafted ozone oxidized poly L-lactic acid membrane, *Biomaterials*, 22 (3): 219.
Suzer, S., Argun, A., Vatansever, O., Aral, O. (1999). XPS and water contact angle measurements on aged and corona-treated PP, *Journal of Applied Polymer Science*, 74 (7): 1846.
Yamazaki, M. (2004). Industrialization and application development of cyclo-olefin polymer, *Journal of Molecular Catalysis a—Chemical*, 213 (1): 81.
Dudek et al., Evaluation of a Range of Surface Modifications for the Enhancement of Lateral Flow Assays on Cyclic Polyolefin Micropillar Devices, Plasma Process and Polymers, 2009, 6:620-630.

* cited by examiner 2.5 mg/mL 1.25 mg/mL

Plain COP surface

SiOx coating

PE treatment

LATERAL FLOW ASSAY DEVICE FOR COAGULATION MONITORING AND METHOD THEREOF

This application is the U.S. National Phase under 35 U.S.C. §371 of International Application No. PCT/EP2010/055470, filed Apr. 23, 2010, which claims priority to Great British Patent Application No. 0906967.5, filed Apr. 23, 2009 and also to Irish Patent Application No. 2009/0896, filed Nov. 26, 2009.

FIELD OF THE INVENTION

The present invention is directed to a lateral flow assay device for the monitoring and measuring of coagulation and method thereof.

BACKGROUND OF THE INVENTION

Many different types of lateral flow or capillary flow assays and devices are presently on the market. Strip-based tests are, for example, ideal for rapid home and point-of-care testing as well as for detection of various environmental analytes. Lateral flow devices have been widely used as the lateral movement of the test fluid allows its controlled interaction with various reagents which can be located along the test channel allowing control of sequencing and timing of reagent interactions. The most common lateral flow tests available on the market are pregnancy, Chlamydia, Strep throat and HIV tests and tests for routinely screening foods for pathogens (i.e. DuPone™). There are many other applications of lateral flow technology such as those covered in U.S. Pat. Nos. 4,861,711, 4,632,901, 5,656,448, 4,943,522 and U.S. Pat. No. 4,094,647 to name a few.

In lateral flow devices which employ passive means of fluid movement (that is not aided by a fluid pump) fluid movement is induced by capillary forces. These forces originate at the interface between the solid and liquid and can arise in narrow capillaries with smooth surfaces or over a wider cross-sectional area due to the presence of structures which can induce such capillary forces. Typically, such conventional lateral flow assays use lateral flow materials such as nitrocellulose and filter papers which have highly porous structures which induces capillary forces as shown in for example, U.S. Pat. No. 5,601,995. However, such materials have disadvantages in terms of a significant lack of precision largely due to the inherent variability in the production of the nitrocellulose, which leads to further problems in the precise control of movement of liquid samples along the device. Thus, there is a need to provide variations and improvements to such conventional lateral flow assay technology.

For example, many know lateral flow assay devices utilize capillary tubes or channels to direct flow. In US 2002/0187071 and U.S. Pat. No. 5,039,617 (both coagulation assays) for example, the clotting agent is mixed with the sample liquid in a reaction chamber which is separate to the flow path. This is quite a conventional setup and other conventional assays are outlined below. However, it presents various problems where for example the clot can separate from the serum. This separation reduces the effectiveness of the assay to halt or retard fluid flow. As a result, such known capillary tube devices often require long and tortuous flow paths to bring about such retardation of the flow.

Furthermore, these capillary channel-based devices generally have poor surface area to volume ratios which reduce sample contact with the walls of the capillary and exacerbate this problem.

Additionally, the deposition of various reagents on the surface of such capillary tubes is less effective in being dissolved and redistributed by the sample for homogeneous activation of the coagulation response with a resulting inhomogeneity of the clot formation through the sample.

Thus, such know capillary-tube based lateral flow assay devices can present problems during use.

Other problems encountered relate to the materials used for making the lateral flow assay devices. Cyclic polyolefins have been recently used in the manufacture of some lateral flow assay devices. Other materials can be successfully employed in lateral flow test systems including, polystyrene, polyethylene terephthalate (polyester) (PET), polymethylmethacrylate (PMMA), glass, glass fibers, ceramics etc.

Cyclic polyolefins (COP) are thermoplastic resins with an excellent combination of optical and electronic properties. In 1983, while working with norbornene polymer, cyclo-olefin polymers were synthesized from ring-opening polymerization. After hydrogenation of double bonds in the polymer, a glass-clear plastic was created. The high transparency, low specific gravity, low water absorbency, high heat resistance as well as low autofluorescence and high UV transmission of this material make it excellent for biomedical applications (Yamazaki, M. (2004). Industrialization and application development of cyclo-olefin polymer, *Journal of Molecular Catalysis a-Chemical,* 213 (1): 81; Bhattacharyya, A., Klapperich, C. M. (2006). Thermoplastic microfluidic device for on-chip purification of nucleic acids for disposable diagnostics, *Analytical Chemistry,* 78 (3): 788). Such materials can be further structured and micropatterned using a host of techniques such as injection moulding and hot embossing to give additional fluid control properties. Advantageously, this type of polymer is chemically inert, which minimizes non-specific biological interactions.

It is known that surface modification of such cyclic polyolefins may result in changing the polymeric material characteristics such as surface tension. Many kinds of surface modification methods aimed at surface wettability enhancement have been described previously. For example, several treatments are aimed at increasing surface tension, by the formation of new functional groups on the polymer surface (Chan, C. M., Ko, T. M., Hiraoka, H. (1996). Polymer surface modification by plasmas and photons, *Surface Science Reports,* 24 (1-2): 3; Nakao, A., Kaibara, M., Iwaki, M., Suzuki, Y., Kusakabe, M. (1996). Surface characterization of cell adhesion controlled polymer modified by ion bombardment, *Applied Surface Science,* 101 112). However, in many cases, such treatment methods induce damage to the surface, which reduces its excellent bulk properties. Moreover, the gained benefit of the surface wettability may decrease with time, due to contact with air or water (Suzer, S., Argun, A., Vatansever, O., Aral, O. (1999). XPS and water contact angle measurements on aged and corona-treated PP, *Journal of Applied Polymer Science,* 74 (7): 1846; Kohler, L., Scaglione, S., Flori, D., Riga, J., Caudano, R. (2001). Ability of a gridless ion source to functionalize polypropylene surfaces by low-energy (60-100 eV) nitrogen ion bombardment. Effects of ageing in air and in water, *Nuclear Instruments & Methods in Physics Research Section B-Beam Interactions with Materials and Atoms,* 185 267).

In view of these problems, it has been desirable to develop coatings which are water-stable, biocompatible and do not deteriorate over a long period of time. One surface modification technique is UV/ozone treatment. The ozone oxidation can produce peroxides and hydroperoxides with free radicals, and the following immobilization of functional molecules can be performed under thermal or initiator induction. UV exposure in ozone and air was found to impart a highly hydrophilic nature to normally hydrophobic polymeric surfaces (Bhurke, A. S., Askeland, P. A., Drzal, L. T. (2007). Surface modification of polycarbonate by ultraviolet radiation and ozone, *Journal of Adhesion*, 83 (1-3): 43; Ho, M. H., Lee, J. J., Fan, S. C., Wang, D. M., Hou, L. T., Hsieh, H. J., Lai, J. Y. (2007). Efficient modification on PLLA by ozone treatment for biomedical applications, Macromolecular *Bioscience*, 7 (4): 467; Suh, H., Hwang, Y. S., Lee, J. E., Han, C. D., Park, J. C. (2001). Behavior of osteoblasts on a type I atelocollagen grafted ozone oxidized poly L-lactic acid membrane, *Biomaterials*, 22 (3): 219). Flame and corona discharge are other techniques widely used in industry on account of their effectiveness (Martinez-Garcia, A., Sanchez-Reche, A., Gisbert-Soler, S., Cepeda-Jimenez, C. M., Torregrosa-Macia, R., Martin-Martinez, J. M. (2003). Treatment of EVA with corona discharge to improve its adhesion to polychloroprene adhesive, *Journal of Adhesion Science and Technology*, 17 (1): 47; Strobel, M., Lyons, C. S. (2003). The role of low-molecular-weight oxidized materials in the adhesion properties of corona-treated polypropylene film, *Journal of Adhesion Science and Technology*, 17 (1): 15). However, none of these techniques are without problems. Above all, they are expensive and the operator is exposed to hazardous conditions. Another well investigated solution to producing functional layers is the attachment of polymer particles by grafting or plasma polymerization (Chen, K. S., Lin, H. R., Chen, S. C., Tsai, J. C., Ku, Y. A. (2006). Long term water adsorption ratio improvement of polypropylene fabric by plasma pretreatment and graft polymerization, *Polymer Journal*, 38 (9): 905; Yasuda, H. Plasma Polymerization, Academic Press, New York, 1985, 344) which gives a stable, hydrophilic layer on the plastic surfaces. Graft polymers have been shown to penetrate or partially penetrate the substrate polymer resulting in a thin surface layer (Loh, F. C., Tan, K. L., Kang, E. T., Neoh, K. G., Pun, M. Y. (1995). Near-UV Radiation-Induced Surface Graft Copolymerization of Some O-3-pretreated Conventional Polymer Films, *European Polymer Journal*, 31 (5): 481; Johansson, B. L., Larsson, A., Ocklind, A., Ohrlund, A. (2002). Characterization of air plasma-treated polymer surfaces by ESCA and contact angle measurements for optimization of surface stability and cell growth, *Journal of Applied Polymer Science*, 86 (10): 2618). Several types of plasma treatments have been described (Pappas, D., Bujanda, A., Demaree, J. D., Hirvonen, J. K., Kosik, W., Jensen, R., McKnight, S. (2006). Surface modification of polyamide fibers and films using atmospheric plasmas, *Surface & Coatings Technology*, 201 (7): 4384; Morra, A., Occhiello, E., Garbassi, F. (1990). Wettability and Surface Chemistry of Irradiated PTFE, *Angewandte Makromolekulare Chemie*, 180 191; Greenwood, O. D., Hopkins, J., Badyal, J. P. S. (1997). Non-isothermal O-2 plasma treatment of phenyl-containing polymers, *Macromolecules*, 30 (4): 1091. Plasma treatments are known to form polymer radicals on the treated surfaces. However, it has been proven that modification with oxygen plasma alone is not stable over time. This results in the degradation of functional groups created in this process.

For coatings of blood-contacting materials, for example, "silicon-like" films have been widely used. Organic monomer vapours containing silicon alone or in a mixture of other gases, such as $O_2$ are used to create such films (Favia, P., d'Agostino, R. (1998). Plasma treatments and plasma deposition of polymers for biomedical applications, *Surface & Coatings Technology*, 98 (1-3): 1102). $SiO_x$ thin films deposited by PECVD offer several advantages in that they are not only colourless and transparent but are also insoluble, mechanically tough, chemically inert and thermally stable (Leterrier, Y. (2003). Durability of nanosized oxygen-barrier coatings on polymers—Internal stresses, *Progress in Materials Science*, 48 (1): 1). These characteristics have allowed $SiO_x$ films to find expanded application in biomaterials, microelectronics, food and the medical and pharmaceutical industries (Inagaki, N., Tasaka, S., Nakajima, T. (2000). Preparation of oxygen gas barrier polypropylene films by deposition of SiOx films plasma-polymerized from mixture of tetramethoxysilane and oxygen, *Journal of Applied Polymer Science*, 78 (13): 2389; Bellel, A., Sahli, S., Ziari, Z., Raynaud, P., Segui, Y., Escaich, D. (2006). Wettability of polypropylene films coated with SiOx plasma deposited layers, *Surface & Coatings Technology*, 201 (1-2): 129; Bieder, A., Gruniger, A., von Rohr, P. R. (2005). Deposition of SiOx diffusion barriers on flexible packaging materials by PECVD, *Surface & Coatings Technology*, 200 (1-4): 928). For PECVD deposition of $SiO_2$, the simplest and most commonly used mixtures of gases are $O_2/SiH_4$, $N_2O/SiH_4$. There are several papers reporting good quality $SiO_2$ film deposition in an $O_2/SiH_4$ helicon plasma for different applications (Giroult-matlakowski, G., Charles, C., Durandet, A., Boswell, R. W., Armand, S., Persing, H. M., Perry, A. J., Lloyd, RD., Hyde, S. R., Bogsanyi, D. (1994). Deposition of Silicon Dioxide Films Using the Helicon Diffusion Reactor for Integrated Optics Applications, *Journal of Vacuum Science & Technology a-Vacuum Surfaces and Films*, 12 (5): 2754; Kitayama, D., Nagasawa, H., Kitajima, H., Okamoto, Y., Ikoma, H. (1995). Helicon-Wave-Excited Plasma Treatment of $SiO_x$ Films Evaporated on Si Substrate, *Japanese Journal of Applied Physics Part 1-Regular Papers Short Notes & Review Papers*, 34 (9A): 4747). $SiH_4$ highly diluted in $O_2$ gas feed was widely used in early studies of $SiO_2$ plasma deposition Adams, A. C., Alexander, F. B., Capio, C. D., Smith, T. E. (1981). Characterization of Plasma-Deposited Silicon Dioxide, *Journal of the Electrochemical Society*, 128 (7): 1545. However, silane is an explosive gas at room temperature and so its use in an industrial environment requires severe safety regulations. Organosilicones, which are relatively inert liquids at room temperature may be preferable to silane (Granier, A., Nicolazo, F., Vallee, C., Goullet, A., Turban, G., Grolleau, B. (1997). Diagnostics in O-2 helicon plasmas for SiO2 deposition, *Plasma Sources Science & Technology*, 6 (2): 147.). Hexamethyldisiloxane (HMDSO), hexamethyldisilazane (HMDSN), and tetraethoxysilane (TEOS) take a lead as precursors in $SiO_2$ deposition.

Some improvements/modifications to these systems using materials other than nitrocellulose are outlined below. For example, the controlled formation of other microstructures for inducing capillary forces via surface patterning techniques can result in the same capillary force effects, but reduce the inherent variability of materials such as nitrocellulose. For instance, the introduction of periodic structures which protrude from the surface such as micropillars via a range of fabrication techniques (hot embossing, injection moulding, micromachining etc) would induce controlled and reproducible capillary forces. Such defined surface structures can be readily implemented through the fabrication of polymeric plastics such as thermoplastics which are liquid at high temperature and solidify at some lower temperature.

One example of an improved lateral flow assay is a device produced by Amic BV, the 4-cast 'chip' as show in FIG. 1. This device is based on a low cost, mass producible, polymer platform fabricated from a range of materials, including cyclic polyolefins, and structured at a micrometer scale using a range of techniques including hot embossing or injection moulding, to form arrays of closely spaced micropillars. This device has been shown to have superior properties over other conventional lateral flow materials utilising, for example, nitrocellulose. Due to the defined, uniform structure of micropillars on the device, fluid flow can be precisely and reproducibly controlled in the device by selecting the size of, and the distance between the micropillars. Thus, fluid is drawn by capillary action through the device. WO 2003/103835, WO 2005/089082 and WO 2006/137785, in the name of AMIC AB, are directed to one such assay method and device. Such devices are used in many different types of assays such as immunoassays, protein microarrays and DNA microarrays. Examples of tests based on Åmic's 4-castchip technology include a fluorescently detected human cardiac Troponin I antigen, total IgG antibody in plasma and c-reactive protein (CRP).

It is known that the controlled movement of fluids is often a prerequisite of a whole host of biological assay devices, where it is often required to move a biological sample to a suitable location at which an assay can be performed, typically by combining the sample with other assay components and/or performing some analysis or measurement at the site. In some instances, the actual movement of the fluid along the assay device is a component of the measurement itself. This is particularly important in the area of blood coagulation monitoring.

The ability of the body to arrest the flow of blood following vascular injury is crucial. The process by which this occurs is termed haemostasis which involves blood coagulation leading to formation of a blood clot or thrombosis. Essentially, a blood clot consists of a plug of platelets in a network of insoluble fibrin particles. Whilst formation of the clot is essential, the persistence of such clots is undesirable and dangerous.

People who suffer from cardiac or vascular diseases and patients that have undergone surgical procedures are at risk of developing blood clots that may result in life-threatening clinical conditions. Such people are often treated with blood-thinning or anticoagulant drugs. However, the amount of anticoagulant in the bloodstream must be maintained at the proper level. Too little may result in unwanted clotting whilst too much can result in haemorrhaging. As a result routine coagulation screening tests have been developed in order to evaluate the coagulation status of blood or plasma. In some instances of blood coagulation monitoring, the measurement of a blood clot is determined by how the blood sample moves in a device during the clotting process. Typically, the clotting cascade is induced by the addition of suitable biochemical reagents and as the blood clots, its resistance to movement is greatly enhanced which can be detected in a range of ways. Some examples of known coagulation assay method and devices are given below.

U.S. Pat. No. 5,372,946 is directed to an apparatus and method for performing a coagulation time test on a sample of blood wherein the blood is deposited in a fluid reservoir and disposable cuvette. In use a blood sample is drawn into a capillary channel by a pumping action and is drawn back and forth through a very narrow aperture. When the clot forms, this movement through the aperture ceases and clotting can be said to have occurred. The testing machine measures the time required each time the blood is caused to traverse the restricted region. However, mechanical assistance in the form of pumping is used in this device and this is undesirable as it adds to the complexity and cost of the device.

U.S. Pat. No. 5,601,995 is directed to an apparatus and method for detecting coagulation in blood samples. In use the test blood sample is allowed to travel through a porous membrane material (nitrocellulose) and the distance it travelled is dependent on the rate of clot formation. This is a standard lateral flow assay conventionally used to monitor coagulation.

U.S. Patent Application Number 2004/0072357, is directed to a device and method for measuring the clotting times in a fluid, typically blood, within a microchannel whereby the onset of clotting is determined by measurement of the rate of change or value of capacitance or impedance between two electrodes situated on either side of the microchannel. In use, the sample is drawn into a polymer microchannel and the distance travelled down the channel before clotting was given as a means of determining the clotting time. However, devices such as US Patent Application No. 2004/0072357, which use open capillary-based systems and employing passive fluid movement suffer from extremely slow filling times which increases the length of time required for the assay. They also have poor surface area to volume characteristics and so have associated problems of mixing reagent with sample in the central lumen of the channel which reduces device efficiency.

Thus, as outlined above one of the major problems with know lateral flow assay devices is to be able to precisely control the movement of liquid samples along such devices. Despite many different solutions proposed there is still a need to improve on conventional lateral flow assay technology, particular in the field of blood coagulation assays. Hence, the present invention is directed to an improved coagulation assay device and method thereof.

SUMMARY OF THE INVENTION

The invention provides improved method and devices for performing coagulation type assays.

According to a first general aspect of the invention, there is provided a lateral capillary flow device for the monitoring and/or measurement of coagulation in a liquid sample wherein the device is an open lateral flow device which comprises a non-porous substrate with a zone for receiving a sample and a defined flow path zone wherein a clotting agent, ideally fibrinogen or thrombin or a derivative thereof, is deposited on at least part of the defined flow path zone.

It will be understood that the defined flow path zone has been modified to reproducibly accelerate the coagulation of the liquid sample, form a more evenly distributed clot throughout the entire sample and to ensure the controlled change in flow rate and/or cessation of flow of the liquid sample along the defined flow path zone. In this manner the device induces capillary action in the liquid sample along the defined flow path.

According to a second general aspect of the invention, there is provided a lateral capillary flow assay device for use in the monitoring and/or measurement of coagulation in a liquid sample wherein the device is an open lateral flow device which comprises a non-porous substrate with a zone for receiving a sample and a defined flow path zone wherein the surface of the substrate has been modified to accelerate the coagulation of the liquid sample, preferably by depositing a coating of SiOx on the surface of the substrate and/or surface modification with a polyelectrolyte.

It will be understood that the surface of the substrate has been modified to increase surface activity and hydrophilicity to facilitate improved liquid fluid flow through the device.

Ideally, blood coagulation is monitored and/or measured.

According to a further aspect of the invention, there is provided a method for the monitoring and/or measurement of coagulation in a liquid sample using a lateral capillary flow devices of the invention wherein the sample is added to the receiving zone on the substrate and is transported through capillary action from the receiving zone through a flow path such that lateral capillary flow of said liquid sample is achieved.

According to a still further aspect of the invention, there is provided a method for modifying the surface of a lateral capillary flow device wherein the device comprises a non-porous substrate with a zone for receiving a sample and a defined flow path zone wherein the surface of the substrate has been modified to accelerate the coagulation of the liquid sample wherein the method comprises pre-treating the substrate with oxygen plasma and argon; and subjecting the substrate to $SiO_x$ deposition using plasma enhanced chemical vapour deposition (PEVCD).

According to a still further aspect of the invention, there is provided an assay kit comprising a lateral capillary flow device of the invention along with the necessary reagents for carrying out the assay.

According to a still further aspect of the invention, there is provided an analytical or diagnostic test device comprising a lateral capillary flow device of the invention.

DETAILED DESCRIPTION OF THE INVENTION

In the following description the term "lateral flow assay device" and "capillary flow assay device" are understood to be interchangeable.

The term "sample" used herein means a volume of a liquid, solution or suspension, intended to be subjected to qualitative or quantitative determination of any of its properties, such as the presence or absence of a component, the concentration of a component, etc. The sample may be a sample taken from an organism, such as a mammal, preferably a human; or from the biosphere, such as a water sample, or an effluent; or from an technical, chemical or biological process, such as a process of manufacturing, e.g. the production of medicaments, food, feed, or the purification of drinking water or the treatment of waste effluents. The sample may be subjected to qualitative or quantitative determination as such, or after suitable pre-treatment, such as homogenization, sonication, filtering, sedimentation, centrifugation, heat-treatment etc.

Typical samples in the context of the present invention are body fluids such as blood, plasma, serum, lymph, urine, saliva, semen, amniotic fluid, gastric fluid, phlegm, sputum, mucus, tears etc.; environmental fluids such as surface water, ground water, sludge etc.; and process fluids such as milk, whey, broth, nutrient solutions, cell culture medium, etc. The embodiments of the present invention are applicable to all samples, but preferably to samples of body fluids, and most preferably to blood samples including whole blood samples.

The determination based on lateral flow of a sample and the interaction of components present in the sample with reagents present in the device and detection of such interaction, either qualitatively or quantitatively, may be for any purpose, such as diagnostic, environmental, quality control, regulatory, forensic or research purposes.

The term "analyte" is used as a synonym of the term "marker" and intended to encompass any substance that is measured quantitatively or qualitatively.

The terms "zone", "area" and "site" are used in the context of this description, examples and claims to define parts of the fluid passage on a substrate, either in prior art devices or in a device according to an embodiment of the invention.

The term "reaction" is used to define any reaction, which takes place between components of a sample and at least one reagent or reagents on or in said substrate, or between two or more components present in said sample. The term "reaction" is in particular used to define the reaction, taking place between an analyte and a reagent as part of the qualitative or quantitative determination of said analyte.

The term "substrate" here means the carrier or matrix to which a sample is added, and on or in which the determination is performed, or where the reaction between analyte and reagent takes place.

In the following description the terms "clotting" and "coagulation" are understood to be interchangeable. It will be understood that coagulation or clotting in liquid materials, including blood or other materials, may also be monitored and/or measured using the present invention. It will be understood that coagulation of any liquid sample effected via the coagulation cascade using fibrinogen or thrombin may be contemplated. Other liquids in which coagulation may be monitored and/or measured include proteinaceous solutions (e.g., milk), and other coagulating liquids such as flocculating waters and wastewaters.

In the following description the term "micropillar" or "micro-projections" or "protruding microstructures" cover a plurality of vertical projections or pillars protruding from the surface of the substrate which define the flow through the substrate. Ideally, such micropillars consist of areas of projections substantially vertical to said surface, and having a height (H), diameter (D) and reciprocal spacing (t1, t2) such, that lateral capillary flow of the liquid sample in said flow zone is achieved.

In the following description, it will be understood that the term "coating" is interchangeable with the term "layer" or "film".

The present invention provides an improved lateral flow assay method and device.

Ideally, blood coagulation is monitored and/or measured in the assay device and method of the invention.

According to a first general aspect of the invention, there is provided a lateral capillary flow device for the monitoring and/or measurement of coagulation in a liquid sample wherein the device is an open lateral flow device which comprises a non-porous substrate with a zone for receiving a sample and a defined flow path zone wherein the clotting agent fibrinogen or thrombin or a derivative thereof is deposited on at least part of the defined flow path zone.

In one embodiment, the clotting agent is deposited on the entire surface of the defined flow path zone.

Ideally, the lateral flow assay device is an open lateral flow device and not a capillary tube or channel type device. The essential aspect is that the device induces capillary action in the liquid sample along the defined flow path.

In this manner, the lateral capillary flow device of the invention is distinguished from known capillary flow tubes, capillaries or channel devices.

For example, such an open lateral flow device may comprises a structure that improves or increases the surface area to volume ratio between the sample and the device surface, while also maintaining ordered, controlled, adequate and predictable capillary forces. This may be achieved with an open lateral flow assay device with a planar surface with regularly spaced structures comprising protrusions or indentations along the substrate, preferably the flow path.

According to a preferred embodiment of the invention, the flow path zone of the substrate comprises a plurality of vertical projections or micropillars protruding from the surface of the substrate which define the flow along the substrate.

Optionally, the vertical projections consist of areas of projections substantially vertical to said surface, and having a height (H), diameter (D) and reciprocal spacing such, that lateral capillary flow of the liquid sample in the flow path zone is achieved.

We have found that depositing a layer of a clotting agent, preferably fibrinogen or thrombin or a derivative thereof, on the surface of the flow path of the substrate results in an improved lateral flow assay device which:

i) accelerates the coagulation of the liquid sample;
ii) forms a more evenly distributed clot throughout the entire blood sample; and
iii) ensures the controlled change in flow rate and/or cessation of flow of the liquid sample along the defined flow path zone.

The combination of this type of coating with the structural characteristics of the lateral flow device prevents the separation of clot from serum.

It will be understood that the formation of the distributed fibrin network can be facilitated in two ways. The first is to use deposited thrombin to activate fibrin formation from endogenous fibrinogen. The second is to use deposited exogenous fibrinogen which forms a distributed fibrin clot in response to thrombin formation resulting from activation of the coagulation cascade. We have found that the coating or layer of clotting agent significantly enhances the evenly distributed formation of the fibrin network when thrombin is generated in the clotting cascade. Hence, retardation of the fluid flow can be made more significant.

In the method of the invention, the coagulation assay involves measuring the flow rate and/or time to clot formation. Specifically, in order to carry out these assays and assess coagulation/clotting times, the conversion of the sample from liquid to gel (clot) state in time and/or distance travelled is measured. Thus, it is important to rapidly induce the formation of a uniform, reproducible clot and prevent the separation of the sample into a fibrin mesh and serum. The devices of the invention ensures this is achieved.

Specifically, this device overcomes the problems, such as separation of the clot from the serum, reduced effectiveness of the assay to halt or retard fluid flow, complex designs in terms of extended flow paths, inhomogeneity of the clot formation through the sample etc, associated with known lateral flow assays such as the capillary tube-based flow devices described in US 2002/0187071 and U.S. Pat. No. 5,039,617 and many others.

Advantageously, the lateral flow assay device of the present invention is an 'open' surface preferably with micropillars or other projections/indentations as defined above. The forces brought about by the presence of pillars or other projections/indentations as defined above provide the benefit of capillarity without the problems of capillary tube surface area/sample volume ratios expanded on above. This results in more effective interaction of deposited reagent with sample with improved rates of dissolution, homogeneity, etc.

The clotting agent may be applied to the modified substrate surface using several manual or/and automated techniques including, but not limiting to, pipetting, spray-coating, dip-coating, light-directed patterning, ink-jet printing, screen printing, lithographic techniques (i.e. microcontact printing), electrospray, chemical vapour deposition, atomic force microscope based molecule deposition and others.

The clotting agent is ideally fibrinogen, thrombin or a derivative thereof. However, other clotting factors and derivatives may also be contemplated. For example, the coagulation of milk or milk components via mechanical action, heat, bacteria, enzymes, alcohol or acidity via the action of casein (in the manufacture of butter, creams, cheese, yoghurt, or in other processes which result in the formation or transformation of biopolymers such as proteins, carbohydrates, nucleic acids, etc which also lead to changes in viscosity.

In this way the clotting agent is immobilized on the substrate surface. Stability of the clotting agents can be further enhanced with the incorporation of supporting reagents including, but not limited to, other proteins, polymers, sugars, surfactants, humectants. Further, stability can be improved by using appropriate drying techniques using techniques such as temperature control, humidity control, air flow and drying rates, e.g., lyophilisation. Further stability can be achieved by using various storage and packaging means such as controlled atmosphere for humidity, temperature, inert gases, vacuum, delivered through various techniques such as pouching and sealing and specified storage conditions.

It will be understood that the clotting agent may be present on the entire substrate surface, including the zone for receiving a sample and the defined flow path zone.

According to a preferred embodiment of the invention, the clotting agent is fibrinogen.

According to another embodiment of the invention, the clotting agent is thrombin. Ideally, from 5 to 10 U/ml of dried thrombin may be used. Optionally, the surfactant used may be a non-ionic surfactant (such as Triton X-100). In one embodiment approximately 10 µl of thrombin is used.

Other reagent materials may be deposited along with the clotting agent. Such additional reagent materials may be selected from, but not limited to one or more of the following: tissue factor; phospholipids; additional materials that can induce or/and accelerate coagulation including clotting factors other than thrombin or fibrinogen and/or procoagulants; micronized silica materials including glass fibres, ground glass and glass microparticles; and/or coagulation surface activators including kaolin, celite and/or ellagic acid.

Additionally, reagent formulations for specific coagulation assays such as TT, aPTT, ACT and PT reagents may be used. These are outlined in the Examples. For instance, ACT assays are typically performed with addition of contact activator alone (micronized silica, glass, kaolin, celite, ellagic acid, etc). Additionally, aPTT contains such contact activators with additional phospholipid mixtures, referred to as a partial thromboplastin. PT assays possess as their main active ingredient a tissue factor, also known as Factor III. Thrombin Time (TT) also called Thrombin Clotting Time (TCT) is activated by the addition of thrombin reagent. Calcium chloride may also be added in instances where blood samples have been taken into citrated test tubes to prevent coagulation prior to analysis.

The clotting agent may be deposited along with supporting reagent materials or a mixture of supporting reagent materials. These supporting reagent materials include poly (ethylene glycol) (PEG), sugars (i.e. dextran, maltodextrose) and surfactants such as non-ionic surfactants (i.e. polysorbate 20 or 80, Triton X-100). Such supporting reagents are added for a range of purposes such as to reduce non-specific interactions between the test sample and the substrate, obtain desired flow velocity, to control the stability, viscosity and release of the reagent materials.

According to a preferred embodiment of the invention, the supporting reagent material is a non-ionic surfactant. Surfactants are widely used for their ability to reduce surface tension at solution/surface interfaces and thus assist in the control of fluid movement. However, due to their amphiphilic nature, surfactants can disrupt many biological systems such as membranes and phospholipid structures. Such structures are extremely important in the coagulation process. Therefore, the type and concentration of surfactant employed is critical in achieving a balance between assisting and controlling fluid movement while not inhibiting coagulation. Ionic surfactants (for example sodium dodecyl sulphate (SDS) and cetyl trimethylammonium bromide (CTAB) are two well-known and exemplary anionic and cationic surfactants, respectively. However, such surfactants are unsuitable for use in coagulation assays due to their disruptive effects as discussed above.

Thus, the present invention ideally utilises non-ionic surfactants such as pluronics (e.g., Triton X-100 and polysorbates (e.g., Tween 20) which do not possess ionic head groups, but either highly branched or linear polar groups, mostly composed of subunits of ethoxy functional groups. These non-ionic surfactants are less disruptive to such structures. However, the highly branched polysorbates have proven more disruptive than the lesser branched pluronics which makes non-ionic surfactants of this class particularly suited for application in coagulation assays. Through the selection of an appropriate concentration, the use of non-ionic surfactants can effectively reduced interfacial surface tension, assist uniform, reproducible lateral flow and not interfere in the coagulation process.

The clotting agent, additional reagent material and/or supporting reagent material may be added to the test channel of the substrate surface in many different configurations. Such configurations include but are not limited to the following:

different materials may be deposited in several sectors of a single substrate surface. For example, the whole test channel or only the initial stages may be patterned, divided into sectors (where necessary reagent materials would be deposited and dried). The different sectors may be separated from each other with a layer of a tape (e.g. one-side sticky pressure sensitive adhesive, PSA etc) that would be removed once the drying process was over or by creating a highly hydrophobic sub-sectors to prevent the reagent materials mixing.

gradient deposition of a mixture of materials or gradient deposition from the start and end of the test channel.

layer deposition is also possible where the material is deposited and dried subsequently without a pre-mixing.

According to a second general aspect of the invention, there is provided a lateral capillary flow device for the monitoring and/or measurement of clotting in a liquid sample wherein the device is an open lateral flow device which comprises a non-porous substrate with a zone for receiving a sample and a defined flow path zone wherein the surface of the substrate has been modified to accelerate the coagulation of the liquid sample by depositing a coating of $SiO_x$ on the surface of the substrate.

Optionally, the surface of the substrate may be modified with a polyelectrolyte in combination with the SiOx coating or alone.

Ideally, the surface of the substrate is modified as above to increase surface activity and hydrophilicity to facilitate improved liquid fluid flow through the device.

Ideally, only the surface of the substrate in contact with the liquid sample is modified.

It will be understood that the device of both the first and second aspect of the invention may comprise a flow path zone of the substrate comprises a plurality of vertical projections or micropillars protruding from the surface of the substrate which define the flow along the substrate. Ideally, the vertical projections consist of areas of projections substantially vertical to said surface, and having a height (H), diameter (D) and reciprocal spacing such, that lateral capillary flow of the liquid sample in the flow path zone is achieved.

It will be understood that the following description refers to such blood coagulation assays, however, the coagulation of other liquid samples may be contemplated in accordance with the invention. Thus, samples that contain thrombin or fibrinogen may be tested, including blood or plasma or any other liquid containing thrombin or fibrinogen.

The following description and examples refer to blood coagulation assays, however, the coagulation of other liquid samples may be contemplated in accordance with the invention. Furthermore, it will be understood that the following comments are applicable to both the first and second aspects of the invention.

Substrate Materials

The characteristics of a lateral flow device can be highly influenced by several factors including: surface porosity, roughness etc. Therefore, the choice of an appropriate platform or substrate is crucial to the device. Such a base/substrate material must be chemically inert and biocompatible to minimize non-specific interaction and unwanted protein adsorption. Low roughness and porosity is also required. Good optical properties, high heat resistance and low manufacturing cost are also beneficial.

The lateral flow assay substrate may be a plastic material, preferably a thermoplastic material.

Ideally, the lateral flow assay is made of a cyclic polyolefin (COP).

Cyclic-olefin polymers (COPs) is a preferred glass-like material with high transparency, low specific gravity, low water absorbency, as well as low auto-fluorescence and high UV transmission which make them material excellent for biomedical applications. COPs are thermoplastic resins with an excellent combination of optical and electronic properties desired for a substrate for blood coagulation monitoring device. COPs have a high moisture barrier for a clear polymer along with a low absorption rate. It has also been noted as a halogen-free product and a high purity product with little to no extractables which make it useful in diagnostic and medical devices. If required several forms of sterilization i.e. gamma radiation, steam and ethylene oxide can be carried out. The viscosity and stiffness may vary due to monomer content. The glass transition temperature of these polymers can exceed 150° C. (IUPAC Technical Report). High heat resistance makes this polymer suitable material for any thermal modification, i.e. hot-embossing. The creation of various structural designs is possible. COPs can be converted into desired shape and dimensions platform using different types of molding i.e. injection molding.

One such COP is marketed by Zeon Corp. under the brand name Zeonor®. This material has been used as the foundation of lateral flow assay technologies. One such technology developed by Åmic Br. (Sweden) has created an ordered array of micropillars to include and control capillary filling forces when liquid samples are applied to the substrate. Zeonor® is extremely hydrophobic (contact angle ~100°). Thus, COPs with such hydrophobic properties require modification for use in coagulation assays.

Other COPs include TOPAS® (Ticona), APEL® (Mitsui Chemical's), ARTON® (Japan Synthetic Rubber's) and Zeonex® (Zeon Chemical's).

Alternatively, other plastic materials may be used as the lateral flow assay substrate. Other suitable plastic materials include Polystyrene; Polyesters—Polyethylene terephthalate (polyester) (PET), polycarbonate (PC), polyvinyl chloride; Natural polymer resins; and/or Polymethylmethacrylate (PMMA).

Additionally, the lateral flow assay substrate may be a silicon or glass-like/ceramic material.

Coating Materials/Surface Modifications

In the present invention, the lateral flow assay substrate material may be modified by the deposition of surface modifications or surface chemistries (i.e. a so called "coating material"), which accelerate the coagulation of blood or plasma. In this manner, a film, layer or coating of an additional material is deposited on the substrate surface to modify the substrate surface chemistry.

After modification, the coagulation process then brings about changes in the filling time and/or distance travelled by the clotting blood or plasma sample along the device. This can be used to monitor, for example, the impact of anti-coagulant drugs on the ability of the sample to form a clot.

Ideally, the surface modification increases the surface activity/hydrophilicity of the substrate to allow improved fluid flow through the lateral flow assay device. Creation of a hydrophilic surface with associated increases in surface energy may be also beneficial in the reduction of non-specific interactions and protein adsorption. Surface modification results in changes to the polymeric material characteristics such as charge density, surface chemical composition, surface chain mobility, wettability, surface tension and many other parameters that significantly influence biological responses such as a conformation, adsorption rate and the kinetics of molecules interacting with the surface). The increase in surface tension can be explained by the formation of new functional groups on the polymer surface. However, the gained effect of the surface wettability may decrease with time, due to contact with air or water.

Ideally, the coating material is water-stable and uniform wherein the effect of modification/hydrophilicity would not deteriorate over a long period of time. Changes in surface properties can be easily monitored and quantitatively ascertained using contact angle measurements. Additionally, the coating material is characterised by low roughness and porosity which can be determined by Atomic Force Microscopy (AFM). Furthermore, the coating process should be cost-effective and the operator should not be exposed to hazardous conditions.

Various surface modifications may be contemplated as listed below and defined in the first and second aspects of the invention:

i. As defined in the first aspect of the invention, the surface modified substrate may be further modified with a range of materials, preferably the clotting agent fibrinogen or thrombin, that enhance or promote the blood coagulation process, the so-called "reagent materials" listed below. Thus, the surface modification itself may enhance or promote the blood coagulation process. Such modifications aim to increase the surface hydrophilicity and facilitate the flow within lateral flow assay device. Accordingly, such reagents may be deposited on the substrate surface after modification according to (i) and (ii) above has taken place.

ii. As defined in the second aspect of the invention, a coating of metal oxide, preferably $SiO_x$, is deposited on the surface of the lateral flow assay device. Ideally, the metal oxide, preferably $SiO_x$, is deposited using PECVD (plasma enhanced chemical vapour deposition).

A preferred embodiment of this aspect of the invention comprises a layer of $SiO_x$ deposited on the surface of the polymer Zeonor® (a COP). Advantageously, we have found that a layer of $SiO_x$ deposited on the surface of the polymer Zeonor® (a COP) enhances the performance of lateral flow blood coagulation assays by increasing surface activity/hydrophilicity to allow improved fluid flow, while also inducing the clotting cascade.

In this manner the $SiO_x$ coating substance acts in an analogous fashion to glass, or other highly negatively charged biomimetic silicate surfaces which resemble the exposed collagen in damaged vasculature, which leads to blood coagulation enhancement.

The ability of the $SiO_x$-modified COP substrates to reduce the plasma clotting time was studied. We surprisingly found a positive correlation between the pro-coagulant activity and the age of the $SiO_x$-coated COP. We found that the $SiO_x$ surface presented a low percentage of reduction in CT (clotting time) during the first few days after deposition (approx. 1%) and was still similar after a week (approx. 2%). However, the surface appeared to improve significantly after two weeks (38% CT reduction). These variations further increased to reach CT reduction values of some 51-54% after approximately three to eight weeks, approaching the CT reduction of glass (FIG. 23).

iii. As defined in the second aspect of the invention, the modified substrate surface may also undergo polyelectrolyte (PE) modification in addition to the SiOx coating or alone. In this manner a layer of PE is adsorbed on the surface of the substrate. Such a polyelectrolyte is neutral polycation polyanion mixture.

Suitable polyelectrolytes include poly(oxyethylene), poly(ethyleneimine) (PAI) or poly(acrylic acid) (PAC). Other polyelectrolytes may be contemplated. We have found that these polyelectrolytes radically reduce non-specific protein adsorption and increase hydrophilicity of the substrate surface.

Polyelectrolyte modification may take place on its own wherein the substrate is dip coated with polyelectrolyte after oxygen plasma treatment.

Alternatively, polyelectrolyte modification may takes place after $SiO_x$ deposition as defined above, and comprises two steps, oxygen plasma treatment followed by dip coating with polyelectrolyte.

According to a preferred embodiment of this aspect of the invention, oxygen plasma treatment of the substrate is carried out in a radio frequency (RF) PECVD reactor. PE treatment is carried out immediately after completion of the oxygen plasma process. PE treatment may comprise dipping the substrate in PEI and subsequently PAC several times.

Both these coating materials types, the metal oxide and polyelectrolyte, may be deposited on the substrate/platform surface. We have advantageously found that these coating material surface modifications provide for an assay device with highly defined lateral flow characteristics. This results in good control of the device filling speed, along with good mixing of sample and assay reagent in a simple, passive and potentially low cost system.

Deposition of metal oxide coatings for example provides an enhancement of the chemical and mechanical properties of a substrate/platform material while a low deposition temperature allows the coating of glass or plastic substrate/platform materials, which can be thermally sensitive Additionally, coating materials comprising films or layers generated by plasma-enhanced chemical vapour deposition (PECVD) offer several advantages over films produced by conventional polymerization. These thin layers or films are highly coherent and adherent to a variety of substrate films and may be prepared from monomers not polymerisable by conventional means).

Advantageously, the surface modified device of present invention addresses several problems experienced by other lateral or capillary flow devices including the lack of precision resulting from the use of conventional lateral flow materials such as nitrocellulose.

It will be understood that the substrate surface has been modified to increase surface activity/hydrophilicity with excellent surface uniformity to facilitate improved liquid fluid flow through the device, with regard to the linear flow velocity, filling with a uniformly defined fluid front and good device reproducibility and stability.

Assay Types

It will be understood that the lateral flow assay device of the invention is suitable for the induction of assays using the intrinsic coagulation pathway, such as activated clotting time [ACT], activated partial thromboplastin time [aPTT] or the extrinsic pathway, such as prothombin assay [PT].

Two pathways or coagulation cascades lead to the formation of a clot, known as the intrinsic and extrinsic pathways. These two pathways are initiated by distinct mechanisms but converge along a common pathway. Clot formation in response to an abnormal vessel wall in the absence of tissue injury is the result of the intrinsic pathway and clot formation in response to tissue injury is the result of the extrinsic pathway. The coagulation cascades are very complex and involve a number of different proteins known as clotting factors.

The following assays may be carried out using the assay device and method of the invention.

Prothrombin Time (PT) Test

A useful measure of coagulation is the prothrombin time (PT) test. The PT test measures the tissue factor-induced coagulation time of blood or plasma. This can provide an assessment of the extrinsic coagulation pathway and is sensitive to factors I, II, V, VII and X. The test is performed by adding a clotting agent such as thromboplastin and Ca2+ to a patient sample and measuring the time for clot formation.

However, the traditional expression of PT test results is inadequate for international comparison because the values depend upon the nature of the thromboplastin used. This has lead to the adoption of the Internationalised Normalised Ratio or INR as a way of expressing prothrombin time. The ISI is derived from the calibration line of the value of PT for a number of samples, obtained using a particular thromboplastin versus the World Health Organisation (WHO) international reference preparation for thromboplastin (human combined 67/40). A particular value of ISI, which takes into account the particular method and type of thromboplastin used, is assigned to each PT system, whereby each PT ratio can be translated into a standardized ratio. By employing INR, patients should be able to maintain a satisfactory level of coagulation which is independent of the PT system used.

Activated Partial Thromboplastin Time Test (APPT)

Another method of measurement of coagulation in either blood or plasma is the Activated Partial Thromboplastin Time Test (APTT). This test is a measure of the time of coagulation that occurs when the intrinsic pathway is activated. This is achieved by the addition of an activator (kaolin) to the sample in the presence of calcium ions and phospholipid (partial thromboplastin). APTT is used to evaluate the intrinsic coagulation pathway which includes the factors I, II, V, VIII, IX, X, XI and XII. Formation of complexes on the surface of the phospholipid enables prothrombin to be converted into thrombin, which results in clot formation.

APTT is used as a routine test for monitoring heparin therapy during surgical procedures, as a preoperative screening test for bleeding tendencies and to assess the overall competence of the patient's coagulation system.

Activated Clotting Time Test (ACT)

This test resembles the APTT test and is used to monitor a patient's coagulation status during procedures that involve the dosing of high amounts of heparin, such as percutaneous transluminal coronary angioplasty (PCTA) and cardiopulmonary bypass surgery. The ACT test is considered as one of the best laboratory tests for the control of heparin therapy, both for patients undergoing treatment for thromboembolic disease and for those on extra-corporeal circulation. For those patients taking heparin, prolongation of the ACT is directly proportional to the concentration of heparin in blood. Monitoring is important and underdosing or overdosing of heparin may result respectively in pathological thrombus formation or serious hemorrhagic conditions. This test measure the clotting time after the addition of a coagulation activator such as celite, kaolin or glass.

Thrombin Time Test (TT)

This test measures the rate of formation of a fibrin clot in plasma by the action of thrombin on fibrinogen, compared to a normal plasma control. The test is performed by adding a standard amount of thrombin to a patient's plasma that has been deprived of platelets and measuring the time for a clot to form. It has been used in the diagnosis of disseminated intravascular coagulation and liver disease and is generally performed in the central laboratory. This is a qualitative measurement of fibrinogen. The Clauss method described below is a quantitative measurement of the amount of fibrinogen present.

Other Tests

Clotting assays have been developed which target specific factors such as factor Villa that is indicative of factor IX deficiency. Another example is an assay for factor VIII, which constitutes a test for haemophilia. Other tests include assays to measure the levels of activation peptide factor IXa, antithrombin, protein C and protein S, fibrinogen deficiency, lupus antibodies or any disease-state or condition that maye relate to blood viscosity.

For instance, it has been shown that blood viscosity is a good determinant for adverse cardiovascular events (Lowe et al Br J Haematol. (1997) January 96(1):168-73. Furthermore, the device and method of the invention are particularly useful for the monitoring of fibrinogen levels variations. As described in "Guidelines on Fibrinogen Assays" British J of Haematology (2003) 121: 396-404, fibrinogen assays can advantageously be used individually as a predictor of a variety of arterial cardiovascular events or as a screening test along with PT and aPTT. One such assay is the Clauss assay (1957) in which a high concentration of thrombin (ranging from 35 to 200 U/ml, typically 100 U/ml) is added to dilute test plasma and the clotting time is measured. The test result is compared with a calibration curve prepared by clotting a series of dilutions of a reference plasma sample of known fibrinogen concentration, and a result in g/l is obtained. Additionally, PT-derived (PT-fg) tests derived from prothrombin time have been widely used in recent years. This is an indirect measurement of fibrinogen, Other suitable assays are described in "Guidelines on Fibrinogen Assays" British J of Haematology 2003, 121, 396-404.

The device and method of the invention may also be used for the monitoring of direct thrombin inhibitors as described in Love Jason E. et al "Monitoring direct thrombin inhibitors with a plasma diluted thrombin time" Thrombosis and haemostasis (2007) vol. 98, no 1:234-242). In this paper. plasma diluted thrombin time was found to be a viable alternative to aPTT for monitoring direct thrombin inhibitors (DTI) levels, especially in patients with lupus inhibitors or low levels of vitamin K-dependent factors. In this way, thrombin may be deposited and dried onto the device of the invention either alone or in combination with aPTT/PT reagent, as described in relation to the TT assay above.

Micropillar Aspect

In a general context the device of the invention comprises a substrate with at least one flow path and functional means in which liquid samples can be treated by desired procedures, wherein at least one flow path is/are laid out to form a pattern for the transport of liquid samples to, through and from said functional means. In this manner the flow path consists of a plurality of micro posts protruding upwards from said substrate; wherein the spacing between the micro posts is such as to induce a capillary action in a liquid sample applied anywhere to said flow path, so as to force said liquid to move from where said liquid sample was applied.

According to a preferred embodiment of the present invention, the flow path zone of the substrate comprises a plurality of vertical projections protruding from the surface of the substrate which define the flow through the substrate. These are known as "micropillars" or microprojections" or "protruding microstructures". The device with such micropillars may also be known as a "micropatterned device".

Ideally, the vertical projections consist of areas of projections substantially vertical to said surface, and having a height (H), diameter (D) and reciprocal spacing such, that lateral capillary flow of the liquid sample in said flow zone is achieved. Such a device is disclosed in WO 03/103835, WO 2005/089082, WO 2006/137785 and related patents, the contents of which are incorporated herein by reference.

According to one embodiment, such an assay device ideally comprises a non-porous substrate having a substrate surface and at least one fluid passage or defined flow path with projections substantially perpendicular to said substrate surface, said projections having a height, diameter and a distance or distances between the projections, capable of generating capillary flow, lateral to said substrate surface, of a sample fluid through the fluid passage.

It will be understood that the fluid passages define the flow path and support capillary flow.

In one embodiment, the micropillars or projections have a height in the interval of about 15 to about 150 µm, preferably about 30 to about 100 µm, a diameter of about 10 to about 160 µm, preferably 20 to about 80 µm, and a distance or distances between the projections of about 5 to about 200 µm, preferably 10 to about 100 µm from each other. The flow channel may have a length of about 5 to about 500 mm, preferably about 10 to about 100 mm, and a width of about 1 to about 30 mm, preferably about 2 to about 10 mm. It should in this context be noted that a device according to an embodiment of the invention does not necessarily have to have a uniform area of micropillars, but that the dimensions, shape and a distance or distances between the projections of the micropillars may vary in the device. Likewise, the shape and dimensions of the fluid passage may vary.

Ideally, at least one fluid passage is a passage supporting capillary flow.

The use of an assay device with micropillar projections provides for the precise fluid flow along the assay device making its performance superior to other conventional systems.

The device may be a disposable assay device or part of such device.

According to a preferred embodiment of this aspect of the invention, there is provided a micropatterned substrate with $SiO_x$ deposited, preferably using PECVD. Ideally, the micropatterned substrate is a cyclic polyolefin. We have found that this device resulted in good surface wettability, imparting reproducible microfluidic characteristics to the lateral flow device.

Alternatively, a layer of clotting agent, namely fibrinogen or thrombin or a derivative thereof, may be applied to the micropillar surface, ideally along the defined flow path.

Other embodiments to this aspect of the invention may be contemplated using micropatterned substrate which have been modified or patterned in such a way as to enhance the performance of the device for monitoring blood coagulation. For example, the length and width of the channel can be selected which perform most effectively. Thus, the height of, size of, and distance between micropillars may be chosen depending on the particular end use.

Additionally, the structure/2D-3D organization of the micropillars may be altered. In this way the micropillars may be present in particular pre-defined configurations which ideally enhance the retardation of blood flow through the strip during clotting, For example, a narrowing or plurality of narrowings may be formed in the lateral flow channel.

Other embodiments may also be contemplated. For example, the creation of an "incubation chamber" (containing coagulation reagents) in a sample application zone would allow a clotting to occur before entry of the sample into the test channel. This would allow the flow cessation of the clotting sample to occur earlier in the channel giving a longer distance to be traversed by anticoagulant-treated sample and, this way, better differentiation between the normal and abnormal samples.

Additionally, a soluble barrier composed of a dissolvable film may be used. Once in contact with liquid, the dissolvable film would start to decompose (taking approx. 10 to 180 seconds depending on the particular application) while the clotting process has been initiated. Ideally, once the soluble barrier had been overcome, most of the liquid (sample components) of a normal clotting sample would be trapped in the clot and only a small fraction would progress into the test channel and travel short distance, while abnormal clotting sample (anticoagulant treated) would travel a proportionately longer distance (depending on the anticoagulant concentration).

According to a further aspect of the invention, there is provided a method for monitoring and measurement of clotting in a liquid sample using the lateral capillary flow device according to the invention as defined in the first and second aspects of the invention wherein the sample is added to the receiving zone on the substrate and is transported through capillary action from the receiving zone through a flow path such that lateral capillary flow of said liquid sample is achieved.

Ideally, the method is suitable for the induction of assays using the intrinsic coagulation pathway, preferably activated clotting time [ACT], activated partial thromboplastin time [aPTT] and/or the extrinsic pathway, preferably the prothombin assay [PT].

The lateral flow device of the invention comprises a $SiO_x$-coated substrate surface or a PE modified substrate surface. Alternatively, the $SiO_x$-coated substrate surface may be further modified by PE. Ideally, the modified substrate surface provides a CT reduction value of approximately 35 to 45%.

Alternatively, the lateral flow assay device of the invention comprises a coating of a clotting agent preferably fibrinogen or thrombin or a derivative thereof.

In order to carry out these assays and assess coagulation/clotting times, the conversion of the sample from liquid to gel (clot) state in time and/or distance travelled is measured. Thus, it is important to rapidly induce the formation of a strong, dense clot and prevent the separation of the sample into a fibrin mesh and serum.

Ideally, a strong clotting activator should be used to rapidly induce formation of a strong, dense clot that would capture most of the liquid and therefore slow down or prevent the flow at some stage along the channel. A strong, rapidly acting activator deposited uniformly or in a gradient along the channel would cause a liquid conversion into a dense fibrin mesh and therefore a cessation of a flow thereby allowing the distinction between clotting and non-clotting samples on the basis of time and/or distance travelled.

Ideally, PT/aPTT activators could be used for this purpose. PT reagents were found to be especially useful. They contain tissue factor and a combination of phospholipids which activate the coagulation cascade through the extrinsic pathway rapidly (approximately 10 to 12 seconds).

According to a still further aspect of the present invention, there is provided a method for the deposition of $SiO_x$ on the surface of a lateral capillary flow device wherein the device comprises a non-porous substrate with a zone for receiving a sample and a defined flow path zone wherein the surface of the substrate has been modified to accelerate the coagulation of the liquid sample wherein the method comprises
  a. treating the substrate with oxygen plasma and argon; and
  b. subjecting the substrate to $SiO_x$ deposition using plasma enhanced chemical vapour deposition (PEVCD).

It will be understood that this coating substance can be deposited by a number of means. A preferred embodiment of deposition utilizes oxygen plasma treatment followed by plasma enhanced chemical vapour deposition (PECVD). This allows the modification of the wettability, hardness, chemical inertness and biocompatibility of the substrate. Thus, films generated by PECVD offer several advantages over films produced by conventional polymerization. These thin layers are highly coherent and adherent to a variety of substrate films and may be prepared from monomers not polymerizable by conventional means.

Various parameters as outlined in the examples have been optimised for this method including RF power, the use of argon in a pre-treatment step, supply of used gases and liquid precursor, HMDSO, ratio of argon to oxygen and time of treatment. Ideally, the $SiO_x$ deposition process was carried out in two steps: a pre-treatment step using oxygen plasma with or without addition of argon and a $SiO_x$ coating step in which the precursor, HMDSO, reacts with oxygen under given RF power to create $SiO_x$, species deposited onto the substrate surface.

Ideally, a uniform coating of $SiO_x$ of approximately 35 to 55 nm, preferably 40 to 50 nm, more preferably, 44 to 46 nm is desirable.

Alternatively or additionally, the substrate surface may be subjected to polyelectrolyte modification wherein the substrate is dip coated with polyelectrolyte after oxygen plasma treatment.

Ideally, the substrate is a plastic material, such as a thermoplastic material, preferably a cyclic polyolefin. Although, other substrates may be utilized as outlined previously.

Ideally, the flow path zone of the substrate being modified comprises a plurality of vertical projections protruding from the surface of the substrate which define the flow through the substrate. According to a preferred embodiment, the vertical projections consist of areas of projections substantially vertical to said surface, and having a height (H), diameter (D) and reciprocal spacing (t1, t2) such, that lateral capillary flow of the liquid sample in said flow zone is achieved, and where means for separation are provided adjacent to or in the zone for receiving the sample. In this manner, the lateral flow assay device used may be in accordance with WO 2006/137785 or 2005/089082 the contents of which are hereby incorporated by reference.

In the specification, the terms "comprise, comprises, comprised and comprising" or any variation thereof and the terms "include, includes, included and including" or any variation thereof are considered to be totally interchangeable and they should all be afforded the widest possible interpretation.

The invention is not limited to the embodiment hereinbefore descried, but may be varied in both construction and detail within the scope of the claims.

BRIEF DESCRIPTION OF THE DRAWINGS

The invention will now be more clearly understood with reference to the following description given by way of example only and the following non-limiting figures and examples.

FIG. 4 a (Size of AFM images 50×50 µm) (FIG. 4 c (Size of AFM images 1×1 µm) and FIG. 4 e (Size of AFM images 1×1 µm))

(FIG. 5 a (Size of AFM images 1×1 µm), FIG. 5 c (Size of AFM images 1×1 µm) and FIG. 5 e (Size of AFM images 1×1 µm))

FIG. 7 a (Size of AFM images 7×7 µm).

FIG. 22 relates to the surface modification of cyclo-olefin polymer by oxygen plasma treatment alone, PAC coating alone, polyelectrolyte treatment, $SiO_x$ deposition alone and $SiO_x$-coated polymer treated with polyelectrolyte. The effectiveness of surface modification was analysed by contact angle measurements. The lowest contact angles and most stable over time were attributed to the $SiO_x$ layer modified with high RF power settings.

FIG. 23 shows video images of fluid velocity measurements to show the quality of fluid flow on the modified surfaces of oxygen plasma treatment alone, PAC coating alone, polyelectrolyte treatment, $SiO_x$ deposition alone and $SiO_x$-coated polymer treated with polyelectrolyte (from left to right).

FIG. 24 are velocity profiles for oxygen plasma treatment alone, PAC coating alone, polyelectrolyte treatment, $SiO_x$ deposition alone and $SiO_x$-coated polymer treated with polyelectrolyte showing that the $SiO_x$-modified surface being most effective in achieving rapid and reproducible lateral flow.

FIG. 25 is example tapping mode AFM 3D height images showing the topography of the plain COP in comparison to the SiOx and PE-treated COP surfaces (from left to right).

FIG. 26 is a comparison of the Rms roughness values obtained from AFM analysis of plain, untreated and modified surfaces, namely plain surface, oxygen plasma treated surface, PAC coated surface, polyelectrolyte treated surface, $SiO_x$ coated surface and $SiO_x$-coated polymer surface also treated with polyelectrolyte (from left to right).

EXAMPLES

Example 1

Figure 1A:
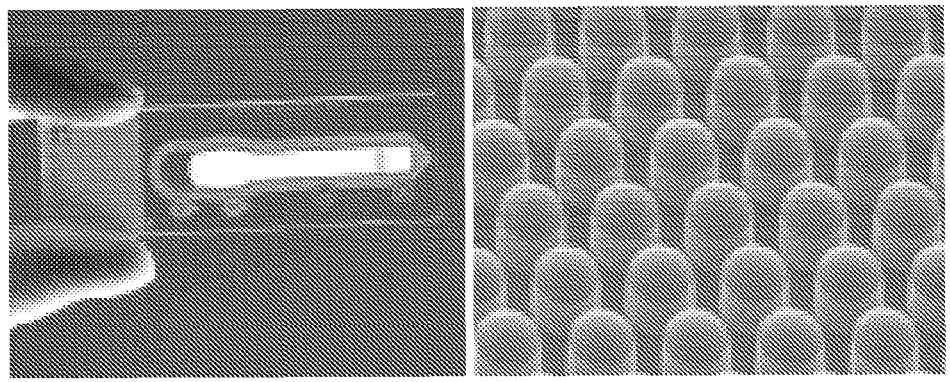
FIG. 1a is directed to the Amic® platform (left) and an exploded view of the micropillars are shown (right). This lateral flow platform is composed of the cyclo-olefin polymer, which was injection molded to create a micropillar array with defined capillary force characteristics for controlled lateral flow assays.

A Method for the Modification and Characterisation of a Cyclic Polyolefin Substrate with Silicon Dioxide
Materials
B2.2 COP Amic® chips (supplied by Åmic BV (Sweden))
  height: 65-70 µm, top diameter: ca 50 µm, bottom diameter: ca 70 µm and cc: 185×85 µm (distance between the centres of the pillars in a row: 85 µm; distance between the centres of the pillars in a column: 185 µm).

Water from a Millipore Milli-Q water purification system (Millipore, US) with a specific resistance of 18.3 MΩ cm or greater;

Hexamethyldisiloxane (HMDSO) at a grade ≥98% (Sigma-Aldrich);

Argon/oxygen at the high purity grade (Premier, 99.9%) (Air Products Ireland Ltd.);

Aqueous food dye solutions (Goodall's™);

96 well black-sided, clear-based, microassay plates (Greiner Bio-One);

Thrombin colorimetric reagent S-2238 (Chromogenix);

Normal citrated human plasma (Hemosil);

Pressure-Sensitive Adhesive (PSA) (AR8890) (Adhesives Research).

Method $SiO_x$ Deposition

The deposition process was carried out in a 13.56 MHz RF PECVD reactor under the process conditions for $SiO_x$ deposition on stainless steel by PECVD described by Prasad [22, 34]. However, deposition process conditions were modified to achieve the desired film properties on the COP substrate. The gases necessary for the deposition process (argon, oxygen and the $SiO_x$ precursor HMDSO) were supplied to the deposition chamber via mass flow controllers connected to the chamber. The HMDSO supply lines leading from source to the manifold and chamber wall were made of stainless steel and heated to 55° C. using a temperature-controlled heating tape to prevent condensation of the precursor. Samples were treated with oxygen plasma prior to $SiO_x$ deposition.

Firstly, vacuum conditions were created. Target chamber pressure was ≤30 mTorr. Once this level was achieved, the surface was treated for three minutes with a supply mixture of oxygen:argon at different ratios under a RF power of 150-500 W. The amount of oxygen supplied was between 0-150 Standard Cubic Centimetres per Minute (SCCM) and argon between 0-134 SCCM. Subsequent $SiO_x$ modification was carried out immediately after the oxygen plasma process was finished, as the effect of this treatment is not stable over time—created functional groups tend to degrade. The argon supply (if used) was cut off after pre-treatment step and the mixture of oxygen:HMDSO (50-500 SCCM: 10-15 SCCM) was applied for 3-30 min. The effect of the dilution of argon (0-100 SCCM) in the deposition step was also tested. Following process optimisation, the best conditions for $SiO_x$ film formation were obtained when samples were exposed to RF power of 250 W, 50 SCCM of argon and 50 SCCM of oxygen for 3 min. and coated at RF power of 300 W, 500 SCCM of oxygen and 15 SCCM of HMDSO for 10 min. Modified samples were stored under ambient conditions. Identical deposition conditions were also used to form films on silicon substrates for physical characterisation of the films using ellipsometry, Fr-IR and ATR.

Atomic Force Microscopy

Atomic force microscopy (AFM) imaging was performed in ambient air using a Dimension 3100 (equipped with Nanoscope IIIa electronics) in the Tapping Mode™ using standard silicon cantilevers (BudgetSensors, Tap300Al) with a radius of curvature of less than 10 nm, a spring constant of 40N/m and a resonance frequency of 300 kHz (nominal values). Topographic images were recorded at a scan rate of 1-2 Hz. The surface roughness was evaluated using the AFM manufacturer software (Nanoscopelll, V5.12). The image "root mean square" (Rms) calculated in nanometers was defined as the average of height deviations taken from the mean plane. 4-5 locations on 2-3 samples were scanned to get the roughness values. Rms values [nm] were averaged. Samples were also analysed in terms of film thickness. A part of the slide was covered with tape which could be removed after coating. Values obtained from scanning of 4 samples were averaged.

Contact Angle Measurements

The substrate surface energy was measured by a video-based contact angle analyser (First Ten Angstroms, FTA200). 3-6 data points were taken for each sample and the contact angle (CA) was measured in several locations on the same sample. To ascertain the stability of the surface over time, CAs were measured regularly over a period of several weeks.

Fourier Transform Infrared Spectrometry and Infrared Attenuated Total Reflection $SiO_x$ film deposited by PECVD on silicon wafer was analysed by infrared absorption spectroscopy using a Fourier Transform Infrared (FT-IR) spectrometer (Perkin Elmer Spectrum GX, FT-IR System) using a ZnSe crystal under the nitrogen atmosphere in Attenuated Total Reflection (ATR) mode applied to clarify the chemical bonding structures in our $SiO_x$ films deposited on COP substrate. The scanning was carried out under 4 $cm^{-1}$ resolution. 32 scans were performed.

Flow Time Experiments

Aliquots of 15-20 μl of an aqueous dye solution or calibration plasma (Hemosil) were added to the substrate sample zones within micropillar channels on the device. The time required for the liquid to flow through and reach the end of the channel was measured by video recording. The video also recorded the quality of the flow.

Chromogenic Thrombin Assay

A chromogenic thrombin assay was performed to determine the effect of the $SiO_x$ coating on normal plasma clotting time (CT). The assay was prepared on 96-well microassay plates. The base of the plate was modified with a layer of double-sided PSA and the base of each well cut away with a scalpel. Modified and unmodified substrates and glass controls were then attached to the adhesive base of the plate. Additional control was assay done on standard, polystyrene base. 50 μl of normal citrated human plasma were placed into the wells. The samples were incubated for 15 min. at room temperature. 50 μl of colorimetric reagent (5-2238) was added to the wells, and finally 50 μl of 25 mM $CaCl_2$ was added which initiates the reaction overcoming the effect of citrate in the plasma sample. The absorbance was measured every 30 sec. at 405 nm for 70 min. at 37° C., using a Tecan, Infinite M200 spectrophotometer. Clotting times were taken as the time corresponding to the absorbance at half the maximum signal.

Results and Discussion

Plasma-Enhanced Chemical Vapour Deposition of $SiO_x$

High $O_2$/monomer ratios and high power are the main points in the recipe for a successful deposition of $SiO_2$-like films. However, because of the complexity of such plasma phases, it is very difficult to determine the correlation between the species densities in the plasma phase and the chemical composition of the deposited film and optimize the process (Creatore, M., Palumbo, F., d'Agostino, R., Fayet, P. (2001). RF plasma deposition of SiO2-like films: plasma phase diagnostics and gas barrier film properties optimisation, *Surface & Coatings Technology*, 142 163). Hexamethyldisiloxane (HMDSO) is our choice of precursor for $SiO_x$ deposition by PECVD on COP substrate. HMDSO, primarily in liquid form, decomposed in PECVD serves the source of active species involved in the coating process.

The $SiO_x$ deposition process was carried out in two steps: a pre-treatment step using oxygen plasma with or without addition of argon and a $SiO_x$ coating step in which the precursor, HMDSO reacts with oxygen under given RF power to create $SiO_x$ species deposited onto the substrate surface. Studies have been carried out to evaluate the effect of argon dilution on the physicochemical properties of a film deposited by PECVD. It has been found that in some cases the argon addition can be beneficial and an enhancement in deposition rate has been noticed. Not only does it bring increased contact area resulting in excellent adhesion of the coating to the polymer surface, but it is also a good cleaning procedure). However, in spite of this positive effect, the dilution of argon in the deposition mixture may not be recommended as it may impact negatively the quality of the deposited layer. As previously postulated by other research groups, this may be due to argon ion bombardment (Kushner, M. J. (1988). A Model for the Discharge Kinetics and Plasma Chemistry during Plasma Enhanced Chemical Vapor Deposition of Amorphous Silicon, *Journal of Applied Physics*, 63 (8): 2532; Keppner, H., Kroll, U., Torres, P., Meler, J., Fischer, D., Goetz, M., Tscharner, R., Shah, A. (1996). Scope of VHF plasma deposition for thin-film silicon solar cells, *Conference Record of the Twenty Fifth Ieee Photovoltaic Specialists Conference—1996*, 669). However, it was also proven that the plasma pre-treatment of the substrate can significantly improve the HMDSO film adhesion to both polymer and metal surfaces (Hegemann, D., Vohrer, U., Oehr, C., Riedel, R. (1999). Deposition of SiOx films from O-2/HMDSO plasmas, *Surface & Coatings Technology*, 119 1033; Domingues, L., Oliveira, C., Fernandes, J. C. S., Ferreira, M. G. S. (2002). EIS on plasma-polymerised coatings used as pre-treatment for aluminium alloys, *Electrochimica Acta*, 47 (13-14): 2253. For these reasons, the mixture of oxygen and argon was tested as well as oxygen dilution on its own.

Both RF power and the oxygen:HMDSO ratio applied in the deposition process have been found to have a defined impact on adhesion strength of coating (Prasad, G. R., Daniels, S., Cameron, D. C., McNamara, B. P., Tully, E., O'Kennedy, R. (2005). PECVD of biocompatible coatings on 316 L stainless steel, *Surface & Coatings Technology*, 200 (1-4): 1031). Two sets of conditions were applied which evaluated the effect of RF power and oxygen:HDMSO ratios at 500 W, 100:15 SCCM ($SiO_x1$) for 10 min and 150 W, 50:10 SCCM for 3 min ($SiO_x2$), respectively (where the pre-treatment conditions were: $SiO_x1$ RF 500 W, 100 SCCM oxygen, 3 min; $SiO_x2$, RF 150 W, 50 SCCM oxygen, 3 min).

Figure 2:
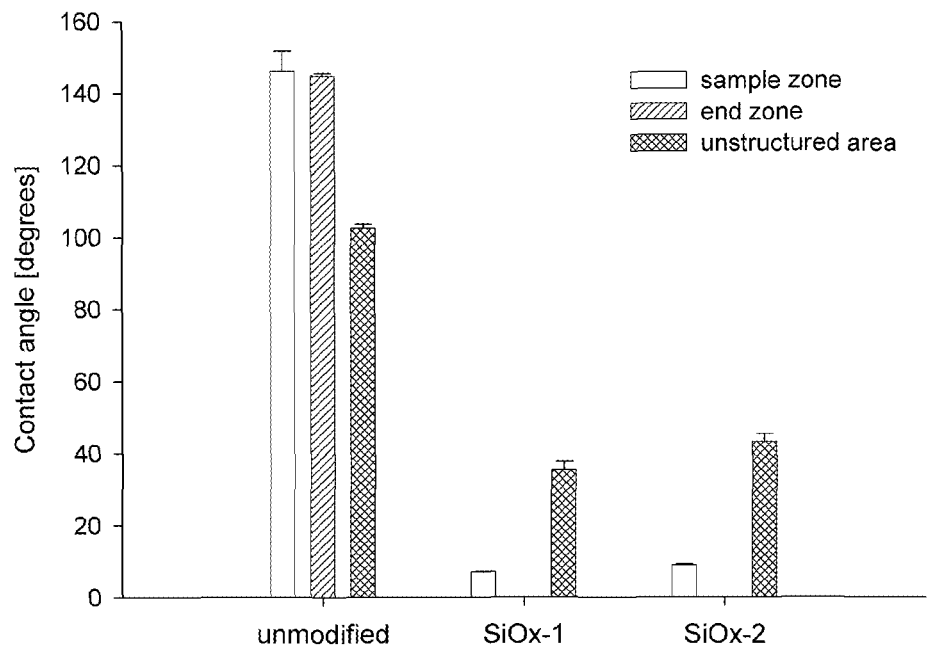
FIG. 2 shows the effect of $SiO_x$ coating on CA values measured 24 h following modification in three different locations on the modified COP substrates: on a sample zone (microstructured), end zone (microstructured) and in the smooth area without micropillars, compared to the CAs in mentioned locations of an unmodified chip.

Two of the chips exposed to high RF power (500 W) were melted and burned on the sides so the chemical structure of the polymer was clearly affected by high power. However, the samples that stayed visually unchanged, clear and transparent were tested. FIG. 2 shows the effect of the treatments on the CA values (wettability) of particular areas. The CA values were checked on control, unmodified COP surface. It can be seen that the treatment has a significant effect on reducing the CA from untreated surface values of 100° and 140° to modified surface values of 50° and significantly below. It has also been observed that the microstructured (micropillar zones) have much lower apparent CA due to the natural capillarity introduced by the surface patterning which resulted in extremely hydrophilic surfaces of below 10°. CA measurements were not possible on the end zone due to the high wettability of the modified surface. $SiO_x1$ also appeared to be marginally better in overall reduction in CA.

Figure 3:
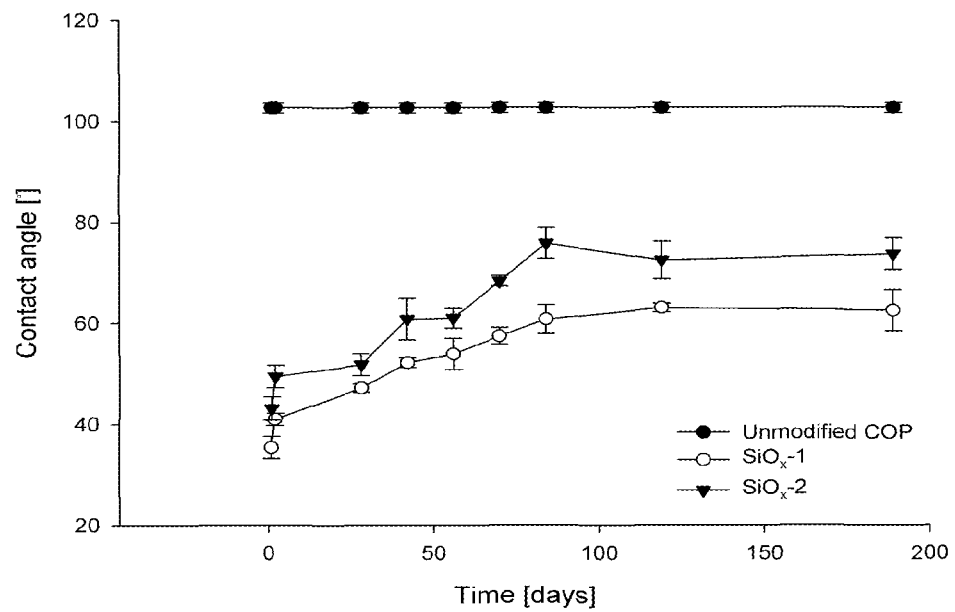
FIG. 3 shows the change of CA values over time for COP substrate unmodified and modified via PECVD with $SiO_x$ at two different conditions (n=3).

The stability of the surface modification was monitored over several weeks (FIG. 3) by analysing the unstructured surface of the substrate. Over time, the CA was increasing until after approximately 12 weeks, where it began to stabilise. $SiO_x1$ high power deposition remained significantly more hydrophilic than $SiO_x2$, reflecting the initial values achieved. Both followed a similar change in surface properties over time, stabilising at 60° and 70°, respectively.

From the previous data it was shown that too high RF power (over 450 W) may lead to COP sample overheating and damage. However, a reduction in RF power may result in decreased film hydrophilicity, as the precursor decomposition rate is highly dependent on the power applied. An RF power of 250 W in the pre-treatment step and 300 W in the coating process were found to be optimal to obtain good quality films and to eliminate the risk of sample damage. Film adhesion was further improved by changing the deposition conditions, such as the $O_2$/HMDSO ratio, $O_2$ and Ar dilution and deposition time. The addition of oxygen in the coating step was essential, as $O_2$ was necessary to create $SiO_x$ in the presence of the HMDSO precursor. Film characterization was performed on the surface coated with $SiO_x$ under the optimal conditions as follows. Samples were exposed to RF power of 250 W, 50 SCCM of argon and 50 SCCM of oxygen for 3 min. and coated at RF power of 300 W, 500 SCCM of oxygen and 15 SCCM of HMDSO for 10 min. The optimised coating was stable in water, exhibited satisfactory hydrophilicity (CA of approx. 61-64°), which did not deteriorate significantly over time. Chips coated with $SiO_x$ under these conditions did not require special post-modification treatment, and the ambient storage conditions did not significantly affect the film properties, which makes them easy to use. All further studies were based on these deposition conditions unless otherwise stated.

Atomic Force Microscopic Analysis

Figure 4:
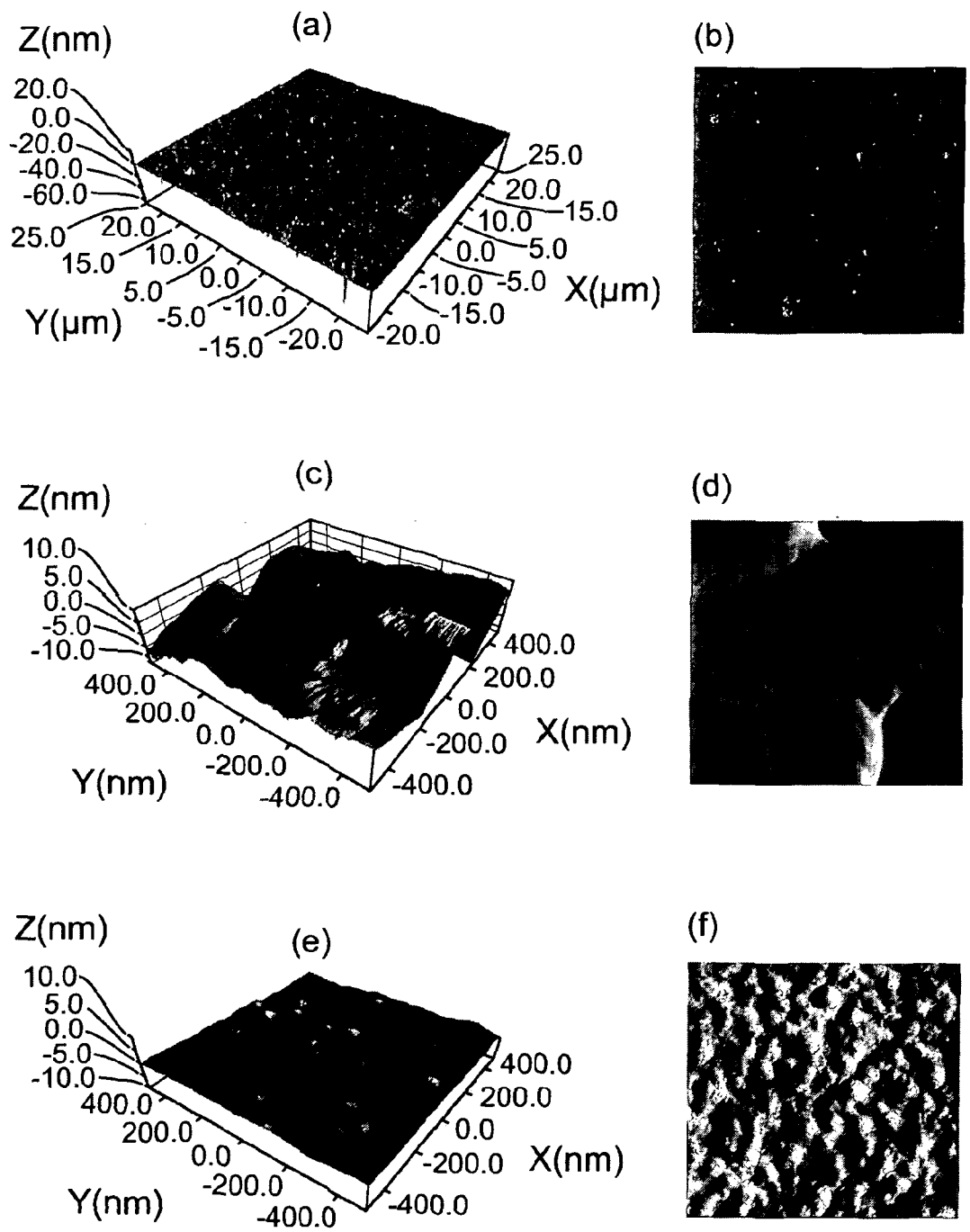
FIG. 4 is a tapping mode AFM images of (a-b) untreated COP surfaces (50 µm×50 µm), (c-d) $O_2$/Ar plasma pre-treated COP (1 µm×1 µm), (e-f) COP modified with $SiO_x$ via PECVD process (1 µm×1 µm). (a, c, e) 30 height image, Z scale: 100, 25 and 20 nm, respectively. (b, d, f) 20 amplitude image, Z scale: 0.1V.
Figure 5:
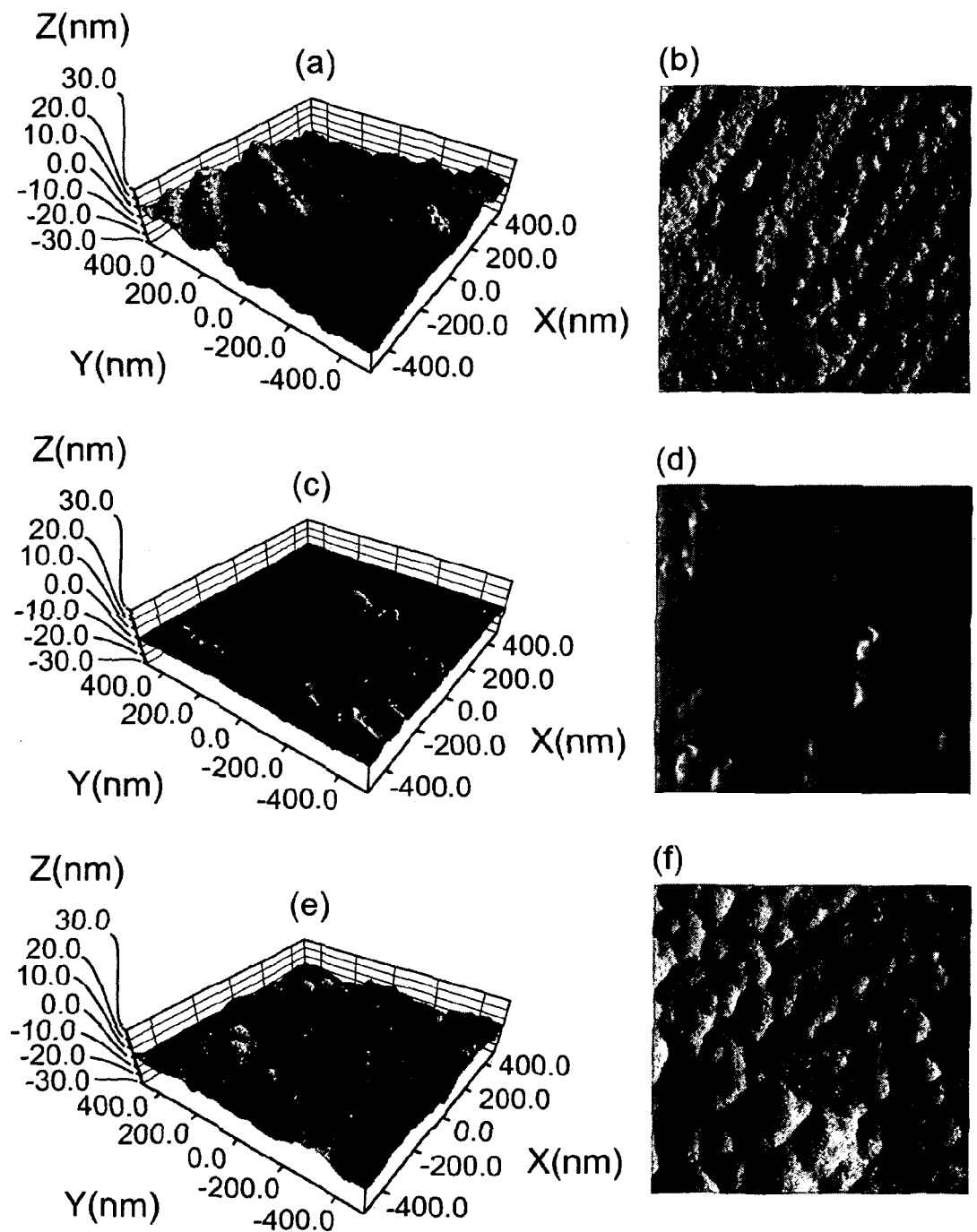
FIG. 5 is a tapping mode AFM images of (a-b) a plain stainless steel surface (1 µm×1 µm), (c-d) $O_2$/Ar plasma pre-treated stainless steel (1 µm×1 µm), (e-f) stainless steel coated with $SiO_x$ via PECVD process (1 µm×1 µm). (a, c, e) 3D height image, Z scale: 80, 80 and 20 nm, respectively. (b, d, f) 2D amplitude image, Z scale: 0.1V.
Figure 6:
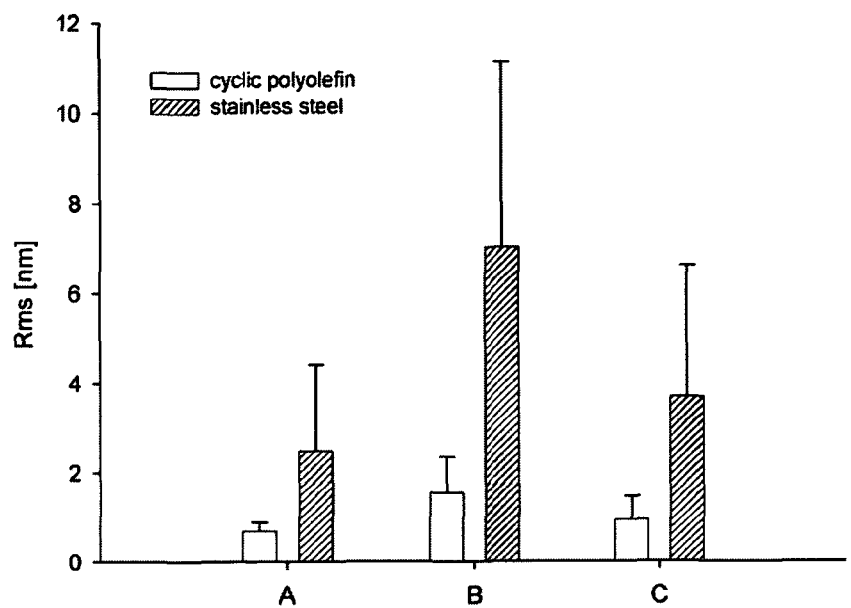
FIG. 6. shows rms values of (A) unmodified, (B) $O_2$/Ar pre-treated, and (C) $SiO_x$-coated COP (black) and stainless steel (grey) substrates (n≥2).

The results of the AFM analysis of the unmodified COP surface, the oxygen/argon pre-treated sample and the surface modified with $SiO_x$ are shown in FIG. 4. For controls, highly polished stainless steel was modified in an analogous way to the COP (FIG. 5). The surface roughness values (Rms) are also shown in FIG. 6. The unmodified surface was extremely smooth at micron length scales with a roughness value of 0.7±0.21 nm. This changed dramatically following oxygen/argon plasma treatment where the level of surface structure increased very noticeably with an accompanying increase in roughness value to 1.54±0.81 nm. Following $SiO_x$ deposition, the surface returned to a slightly smoother and more defined surface structure with a roughness of 0.96±0.51 nm, clearly indicating the presence of distinct surface modification.

By comparison, the stainless steel exhibited a greater surface roughness of the unmodified substrate compared to COP. This translated into a similar pattern of modification following oxygen/argon plasma treatment where it went from 2.48±1.92 nm to 7.02±4.12 nm. The $SiO_x$ modification resulted in a very similar surface morphology to the modified COP substrate, yielding a roughness value of 3.69±2.91 nm. The AFM data confirms that the use of argon in the PECVD process resulted in an increased film roughness. As highlighted above, the $SiO_x$ coating tended to decrease the roughness of the surface after argon pre-treatment.

Another advantage of the use of the COP as a substrate for open lateral flow platform assays has been illustrated. The plain polymer surface was relatively smooth compared to stainless steel. After argon/oxygen pre-treatment, the roughness increased in the case of both tested substrates. The reason for this was probably, as suggested before, due to argon ion bombardment. Argon was not excluded from the mixture as its dilution provides good surface cleaning, which has an impact on the quality of the subsequently deposited film. Argon dilution may improve film adhesion and make it possible to create a more homogeneous, uniform coating. The film homogeneity may have a significant impact on the reproducibility of the fluidic properties of the resulting surfaces. Argon was excluded from deposition step to reduce the surface roughness. The $SiO_x$ coating of the argon/oxygen plasma-treated surface resulted in a smoothing of the surface.

The roughness was not as low as before modification. However, it was reduced significantly in the case of both substrates.

Film Thickness

Figure 7:
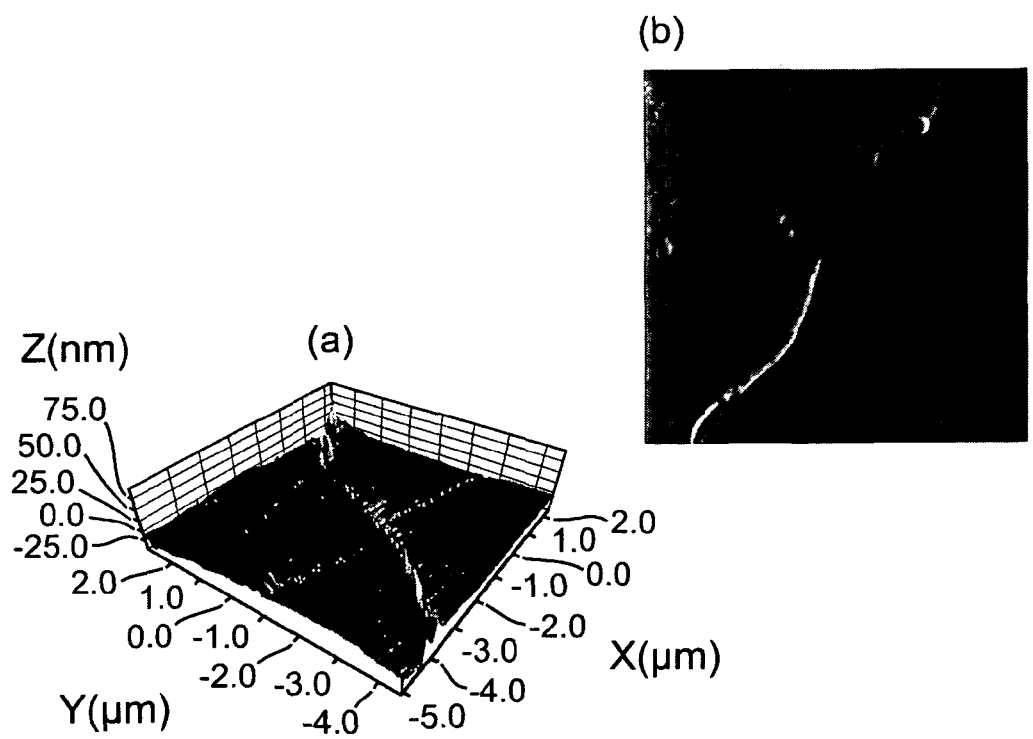
FIG. 7 is a tapping mode AFM images of the border between $SiO_x$-coated and non-coated regions of COP substrate (6 µm×6 µm). (a) 3D height image, Z scale: 140 nm. (b) 2D amplitude image, Z scale: 0.1V.

AFM was also used to estimate film thickness. The thickness of the coating is highly dependent upon the deposition time (Sobrinho, A. S. D., Latreche, M., Czeremuszkin, G., Klemberg-Sapieha, J. E., Wertheimer, M. R. (1998). Transparent barrier coatings on polyethylene terephthalate by single- and dual-frequency plasma-enhanced chemical vapor deposition, *Journal of Vacuum Science & Technology A,* 16 (6): 3190; Yang, M. R., Chen, K. S., Hsu, S. T., Wu, T. Z. (2000). Fabrication and characteristics of SiOx films by plasma chemical vapor deposition of tetramethylorthosilicate, *Surface & Coatings Technology,* 123 (2-3): 204). FIG. 7 shows an AFM image of the boundary between modified and unmodified surface. The step between the two surfaces can be clearly seen in the 3D image. The step height was estimated to be 44.4 nm (0.05% RSD, n=5).

Fourier Transform Infrared Spectroscopy in Attenuated Total Reflectance Mode

To further characterize the $SiO_x$ coating, a qualitative study was carried out using ATR-FTIR on unmodified and $SiO_x$-coated COP substrates. This technique is highly sensitive, selective, non-destructive and can be carried out under ambient conditions. It is further appropriate for characterising silicon-based coatings (Weldon 1999, Niwano 1994, Watanabe 1998, Nagai 2001, Mink 1997).

Figure 9:
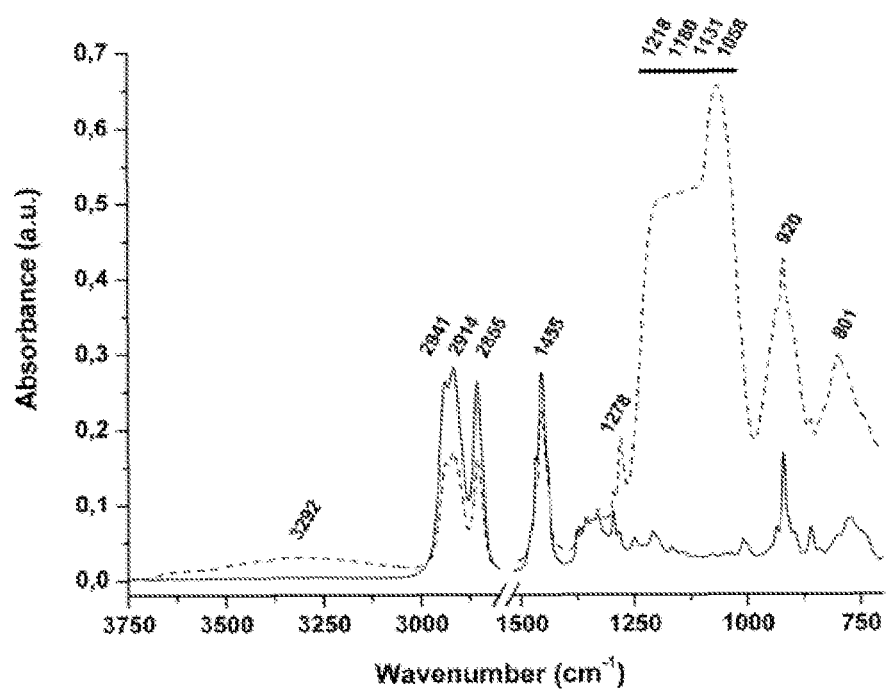
FIG. 9 is an absorbance ATR spectrum of a comparison of $SiO_x$-coated COP (dashed line) and blank, untreated COP (solid line).

As shown in FIG. 9, the ATR-FTIR spectra show various vibrations in two different regions: 3500-2800 $cm^{-1}$ and 1500-750 $cm^{-1}$. The peaks are attributed based on the handbook of G. Socrates (Socrates 2004). In the first region, a broad band between 3750 and 3000 $cm^{-1}$, that can be fitted with two contributions centred at 3565 and 3292 $cm^{-1}$, corresponding to isolated and associated Si—OH stretching vibrations (Theil 1990). A peak at 2941 $cm^{-1}$ is associated to asymmetric stretching mode vibration of $CH_3$ groups. The peaks at 2914 and 2855 $cm^{-1}$ can be attributed to asymmetric and symmetric stretching of $CH_2$, respectively. Those peaks are arising from the substrate, as they appear on both graphs.

In the second region (1500-750 $cm^{-1}$), a peak due to the substrate appearing at 1455 $cm^{-1}$ is associated to C=H bending vibrations of $CH_2$. A peak appearing at 1278 $cm^{-1}$ corresponds to methyl silyl Si—$(CH_3)_x$ vibration. The broad band in the 1250-980 $cm^{-1}$ region, can be fitted with four contributions at 1218, 1180, 1131 and 1058 $cm^{-1}$ attributed to stretching vibration of the Si—R chain, the symmetric stretching of Si—O—Si, the asymmetric stretching vibration of Si—O—C, and stretching vibration of Si—O—Si, respectively. The peak corresponding to Si—OH stretching vibration occurs at 920 $cm^{-1}$. The peaks at 801 $cm^{-1}$ corresponds to Si—O—C stretching mode. These data, along with CA and AFM data, indicate that the surface is efficiently modified with a $SiO_x$ layer.

Figure 8:
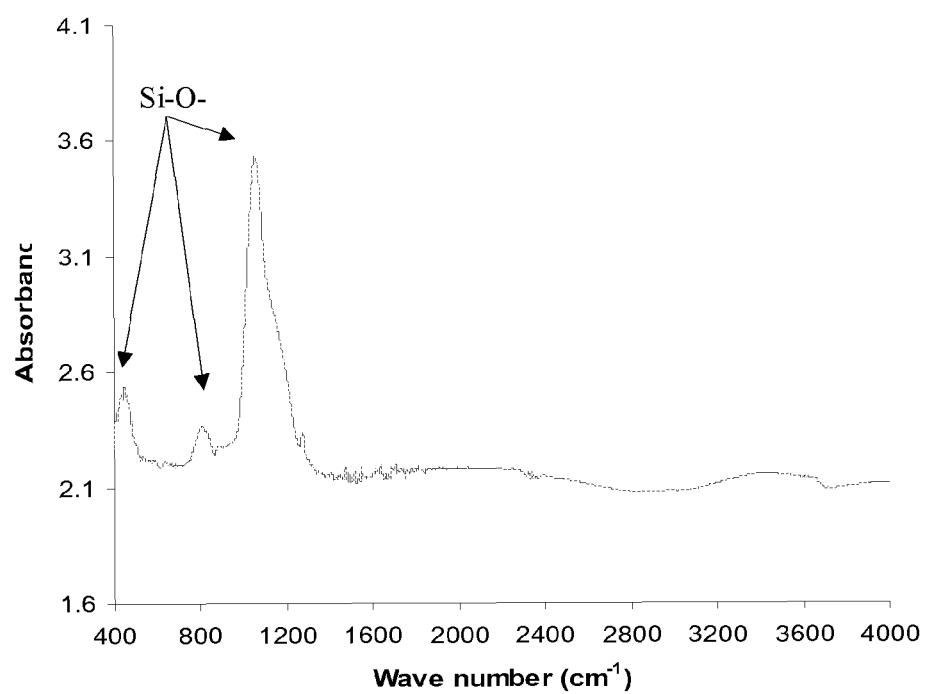
FIG. 8 is an absorbance FT-IR spectrum of $SiO_x$ coatings deposited by PECVD on silicon wafer.

FIG. 8 shows the infrared spectrum of the $SiO_x$ deposited on a silicon wafer. Three main peaks that can be seen around 450, 800 and 1070 $cm^{-1}$ correspond to Si—O—Si vibrational modes; rocking mode, bending mode and stretching mode, respectively (Benissad, N., Aumaille, K., Granier, A., Goullet, A. (2001). Structure and properties of silicon oxide films deposited in a dual microwave-rf plasma reactor, *Thin Solid Films,* 384 (2): 230). The presence of Si—O— bonding on silicon wafer does not give a 100% confidence that these species are present on coated COP.

Fill Time Studies

Figure 1B:
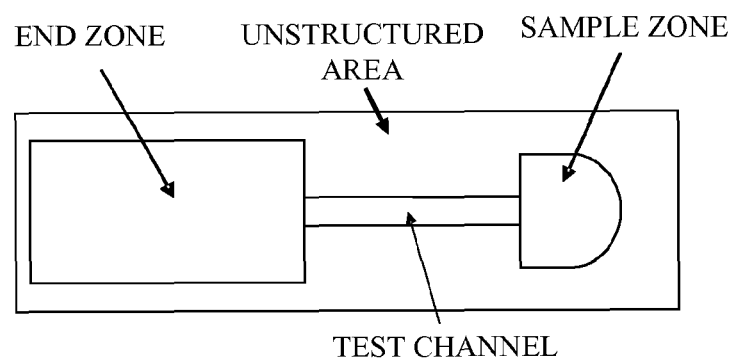
FIG. 1b shows a typical lateral flow assay with unstructured area (1), end zone (2), test channel (3) and sample zone (4).
Figure 10:
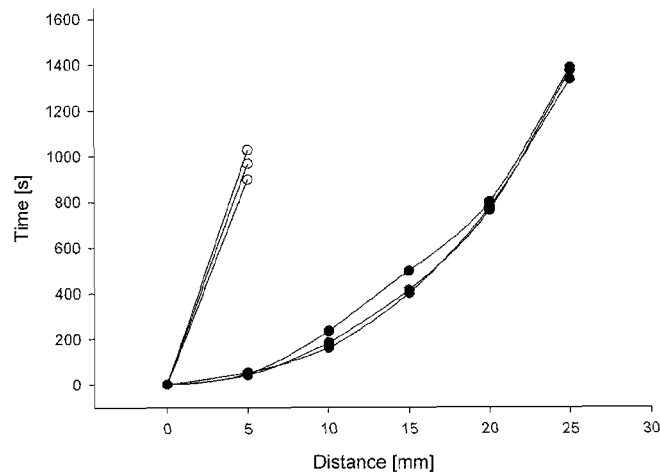
FIG. 10 shows the Correlation between time and distance travelled of the aqueous solution on substrates coated with $SiO_x$ modified according to (filled circles) $SiO_x1$, and (open circles) $SiO_x2$, (n=3).

To be applicable for lateral flow bioassays, the resulting surface modifications would need to allow reproducible, uniform filling of the micropillar structures in the device. Fill time experiments were performed in which the time taken for an aqueous dye solution to travel the narrow test channel area of the strip (see FIG. 1) was measured using video capture. The fill times of the $SiO_x1$ and $SiO_x2$ modifications are illustrated in FIG. 10. Although the modification by both protocols appeared to result in substrate modification of much increased surface activity, there was still a major difference in performance in the fill time experiments. In the case of the low power RF modification methodology ($SiO_x2$), the aqueous sample was unable to traverse the microchannel due to inadequate hydrophilicity. However, $SiO_x1$ resulted in uniform and reproducible filling characteristics in which it traversed the channel in 1366±27 s. It has been confirmed that surfaces modified according to $SiO_x1$ conditions, modified by more oxygen and by applying lower RF power to prevent the sample damage, could be used for the further development of lateral flow assays as they yielded sufficient wettability and stability to allow adequate fluidic performance characteristics.

Following deposition using the optimised $SiO_x$ layer methodology, 15 μL aliquots of 0.4% Triton X-100 in calibration plasma (Hemosil) were used as a lateral flow test solution. The fluid flow times were highly repeatable with an average flow time of 78 s (9% RSD); which is of paramount importance in aiming to create a $SiO_x$-coated platform potentially useful for the open lateral flow experiments, as coagulation monitoring assays or other biodiagnostic platforms.

Effect of $SiO_x$-Modified Substrates on Plasma Coagulation $SiO_x$-modified surfaces should, in principle, behave similar to glass, as they are essentially analogous materials. Glass surfaces and materials have been widely used for many years due to their many beneficial properties of chemical inertness, mechanical strength and processability. However, glass also suffers from many disadvantages including the means of processing and its brittleness. Combining polymers with glass-like surface properties is an excellent way to create hybrid materials with beneficial properties of both. One characteristic of glass that was identified was that it had the ability to accelerate the blood clotting process (Rapaport, S. I., Aas, K., Owren, P. A. (1955). Effect of Glass upon the Activity of the Various Plasma Clotting Factors, *Journal of Clinical Investigation,* 34 (1): 9; Sharma, C. P., Szycher, M. Blood Compatible Materials and Devices: Perspectives Towards the 21st Century, CRC Press, 1991). Indeed, the collection of blood in glass containers has to be protected from clotting by the addition of calcium chelators such as citrate or thrombin inhibitors such as heparin. It is believed that the highly negatively charged silicon dioxide surface resembles the exposed vasculature (collagen) following vascular injury and initiates the coagulation cascade via the intrinsic pathway. This phenomenon has been widely exploited in many blood coagulation assays where glass or other analogous silicates such as celite and kaolin are added to blood samples to accelerate clotting. Surfaces modified with a glass-like surface could thus be used to perform bioassays where the induction of blood coagulation via the intrinsic pathway is required such as the clotting time (CT)-type assays which include activated partial thromboplastin time (aPTT) and the activated clotting time (ACT).

Figure 11:
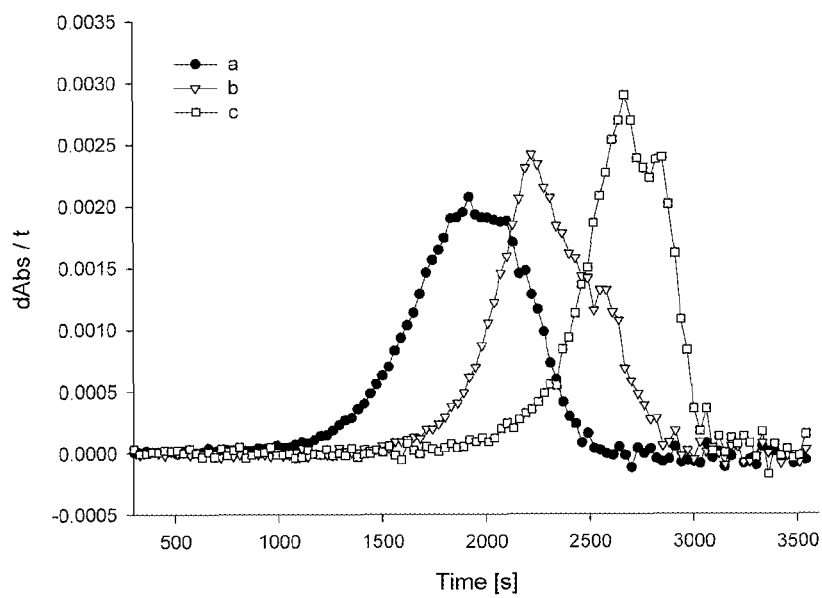
FIG. 11 is a chromogenic thrombin assay showing the effect of substrate on plasma clotting time (a) $SiO_x$-coated COP, (b) plain COP and (c) polystyrene control. A-Abs vs. t, B-dZAbs/dZt vs. t,), as follows: (a) $SiO_x$-coated COP (b) Blank, untreated COP (c) Blank polystyrene.

To evaluate the ability of the $SiO_x$-modified surface to accelerate the coagulation process, the substrate was introduced as the base of a microtitre plate well in which was placed citrated human plasma and a colorimetric thrombin substrate. These were allowed to incubate before the addition of $CaCl_2$ to allow coagulation to proceed. The thrombin curves generated are illustrated in FIGS. 10 and 11. In both the raw and differentiated data, it can be seen that the onset of clotting on a polystyrene microplate substrate was at about 2000 s. The unmodified COP was, itself, found to have some impact on CT, reducing the onset of clotting to some 1500 s. The $SiO_x$-modified substrate reduced this further to some 1000 s, or an approximate 50% reduction in CT; a significant impact.

Figure 12:
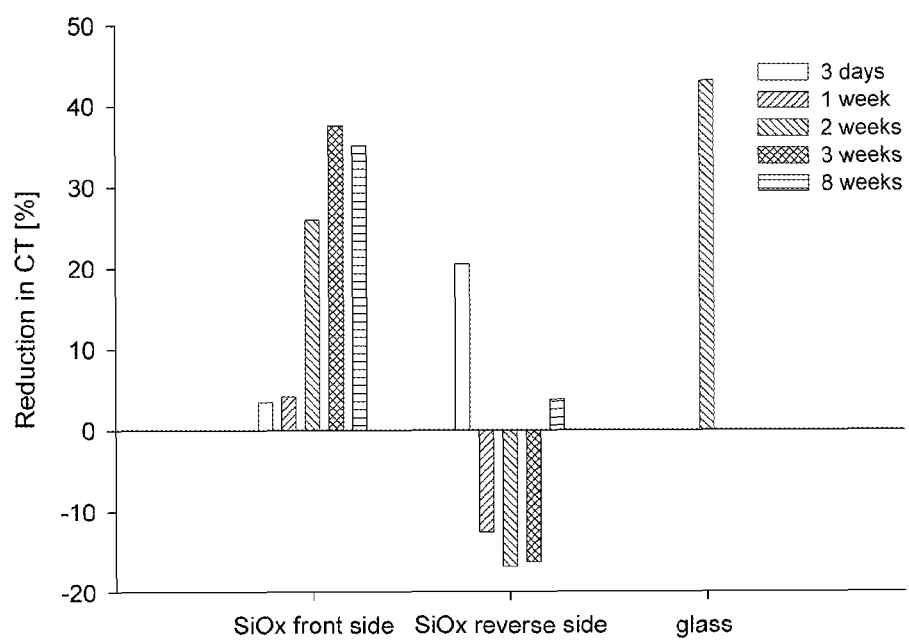
FIG. 12 shows Reduction in CT introduced by the front and the reverse side of $SiO_x$-coated COP substrates after 3 days, 1, 2, 3 and 8 weeks following $SiO_x$ modification comparing to glass positive control.

The stability of both the unmodified and the $SiO_x$-modified COP substrates to reduce the plasma CT was also investigated over several weeks and compared to glass (FIG. 12). Glass showed CT reduction value of 43.1±3.6%. The reverse side of the $SiO_x$-modified surface did effect some CT reduction initially. However, this effect became negligible or actually increased CTs after a week. The $SiO_x$-modified surface appeared to improve gradually over several weeks, reaching CT reduction values of some 35-37% after three to eight weeks, indicating additional as yet uncharacterized surface changes that appear to have enhanced the clotting process.

Conclusion

This Example shows a method for the modification of the cyclic polyolefin Zeonor® with a layer of $SiO_x$ using plasma-enhanced chemical vapour deposition following oxygen/argon plasma treatment. We found that the control of the gas content during deposition enhanced the quality and stability of the $SiO_x$ film.

The $SiO_x$ layer was extensively characterised using atomic force microscopy, Fourier transform infrared spectroscopy and attenuated total internal reflectance spectroscopy where the presence of a uniform $SiO_x$ film of 44 nm (0.05% RSD) was clearly identified.

We found that the $SiO_x$-modification resulted in a surface with enhanced wettability and excellent fluidic properties especially when combined with a hot-embossed micropillar capillary fill-based substrate. Additionally, we found that the $SiO_x$ surface also had the ability to accelerate the clotting of human plasma.

Specifically, we have illustrated the optimised modification of the novel cyclic polyolefin polymer Zeonor® with the plasma enhanced chemical vapour deposition of $SiO_x$ which has been extensively characterised by atomic force microscopy, spectroscopy and contact angle measurements. We have deposited the $SiO_x$ film on micropillar substrates to achieve highly wettable surfaces with uniform and predictable filling characteristics. A uniform, reproducible and stable film has been obtained. We have also illustrated that the $SiO_x$ shares glass-like properties and can be applied to the development of bioassays which utilise the properties of glass, but benefiting from the high processability of a polymer microfluidic device.

Example 2

Testing of Lateral Flow Assay Device
Fibrinogen Coating
Materials and Methods
B2.2 COP Amic® chips
blood coagulation reagent formulations as per Example 1—calcium chloride (BioData), fibrinogen (Sigma)
PT reagent (Dade Innovin)
aPTT reagent (aPTT-SP)
sample
Lateral Flow Experiments & Blood Clotting Protocol To bring about clotting, blood coagulation reagent formulations are added as dried reagents to the surface of the device and the sample being tested is allowed to flow over these reagents. Depending on the blood's ability to become clotted, the sample will move at different speeds along the device, going more slowly if clotting rapidly or come to a halt at an earlier point if clotting happens more quickly i) Testing Lateral Flow Tested solutions were applied at a volume of 20 ul, unless otherwise stated. The time for the fluid front to reach seven stages along the micropillar channel of B2.2 COP Amic chips was measured: 0, 5, 10, 15, 20, 23, 27 mm. Several parameters were measured including the type of coagulation reagent used, the deposition of calcium chloride (BioData) and the addition of fibrinogen (Sigma).

40 μl of a PT reagent (Dade Innovin) or aPTT reagent (aPTT-SP) were dried onto the surface of the device. Test and control were performed as follows to either allow or prevent clotting:

TEST: plasma+25 mM $CaCl_2$ (1:1) pre-warmed at 37° C. for 3 min.

CONTROL: plasma+$NH_4Cl$ (1:1) pre-warmed at 37° C. for 3 min.

ii) The Effect of Fibrinogen

The effect of fibrinogen was initially investigated by depositing 20 μl of 50 mg/mL fibrinogen and drying onto the surface. The following test and control samples were employed TEST 20 μl: plasma+25 mM $CaCl_2$ (1:1) pre-warmed at 37° C. for 7 min.

TEST 30 μl: plasma+25 mM $CaCl_2$ (1:1) pre-warmed at 37° C. for 7 min.

CONTROL 20 μl: plasma+25 mM $NH_4Cl$ (1:1) pre-warmed at 37° C. for 7 min.

CONTROL 30 μl: plasma+25 mM $NH_4Cl$ (1:1) pre-warmed at 37° C. for 7 min.

iii) Combined Effect of Fibrinogen and/or Calcium Chloride

Further tests were performed to illustrate the combined effect of depositing fibrinogen and calcium chloride or calcium chloride alone, with samples that had premixed coagulation reagents added in the form of PT and aPTT. In this case 20 μl of 50 mg/mL fibrinogen +25 mM $CaCl_2$ (1:1) was deposited and dried over night. A control surface was prepared by drying over night 10 μl of 25 mM $CaCl_2$.

Test solutions were as follows:
Plasma+PT (Dade Innovin) (1:1) applied immediately after mixing
Plasma+aPTT (aPTT-SP) (1:1) pre-warmed at 37° C. for 5 min.
Plasma+PBS (1:1) warmed to 37° C. (plasma viscosity control).
Plasma+25 mM $CaCl_2$ (1:1) pre-warmed at 37° C. for 7 min (unaccelerated clotting control).

iv) Externally Mixed Coagulation Reagents on Bare COP Chips

More detailed experiments were performed which looked at the effect of externally mixed coagulation reagents on Bare COP chips with no chemistries deposited in the channels. The following samples were used.

TEST: Plasma+PT reagent (including $CaCl_2$) (Dade Innovin) 1:1 with an addition of Triton X-100

CONTROL: plasma+aPTT reagent (no $CaCl_2$) (aPTT-SP) 1:1 with an addition of Triton X-100

Immediately after mixing, an aliquot of 20 μl was applied to the sample area with no pre-incubation step.

v) Fibrinogen Concentration & Filling Profiles

More detailed studies were also performed on the impact of fibrinogen concentration. Several concentrations of fibrinogen were prepared. 20 μl of each was applied to the channel and left to evaporate over night at RT.

Table 1 shows the concentrations that were used and the corresponding amount of fibrinogen dried to the surface.

TABLE 1

Concentrations and masses of fibrinogen deposited in the channels.

| Fibrinogen concentration used [mg/mL] | Amount of fibrinogen [mg] |
|---|---|
| 50 | 1 |
| 20 | 0.4 |
| 10 | 0.2 |
| 5 | 0.1 |
| 2.5 | 0.05 |
| 1.25 | 0.025 |

TEST: plasma+PT reagent (clotting) (Dade Innovin) 1:1
CONTROL: plasma+aPTT reagent (non-clotting) (aPTT-SP) 1:1

Fibrinogen at conc. 50 mg/mL was mixed with twice concentrated PT reagent (Recombiplastin) 1:1. The 1:1 ratio results in twice diluted fibrinogen and Recombiplastin at standard concentration as suggested by manufacturer. Triton X-100 was added at the conc. 0.125% and 20 ul or 40 ul of this solution was applied to the surface and dried over night at RT.

Recombiplastin has been chosen over Dade Innovin, as the latter creates "crystals" in a dried form, which have impact on flow properties.

40 ul of deposited solution contains 1 mg of fibrinogen, and 20 ul contains 0.5 mg of fibrinogen.

TEST 1: plasma+25 mM CaCl2 1:1 pre-warmed at 37° C. for 7 min.
TEST 2: plasma+25 mM NH4Cl 1:1 at 37° C.
CONTROL: 25 mM CaCl2+Tris-HCl 1:1 at 37° C.

In Test 2 there is no Ca to overcome the effect of citrate in plasma, however some clotting may occurred once the sample is in contact with the surface with dried PT reagent that contains Ca.

Results

The following results illustrate the use of the lateral flow assay system to be used as a platform for blood coagulation assays.

i) Testing Lateral Flow

Figure 13A:
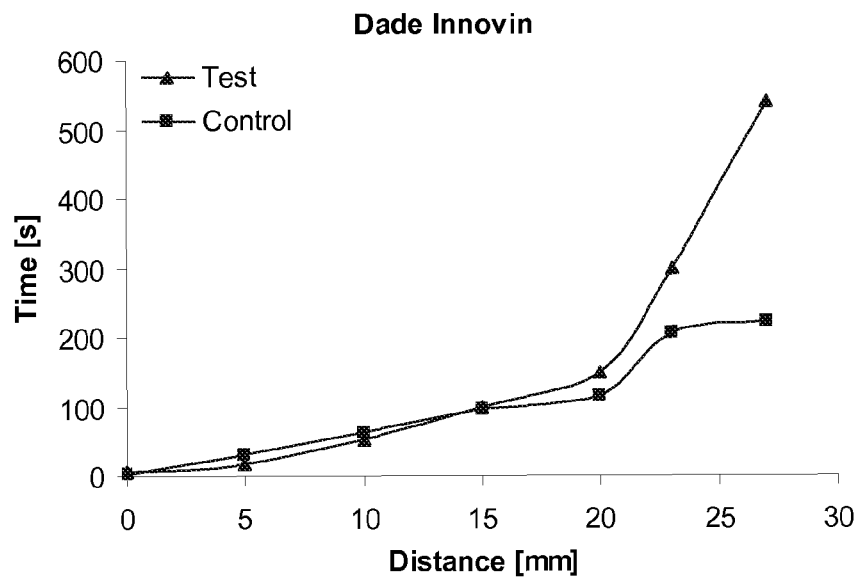
FIGS. 13a and 13b shows the results of PT (13a—40 µl of Dade Innovin) and aPPT(13b—40 µl of aPPT-SP) lateral flow coagulation assay tests.
Figure 13B:
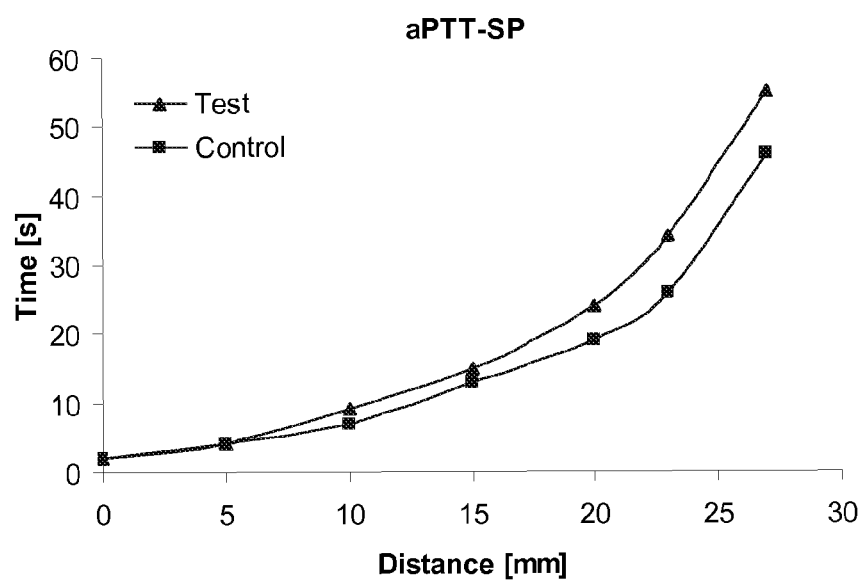
Figure 14:
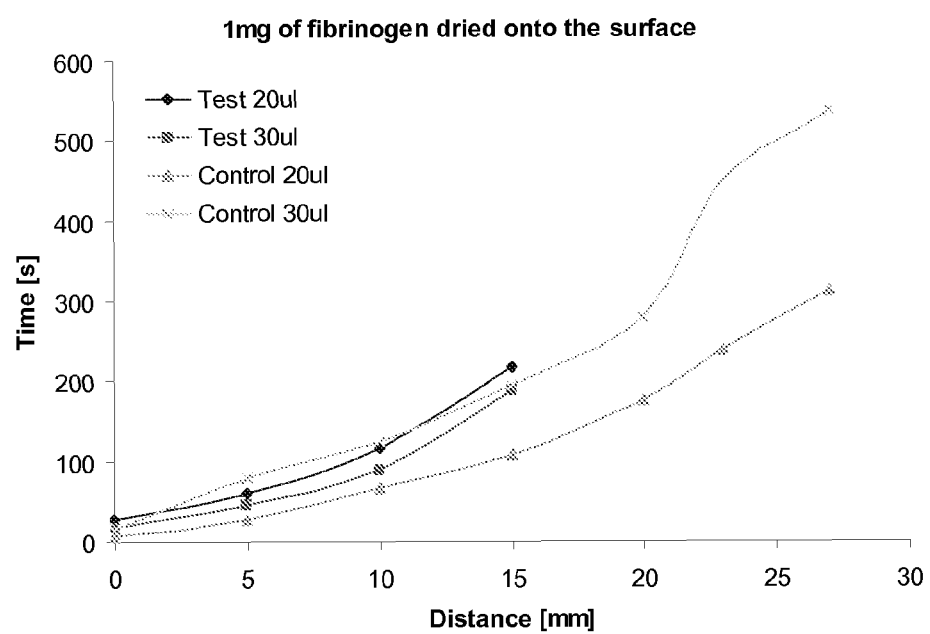
FIG. 14 shows the effect of fibrinogen on the lateral flow assay.

As shown in FIGS. 13a and 13b for both PT and aPTT, the time taken to traverse the device was elevated for clotting test samples over non-clotting samples ii) The Effect of Fibrinogen FIG. 14 illustrates the impact of using fibrinogen deposited on the test channel and the effect of sample volume. At 20 µl, there was a marked difference in the travel time for test and control samples. This difference in travel time was less pronounced for 30 µl samples. However, the flow of both test samples was arrested at 15 mm. The difference in applied sample volume results in a 'push' effect from the sample reservoir which causes the control to travel more quickly. However, this affect could be counteracted with reduction in applied sample volume.

iIi) Combined Effect of Fibrinogen and/or Calcium Chloride

Figure 15:
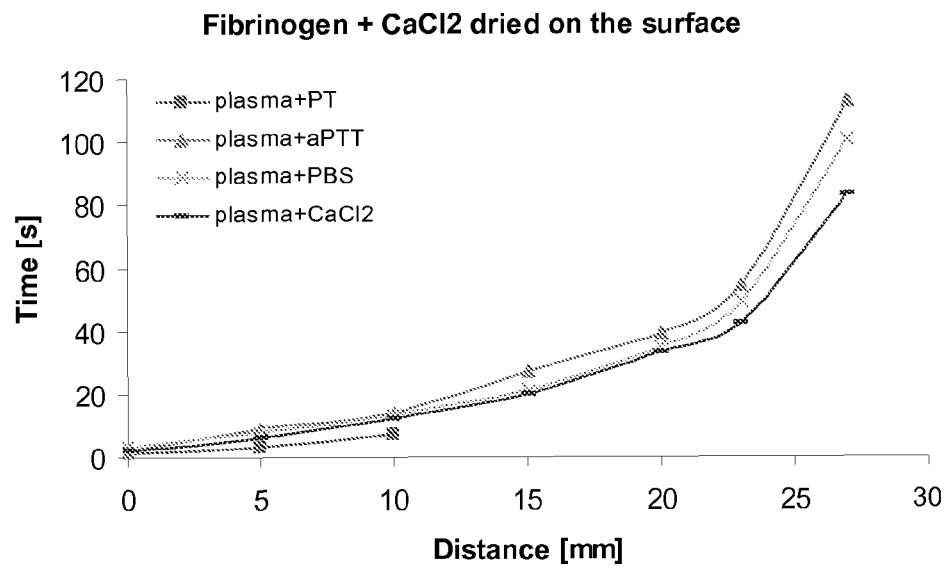
FIG. 15 and FIG. 16 show the combined effects of fibrinogen and/or calcium chloride in the lateral flow immunoassay.
Figure 16:
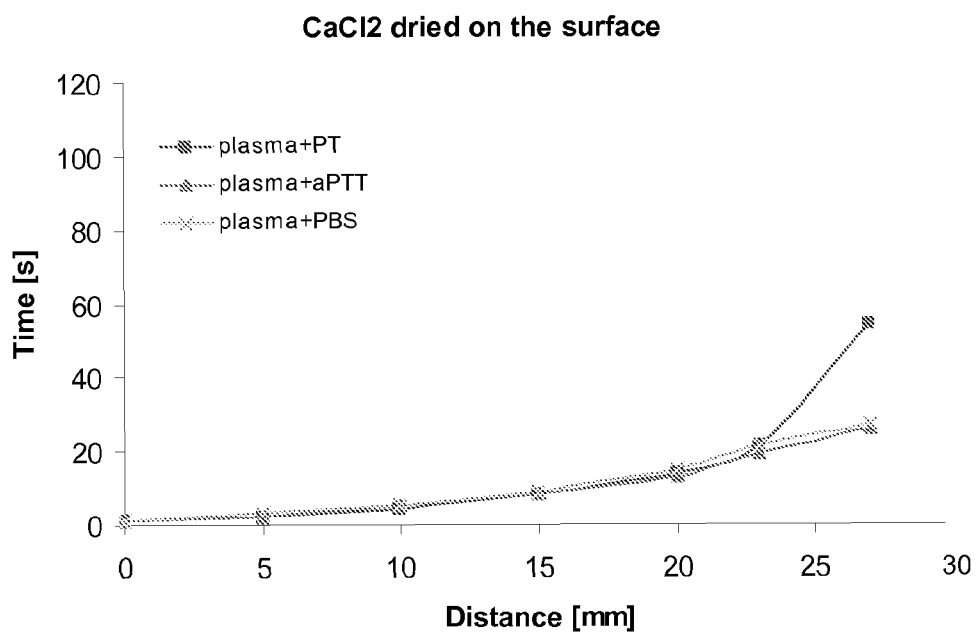

FIG. 15 and FIG. 16 show that the speed of flow was much slower on the fibrinogen-coated devices than on those with calcium chloride alone. However, this occurred for viscosity controls also and probably relates to the viscosity and interfacial properties of the deposited fibrinogen. On both surfaces, the plasma PT was either slowed (on $CaCl_2$) or arrested prematurely (fibrinogen and $CaCl_2$). The velocity of plasma aPTT was also reduced compared to controls on fibrinogen and calcium chloride.

iii) Externally Mixed Coagulation Reagents on Bare COP Chips

Figure 17:
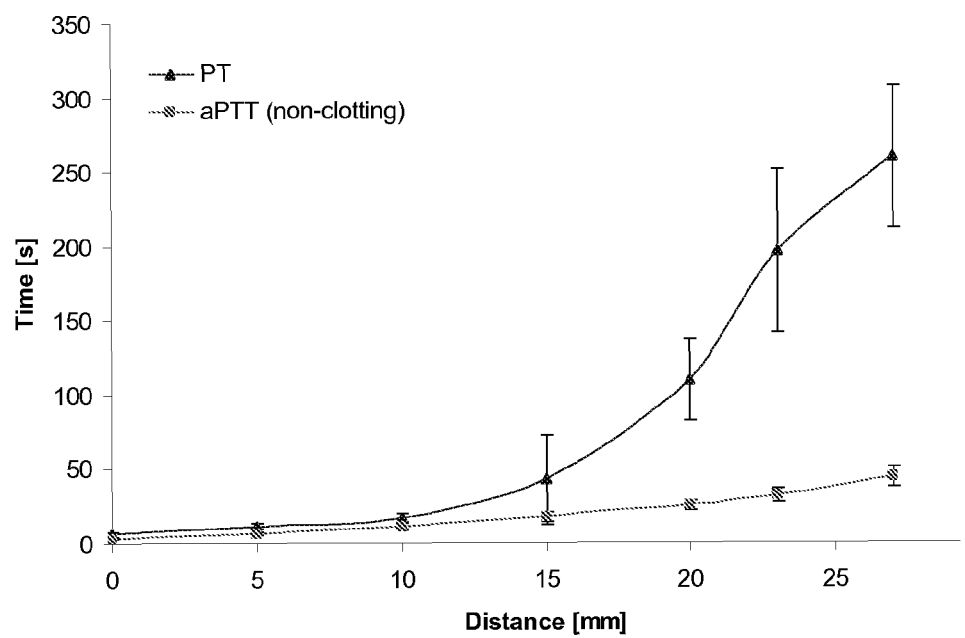
FIG. 17 shows the effects of externally mixed coagulation reagents on bare cyclo-olefin polymer (COP) chips.

More detailed experiments were performed which looked at the effect of externally mixed coagulation reagents on Bare COP chips with no chemistries deposited in the channels. Plasma with Dade Innovin started clotting immediately as this PT reagent contains calcium. The control does not clot, as there is no calcium in aPTT-SP to overcome the effect of citrate in plasma. The aPTT reagent was used as a control to mimic the viscosity and behaviour of plasma mixed with activator. Both test and control solutions reached the end of the channel (27 mm). However, the test solution was much slower especially towards the end of the channel, and the formed clot could be seen in the sample zone, see FIG. 17 (n=6).

iv) Fibrinogen Concentration & Filling Profiles

More detailed studies were also performed on the impact of fibrinogen concentration. Several concentrations of fibrinogen were prepared. 20 µl of each was applied to the channel and left to evaporate over night at RT.

Table 1 shows the concentrations that were used and the corresponding amount of fibrinogen dried to the surface.

TABLE 1

Concentrations and masses of fibrinogen deposited in the channels.

| Fibrinogen concentration used [mg/mL] | Amount of fibrinogen [mg] |
|---|---|
| 50 | 1 |
| 20 | 0.4 |
| 10 | 0.2 |
| 5 | 0.1 |
| 2.5 | 0.05 |
| 1.25 | 0.025 |

TEST: plasma+PT reagent (clotting) (Dade Innovin) 1:1
CONTROL: plasma+aPTT reagent (non-clotting) (aPTT-SP) 1:1

Figure 18:
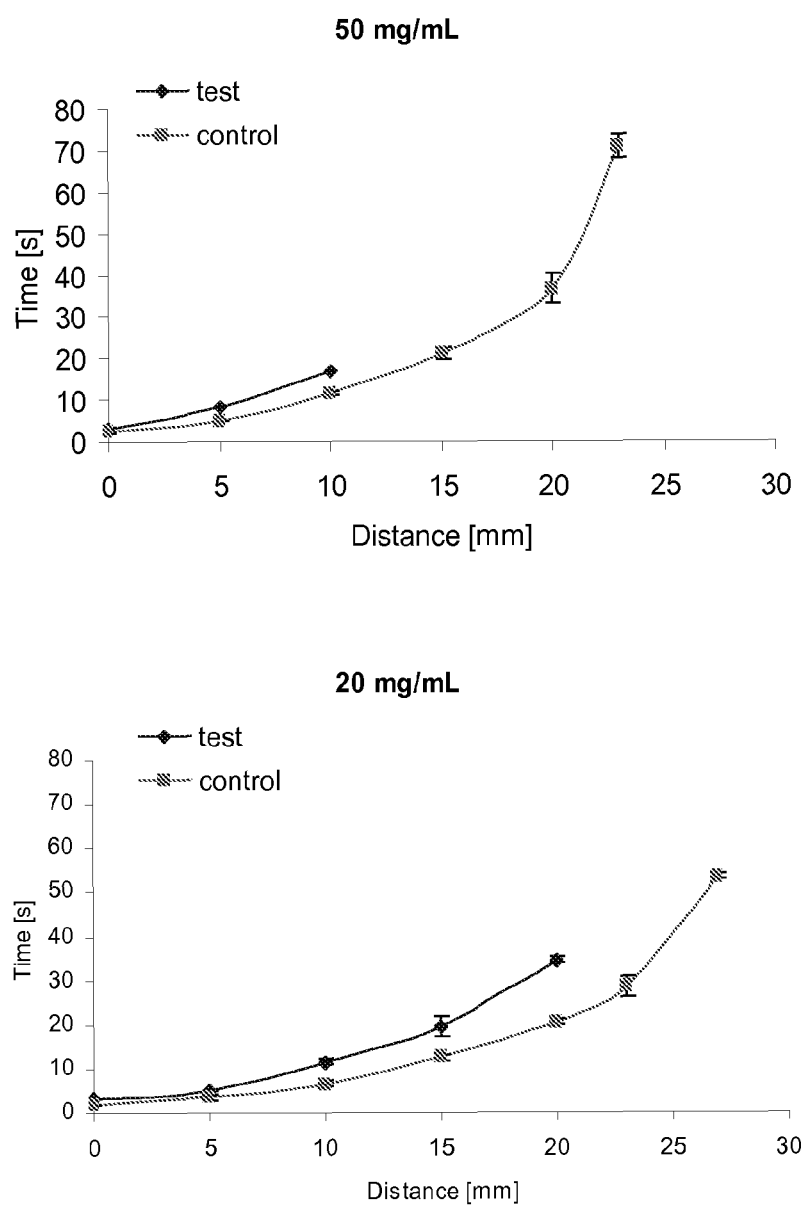
FIG. 18 shows the filling profiles with varying amounts of fibrinogen.
Figure 18:
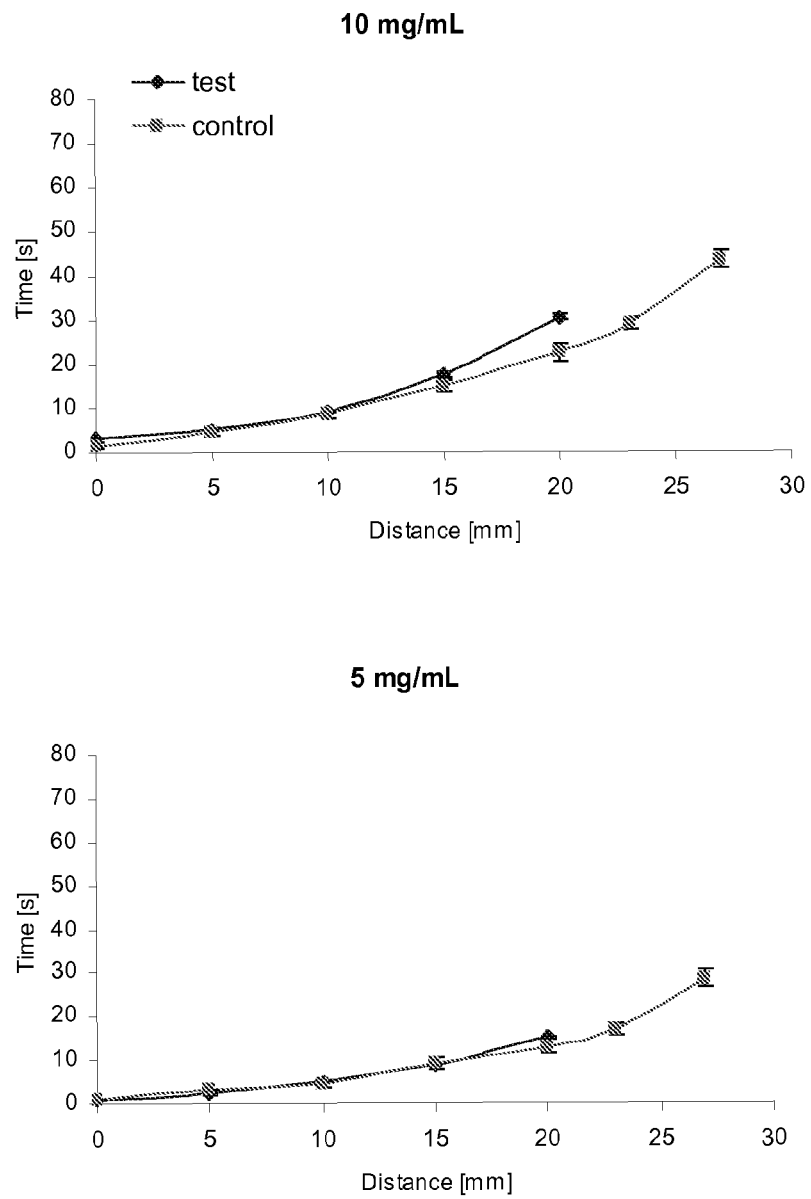
Figure 18:
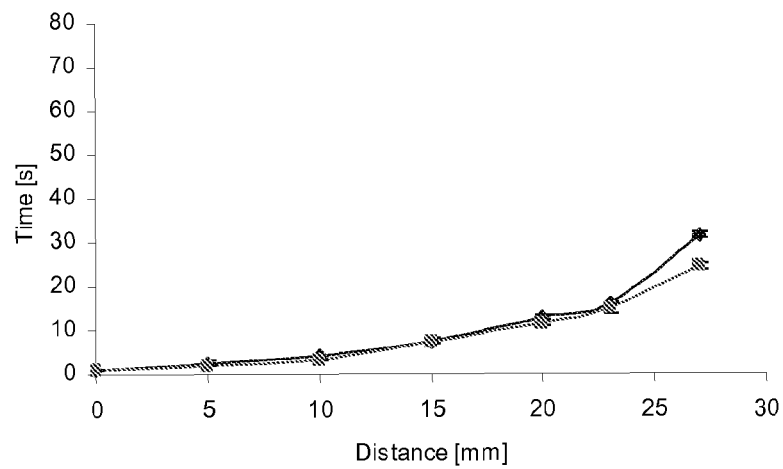
Figure 18:
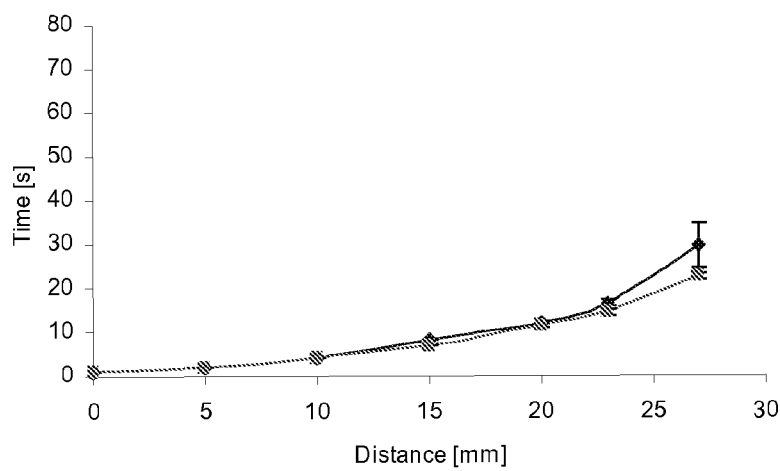

FIG. 18 shows the filling profiles of test and control solutions (n=2) on the surfaces with different amounts of fibrinogen. In the case of 50 mg/mL (1 mg of fibrinogen) the test was travelling slower than control and both control and test solutions were stopped before they had reached the end of the channel; test solution stopped at 13 mm while the control solution stopped at 23-27 mm (the area with different structure of micropillars). For lower fibrinogen concentrations control solutions were faster but reached the end of the channel. On the 20 mg/mL surface (0.4 mg of fibrinogen), the test solution was travelling slower than control and stopped in the area between 23-27 mm. On the surface with 10 mg/mL (0.2 mg of fibrinogen) the test was again travelled slower than control and was stopped in 23-27 mm with only a thin, almost invisible serum layer still slowly moving, but did not reach the end. The filling on 5 mg/mL (0.1 mg of fibrinogen) was similar to 10 mg/mL, but the filling times of test and control were not much different and the thin layer of liquid serum reached the end. In the cases of 2.5 mg/mL and 1.25 mg/mL (0.05 mg and 0.025 mg of fibrinogen) the difference in travel time between test and control was only noticable in the last step of the channel. To sum up, the more fibrinogen deposited in the channels, the slower the flow for both test and control solutions.

Figure 19:
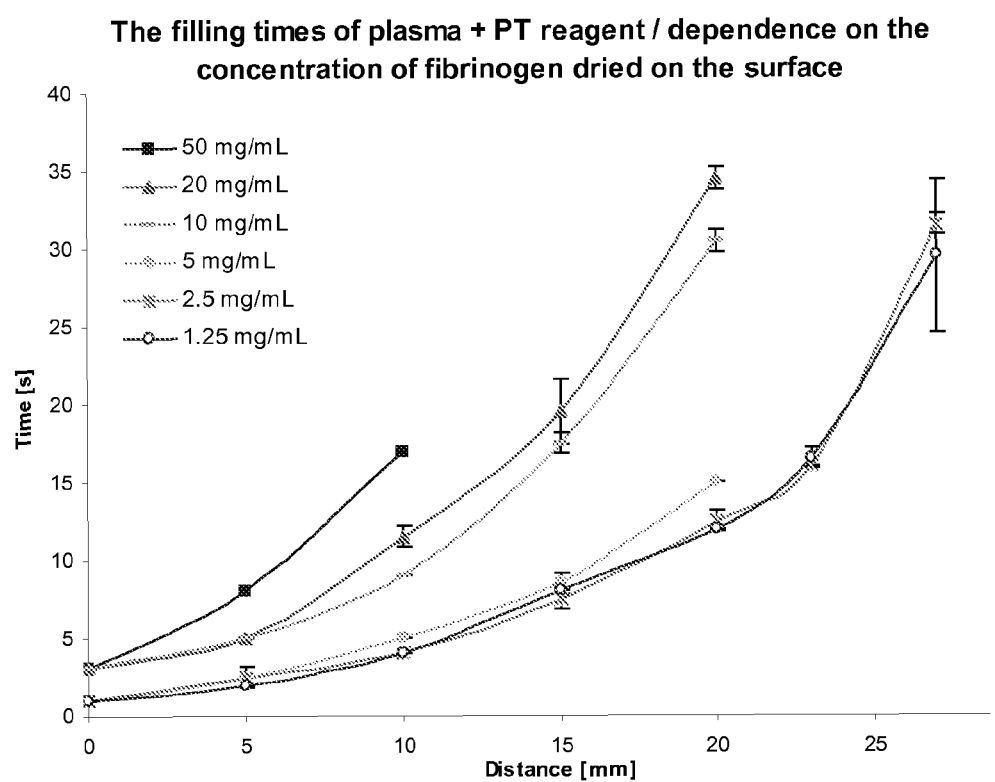
FIG. 19 shows a comparison of the filling profiles for various test solutions.

Filling profiles for test solutions are compared in FIG. 19.

Figure 20:
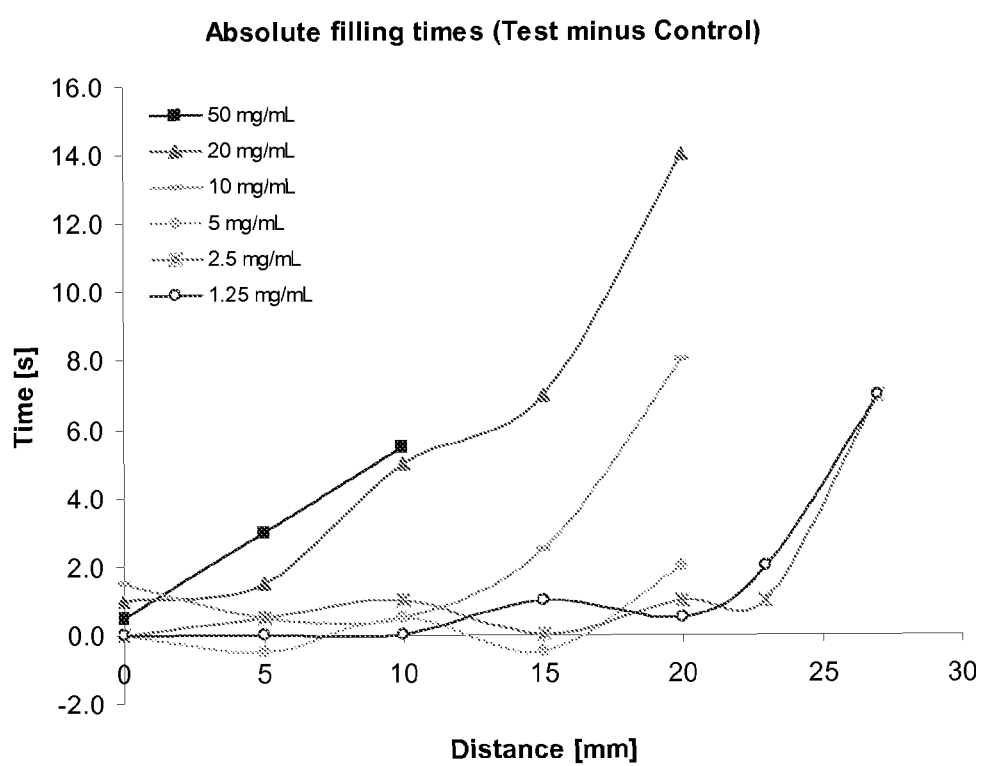
FIG. 20 shows the filling profiles with varying amounts of fibrinogen.

To obtain absolute filling time values the filling times for controls were subtracted from the test filling times, to eliminate the impact of differences in surface tension, hydrophobicity etc (i.e, differences due to the amount of dried fibrinogen) on the flow time (FIG. 20).

As shown, the surface had a huge impact on the filling properties, but is not the only factor determining the fill time. As can be seen from the graph with absolute filling time values there is a correlation between the amount of fibrinogen deposited and time/distance travelled. The lower the fibrinogen concentration, the slower clotting/fibrin formation process and quicker flow.

Figure 21A:
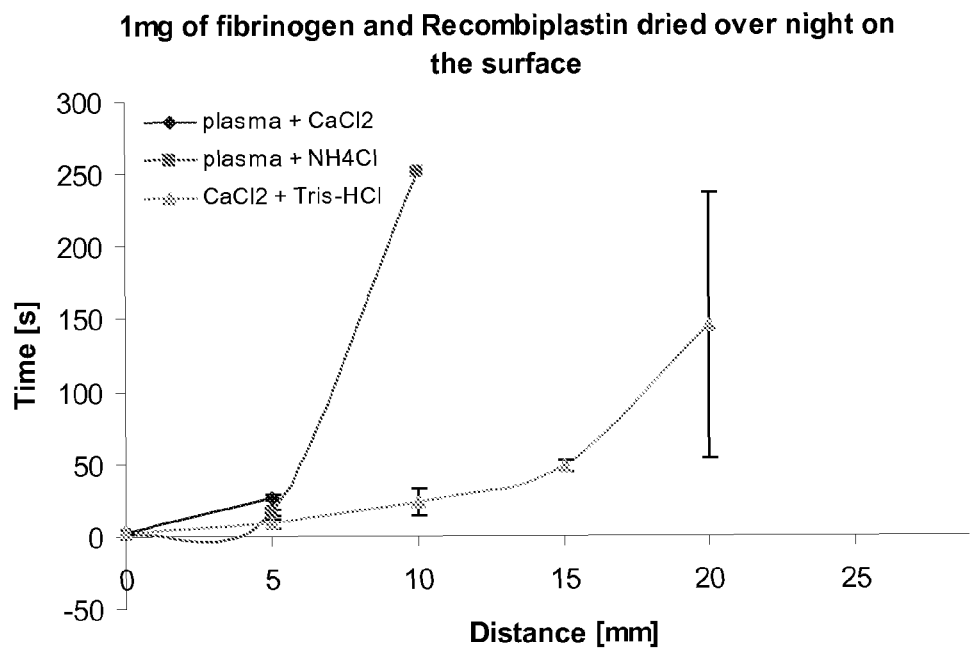
FIG. 21a and FIG. 21b shows the effect of Ca on filling profiles.
Figure 21B:
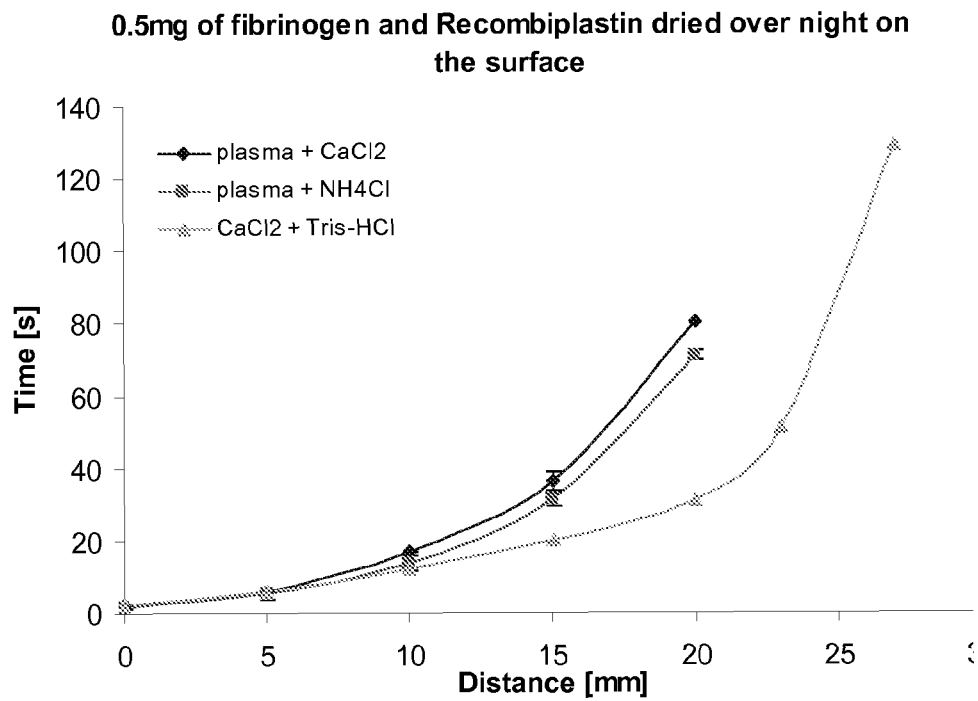
Figure 22:
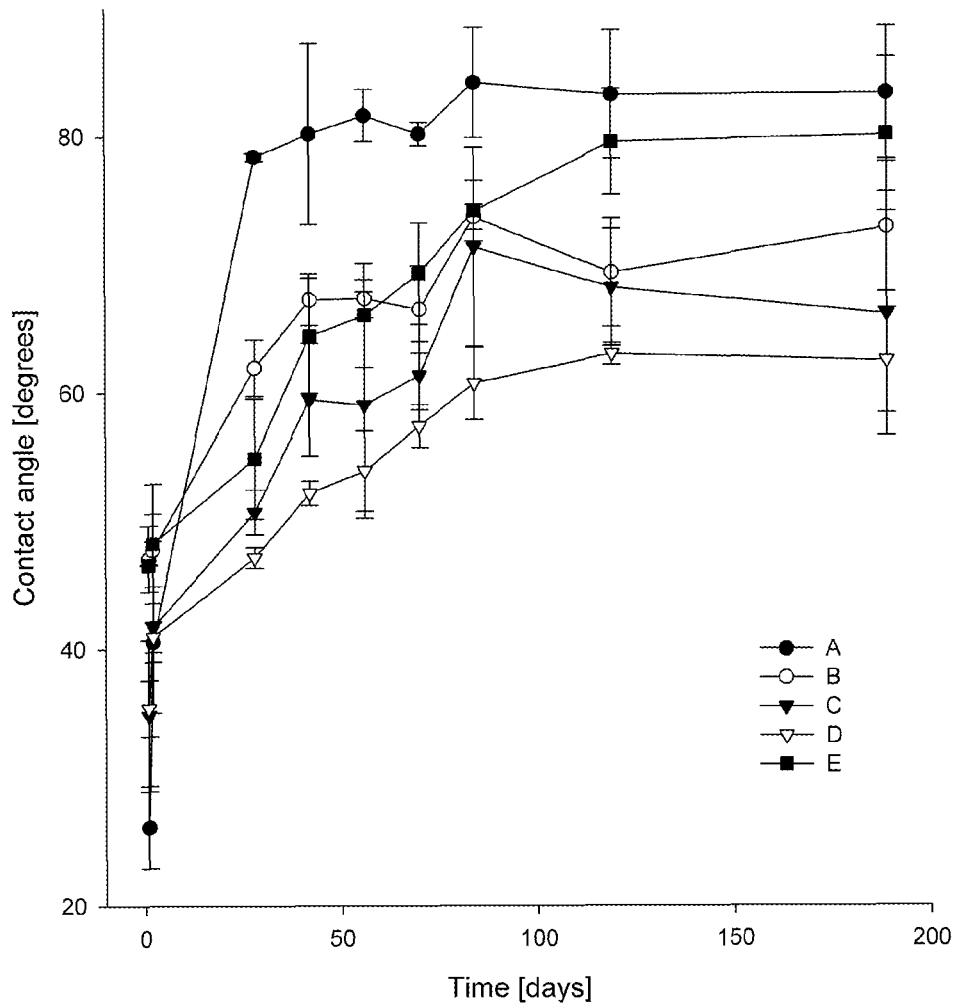
FIGS. 22 to 26 compares the use of different coating materials on a COP-based microfluidic platform.
Figure 23:
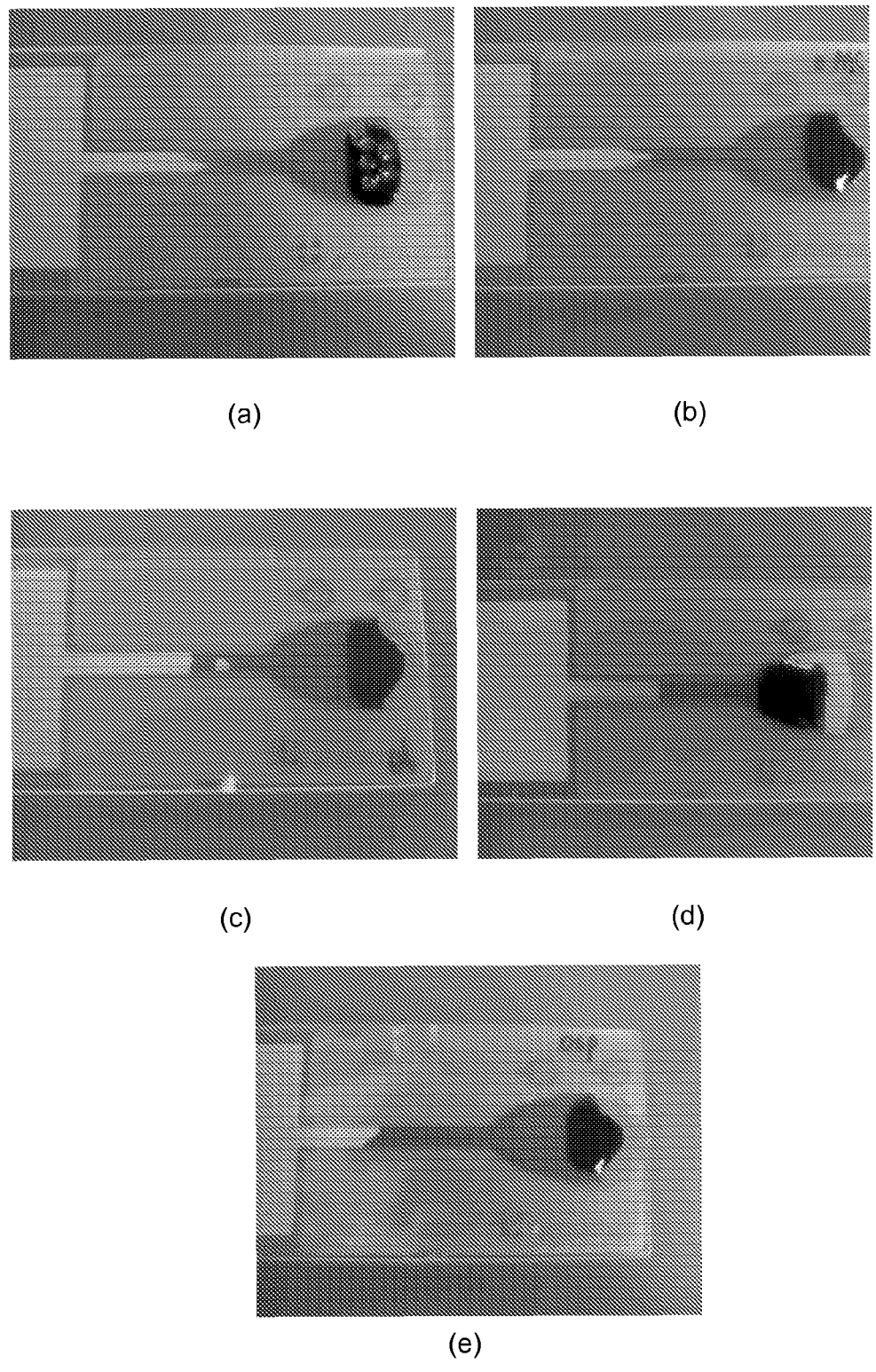

Summary of Time/Distance Travelled:
50 mg/mL—stopped at 13 mm
20 mg/mL—stopped at 23-27 mm
10 mg/mL—only thin layer of liquid travelling between 23-27 mm; did not reach the end
5 mg/mL—only thin layer of liquid serum travelling between 23-27 mm; did reach the end
2.5 mg/mL—reached the end
1.25 mg/mL—reached the end FIG. 21a and FIG. 21b show the effect of calcium chloride.addition on filling profiles Example 3

Polyelectrolyte Modification
Materials and Method
A COP-based microfluidic platform substrate, 4Castchip® (Åmic AB, Sweden) was used as the substrate.

The polyelectrolyte (PE) modification method used in this example consisted of two steps, oxygen plasma treatment and dip coating with polyelectrolyte.

Oxygen plasma treatment was carried out in a radio frequency (RF) PECVD reactor with base pressure of a deposition chamber was ≤30 mTorr. 50 standard cubic centimetres per minute (SCCM) of oxygen was applied under a RF power of 250 W for 3 min.

PE treatment was carried out immediately after the oxygen plasma process was completed, as the effect of this treatment is not stable over time, and the created functional groups tend to degrade. Samples were dipped in 2 mg/mL PEI (polyethylenimine) in Millipore water solution for 10 minutes, afterwards washed with water, and dipped in 2 mg/mL PAC (poly(acrylic acid)) in water solution for 10 minutes and washed again with water. Dipping in PEI and then in PAC was repeated once again. Finally, all the samples were washed with water and dried in a stream of dry air. The process was carried out at room temperature (RT).

Results and Conclusion
FIGS. 22 to 26 show the results for PE treatment.

Example 4

Comparative Data-Evaluation of a Range of Surface Modifications for the Enhancement of Lateral Flow Assays on Cyclo-Olefin Polymer Microfluidic Devices Materials and Methods
A COP-based microfluidic platform substrate, 4Castchip® (Åmic AB, Sweden), was modified by the following treatments:
oxygen plasma treatment alone;
PAC coating alone;
polyelectrolyte treatment (as described in Example 3);
$SiO_x$ deposition alone (as described in Example 1);
$SiO_x$-coated polymer treated with polyelectrolyte.

Results
The different surface coatings were characterized by several techniques and the results are shown in Examples 22 to 26.

The surface modifications had an impact on the fluid dynamics of the substrate. The SiOx coating in particular, brought about enhancements in hydrophilicity as well as changes in surface roughness and uniformity yielding rapid and reproducible flow of both aqueous buffer solutions and human plasma.

Figure 24:
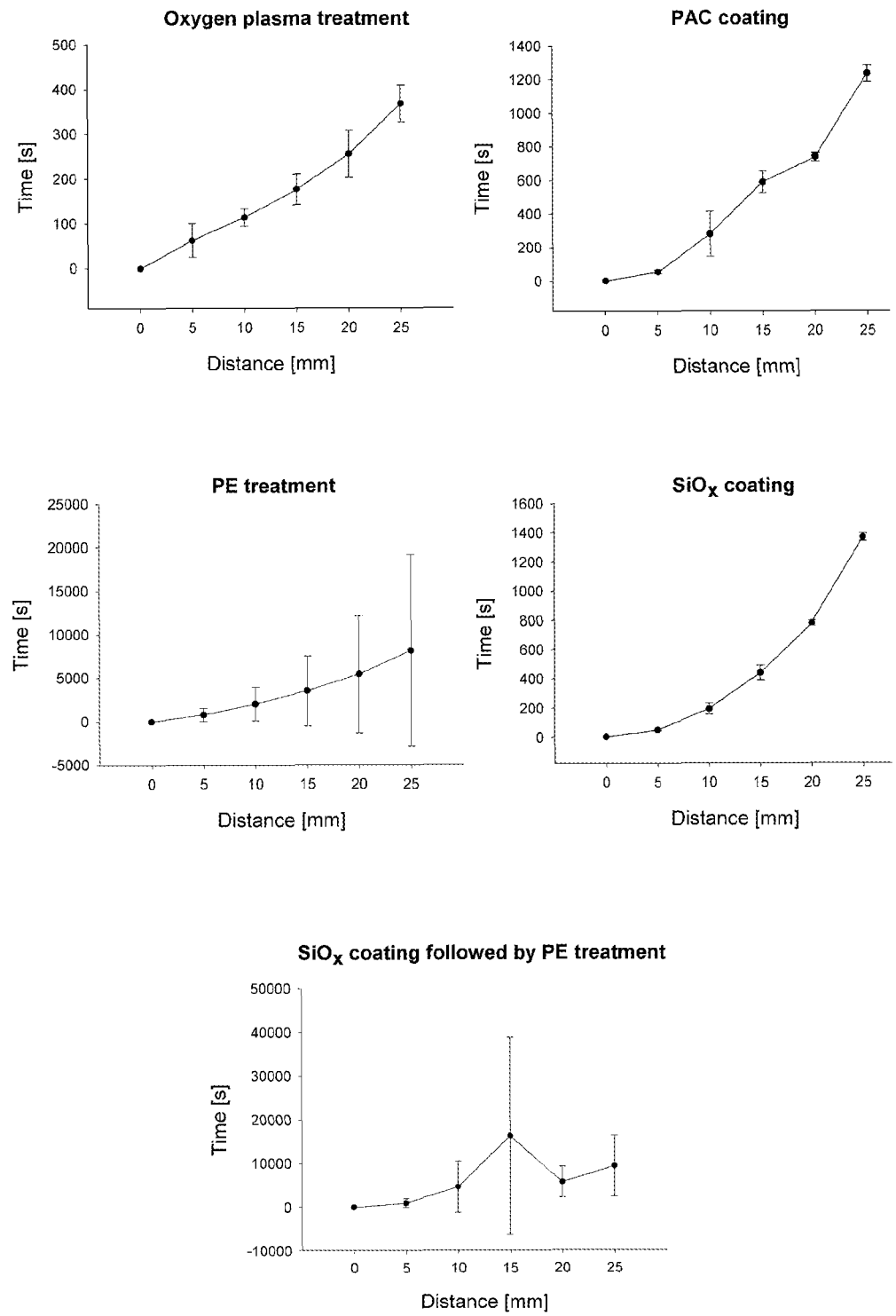
Figure 25:
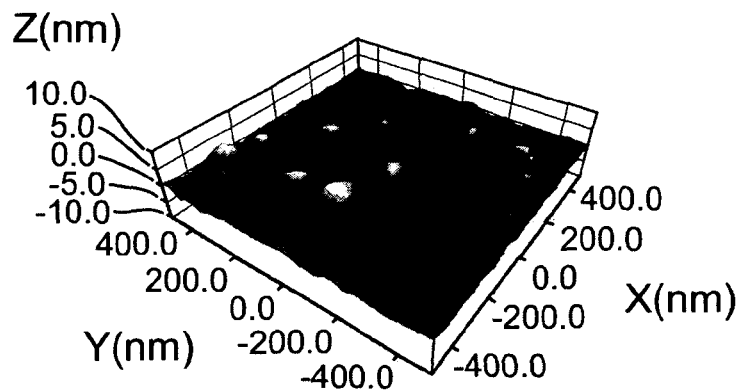
Figure 25:
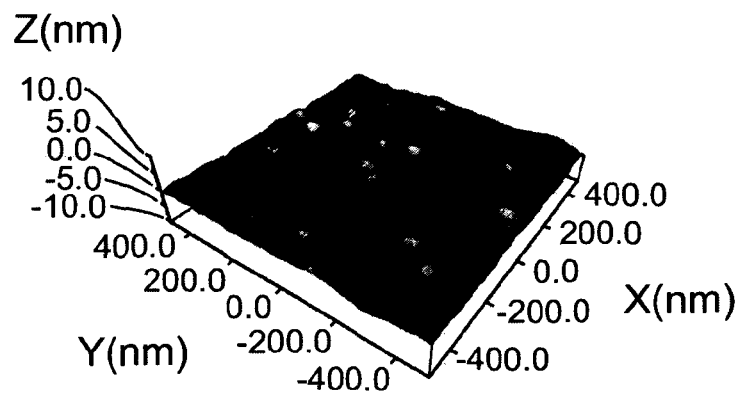
Figure 25:
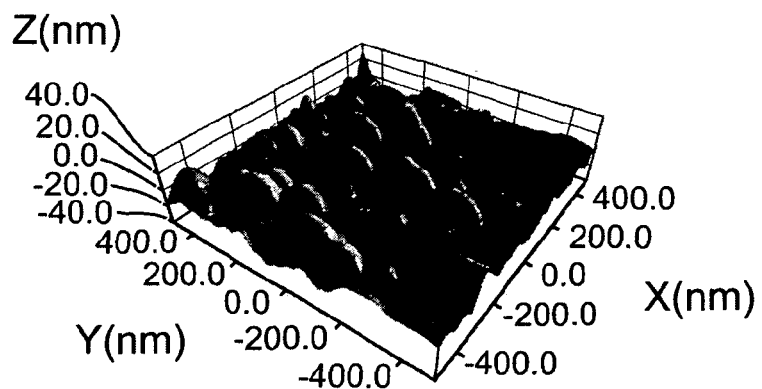
Figure 26:
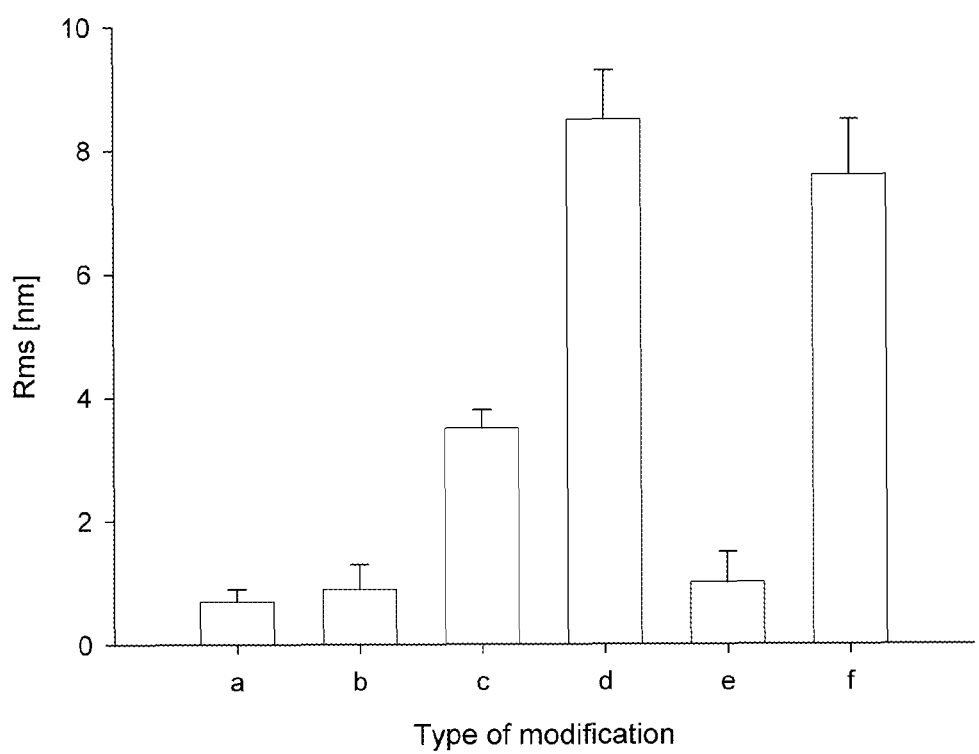

Conclusion
Cyclo-Olefin Polymer (COP) substrates such as the 4Castchip® (Åmic AB, Sweden) may be modified by several techniques. However, significant differences in the surface wettability, roughness and the liquid flow properties have been noted. The SiOx coating in particular was considered to be the most stable surface modification that imparts hydrophilicity, yielding rapid, reproducible flow on relatively smooth surface. The polyelectrolyte treatment was also found to give good results (FIG. 24).

Example 5

Figure 1C:
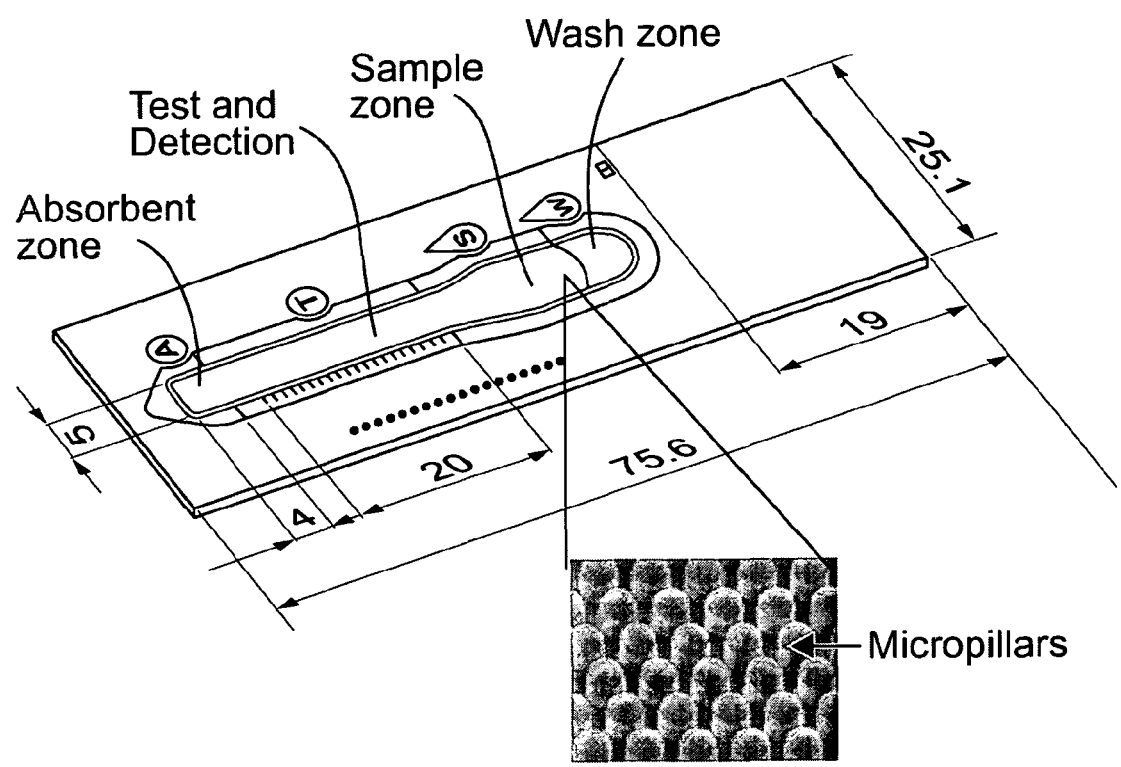
FIG. 1c shows a further graphical representation of the Amic® B 2.2 micropillar lateral flow device employed in the examples. Dimensions are shown in mm. The channel was approximately 27 mm long and 5 mm wide. The test channel possessed hot-embossed micropillar structure, as shown in the magnified inset.

Thrombin Coating
General Materials & Method
The 4Castchip®, model B 2.2, was used as a platform for the development of an open lateral flow device for fibrinogen level determination. Chips were modified with a hot embossed micropillar structure and supplied by Åmic BV (Uppsala, Sweden) (FIG. 1c). The height of the micropillars was 65-70 μm, top diameter was ca 50 μm, bottom diameter was ca 70 μm, the distance between the centres of the pillars in a row was 85 μm and the distance between the centres of the pillars in a column was 185 μm.

Unless otherwise stated, a mixture of bovine thrombin (Sigma or Hyphen Biomed) and Triton X-100 (Sigma) was drop-cast onto the channel within the test platform, left to dry for approximately 1 hour under ambient conditions (various concentrations of thrombin and Triton X-100 were tested; thrombin enzymatic activity is given in NIH units per mL, (U/mL) of an aqueous-based solution). Ready-to-use test chips were stored at 4° C. Testing was performed by application of approximately 15 μL plasma or whole blood (prewarmed to 37° C.) onto the application/sample zone and the distance traversed along the test channel was monitored. All measurements were carried out at 37° C.

Various assays were carried out as follows.
i) TCT Assay for Heparin Concentration Determination
The use of purified thrombin to directly induce a clot formation and subsequent viscosity change was utilised in the following clotting monitoring assay development. Supplying purified thrombin was believed to allow bypassing the cascade of coagulation factors activation and the thrombin generation positive feedback.

Thrombin clotting time (TCT) reagent (Hyphen BioMed) composed of an optimised mixture of purified bovine thrombin (1 U/mL) and calcium has been used for the determination of the effect of anticoagulants in plasma such as heparin. TCT reagent is sensitive to low concentrations of heparin in plasma from 0.05 to 0.1 U/mL of UFH with normal TCT of 15-25 s according to the manufacturer. 10 μL of TCT reagent supplemented with 0.1% (v/v) Triton X-100 was drop-coated onto the test platforms and dried. 15 μL aliquots of normal plasma and plasmas spiked with 0.2, 0.4 and 2 U/mL of heparin were applied to the test strip and the sample travel time and distance were measured. Regardless of the heparin concentration, all samples travelled 9-12 mm in approx. 30 (n=4). There was no significant difference in the distance travelled or time taken for normal or heparinised samples, which suggests that the system in this form was not suitable for heparin monitoring. Similar fill times and distances travelled obtained for the normal clotting and heparinised plasma could indicate that the flow pattern was determined by the surface properties (lack of surface uniformity, high density of an immobilised protein etc.) rather than by a clotting ability. An alternative optimised surface coating however could possibly allow distinguishing between samples of different clotting status determined as the TCT.

Figure 34:
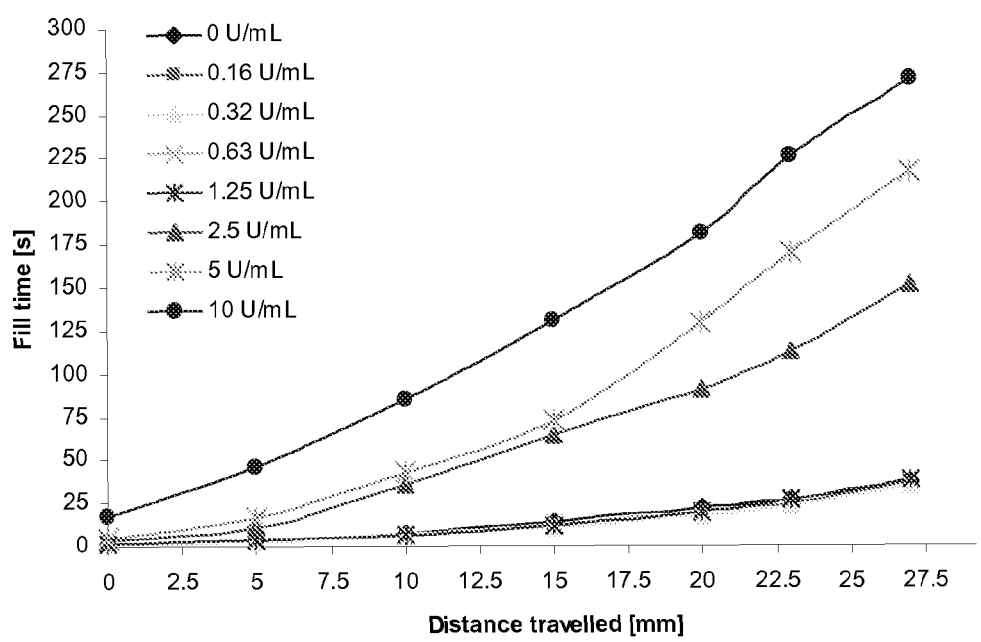
FIG. 34 shows the fill times recorded at 0, 5, 10, 15, 20, 23 and 27 mm for a plasma sample travelling through the channels coated with 0 to 10 U/mL of purified thrombin.

More detailed study was carried out where plasma flow rate was monitored in the channels coated with varying thrombin concentrations between 0 and 10 U/mL. Control channel contained 25 mM $CaCl_2$ (10 μL). The time taken by 15 μL of citrated plasma sample to reach each of seven steps along the channel: 0, 5, 10, 15, 20, 23 and 27 mm was recorded (FIG. 34).

The correlations between time and distance travelled by a citrated plasma sample exhibited significant differences depending on the concentration of the surface-immobilised thrombin. Channels coated with 1.25 U/mL or less thrombin were filled rapidly in 34 to 38 s and no difference in the time or distance travelled was observed. Particular steps along the channels: 0, 5, 10, 15, 20 and 23 mm were reached in approx. 1, 3, 6, 12, 19, 25 s, respectively. Increased fill times were observed with increasing thrombin concentration at 2.5 U/mL and higher. It took 151, 216 and 270 s for a plasma sample to fill the channel with 2.5, 5 and 10 U/mL of thrombin, respectively. The times required for a sample to reach particular steps along the channel were also increased for the concentrations of 2.5 U/mL and higher. High thrombin concentrations allowed rapid clotting and therefore, caused a notable change in a bulk sample viscosity, which resulted in the prolonged fill times. It could be speculated that not only was the onset of clotting different with the increased thrombin concentrations, but also the structure and strength of the fibrin mesh was different, which had a major impact on the plasma sample flow characteristics. The fibrin organisation is also dependent on the availability of its precursor, fibrinogen which is a direct target for the thrombin.

ii) TCT Assay for Fibrinogen Determination

TCT can also be used for the determination of fibrinogen concentration. Fibrinogen is known to be the main plasma protein, being at a concentration between 2-4 g/L and is a major determinant of plasma and whole blood viscosity and is the direct precursor of insoluble fibrin monomers forming fibrin mesh. Thrombin present at high concentration acts rapidly, cleaving available fibrinogen and allows the formation of a dense, stiff clot composed of thin fibrin fibres. Such a clot formation might be suitable to bringing about bulk changes in viscosity, and this flow times and travel distances. Therefore, the following work focused on utilising the thrombin-modified platforms for the measurement fibrinogen content in plasma and whole blood. The traditionally used method for fibrinogen determination is the Clauss assay. It is clinically recommended as being the most reliable and commonly used in hospital practice. This test measures the rate of formation of a fibrin clot in plasma by the action of thrombin on fibrinogen, compared to a normal plasma control. The test is performed by adding a standard amount of exogenous thrombin to a platelet poor plasma and measuring the time for a clot to form. It has been used in the diagnosis of disseminated intravascular coagulation and liver disease and is generally performed in the central laboratory.

The test platforms were coated with 10 μL of a purified bovine thrombin (Biofact) at 25 U/mL supplemented with 0.1% (v/v) Triton X-100. Plasma samples with elevated fibrinogen concentrations were prepared by supplementing control plasma with purified fibrinogen (Sigma) to obtain final concentrations of approximately 5, 7, 9 and 11 g/L of fibrinogen assuming that control plasma contained 3 g/L of fibrinogen. 15 μL of normal and plasma samples with elevated fibrinogen concentrations were applied to the test chips and the relationship between fibrinogen concentration and the distance travelled was monitored (FIG. 27).

Figure 27:
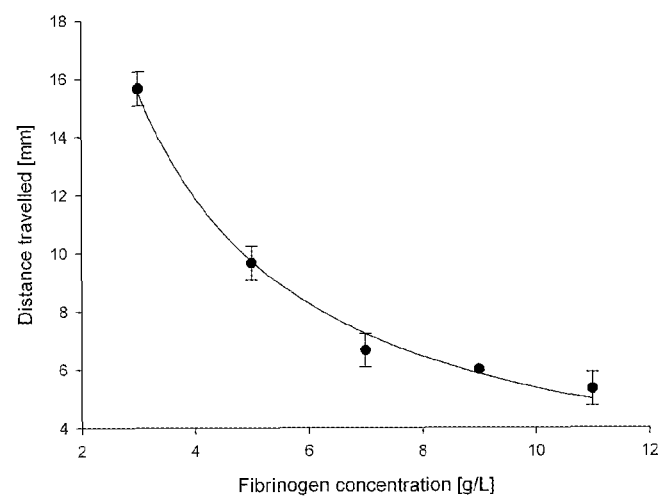
FIG. 27 shows the correlation between plasma fibrinogen content and the distance travelled in a thrombin-coated chip (n=3). y=1.0236+(43.5151/x), $R^2$=0.9966.

FIG. 27 shows the correlation between plasma fibrinogen content and the distance travelled in thrombin-coated chips (n=3). y=1.0236+(43.5151/x), $R^2$=0.9966.

The fibrinogen concentration was inversely proportional to the distance travelled on the thrombin-coated chips. The amount of thrombin and its activity remained constant at all times, and therefore, the fibrinogen content was the determinant of the distance travelled. An increased fibrinogen concentration in a sample resulted in rapid clot formation, which could be observed as a cloudy gel-like formation captured at the early stages of a channel. This strong fibrin mesh captured the content of the sample and ceased the flow. Normal and slightly elevated fibrinogen content samples formed weak, barely visible fibrin mesh, which was not strong enough to rapidly arrest the flow (data not shown). The flow was ceased at 15.7 mm for normal control plasma and at 9.7 mm for 5 g/mL. These two samples could be easily distinguished on a basis of a difference in a distance travelled. However, the difference in the distances travelled by higher fibrinogen content samples (7-11 g/mL) was not that remarkable; these reached between 5.3 and 6.7 mm. Despite the high concentration present on the surface, thrombin still requires at least six seconds to exert its full activity, according to the manufacturer. Within this time period, samples containing high fibrinogen concentrations will still be in their liquid form and will thus be able to travel some distance before being converted into a clot and was prevented from further movement. Additional factors affecting the flow properties of the system are the pushing force originating from the 15 μL sample which is initially deposited and the pulling capillary forces generated by the micropillar array. Such factors might result in difficulty differentiating between samples at very high fibrinogen levels. Nevertheless, abnormal levels of fibrinogen (above 4 g/L) could be easily discerned. The assay exhibited good precision with the highest variation detectable being ±1 mm (±3.7%). Plasma samples with normal fibrinogen levels only travelled approx. 16 mm out of the possible 27 mm. Therefore, there would be still room for the detection of fibrinogen-deficient samples, which is also important for clinical diagnosis of several pathological situations.

The use of purified thrombin to directly induce a clot formation and subsequent viscosity change was utilised in the following clotting monitoring assay development.

iii) Development of a Lateral Flow Assay for Fibrinogen Determination

The principle of an exogenous thrombin-based reagent to induce rapid clot formation and the resulting change in the resistance of the sample to flow was demonstrated to be suitable for measuring elevated levels of fibrinogen in spiked plasma samples. Further development of a lateral flow assay for fibrinogen determination would require the establishment of an assay which would result in the cessation of sample flow within the distance range defined by the chip corresponding to a range of clinically relevant fibrinogen concentrations with appropriate levels of precision, accuracy and correlation with laboratory standards, preferably in whole blood and plasma.

Optimisation of Reagent Chemistry Formulation

In general terms, the fibrinogen determination assay was based on the same principle as the Clauss method where, plasma is clotted with an excess of thrombin, to ensure that clotting times (CTs) are not limited by the endogenous thrombin concentration and that the fibrinogen level is inversely proportional to the time needed for the coagulum to appear (CT). The Clauss method varies greatly due to the source and composition of reagents. The appropriate concentration of thrombin dried onto the test platforms had to be established for both plasma and whole blood. Thrombin concentrations assuring rapid clotting with no interruption to the flow characteristics due to the properties of the protein surface coating had to be determined. Due to the presence of red blood cells and the resulting increased viscosity of whole blood in comparison to plasma sample movement was generally slower in whole blood and therefore, lower thrombin concentrations were used to accommodate greater sample movement. Aliquots of 15 µL normal citrated plasma and citrated plasma supplemented with 5 g/L of fibrinogen and normal whole blood samples were tested in channels coated with 10 µL of 25-100 U/mL or 0-25 U/mL of thrombin, for plasma and whole blood tests, respectively. The flow characteristics could be also manipulated by sample dilution, which would bring about the change in the sample viscosity and the concentration of the available fibrinogen. This approach was also studied (Table 2). In the case of plasma, the highest concentration of deposited thrombin (100 U/mL, which equated to 1 Upper strip) resulted in immediate clot formation in the sample application zone (FIG. 35. A dense fibrin mesh rapidly captured the entire sample within a clot and prevented any fluid movement. This was the case for samples with both normal and elevated fibrinogen levels. A two-fold dilution of the samples with water allowed the filling of the 100 U/mL coated channel with a difference of 7.4 mm between the distances travelled for normal and elevated (5 g/L fibrinogen supplemented) samples. Fibrin fibre mesh formed from the diluted samples was not capable of a rapid flow cessation, as it happened in the case of non-diluted samples and as a result the diluted samples travelled longer distances. Sample dilution would be an additional pre-analytical step. However, the decrease in thrombin concentration did cause a delay in clot formation and allowed the test sample to travel further before stopping. Ideally, a normal sample should travel a distance of approximately 12-20 mm to allow for the detection of samples with high fibrinogen levels with which flow would be stopped within the first few mm of the channel (expected distance traversed between 0-11 mm) and low fibrinogen levels (21-27 mm). The difference in the distance travelled by the normal versus the fibrinogen-supplemented plasma was around 7 mm for both 25 and 50 U/mL of dried thrombin.

However, the distance travelled by the normal sample was 10 mm at 50 U/mL and 15 mm for 25 U/mL. This latter configuration leaves a larger window for the measurement of high fibrinogen levels. In addition, the immobilisation of thrombin at 25 U/mL on the chip surface yielded better quality of flow. From these studies it was determined that the optimal assay conditions were for chips coated with 10 µL of 25 U/mL dried thrombin for the measurement of fibrinogen in plasma samples.

Table 2 below shows the effect of thrombin concentration on the distance travelled by normal and fibrinogen-supplemented (with 5 g/L) plasma and normal whole blood. Chips containing 25-100 U/mL or 0-25 U/mL thrombin solution were used to test plasma and whole blood, respectively (n=3). Plasma was tested undiluted and diluted 1:1 in water.

| Thrombin concentration [U/mL] | Distance travelled [mm] | | | | |
|---|---|---|---|---|---|
| | Plasma | | Plasma:H$_2$O (1:1) | | |
| | Normal | Supplemented | Normal | Supplemented | Whole blood |
| 0 | — | — | — | — | 16.3 ± 0.6 |
| 5 | — | — | — | — | 9.0 ± 0.0 |
| 10 | — | — | — | — | 6.3 ± 0.6 |
| 25 | 15.0 ± 0.0 | 8.0 ± 0.0 | 22.7 ± 0.6 | 19.3 ± 0.6 | 4.7 ± 0.6 |
| 50 | 10.0 ± 0.0 | 3.3 ± 1.5 | 20.7 ± 0.6 | 13.3 ± 0.6 | — |
| 100 | 0.0 ± 0.0 | 0.0 ± 0.0 | 15.7 ± 1.2 | 8.3 ± 0.6 | — |

Figure 35:
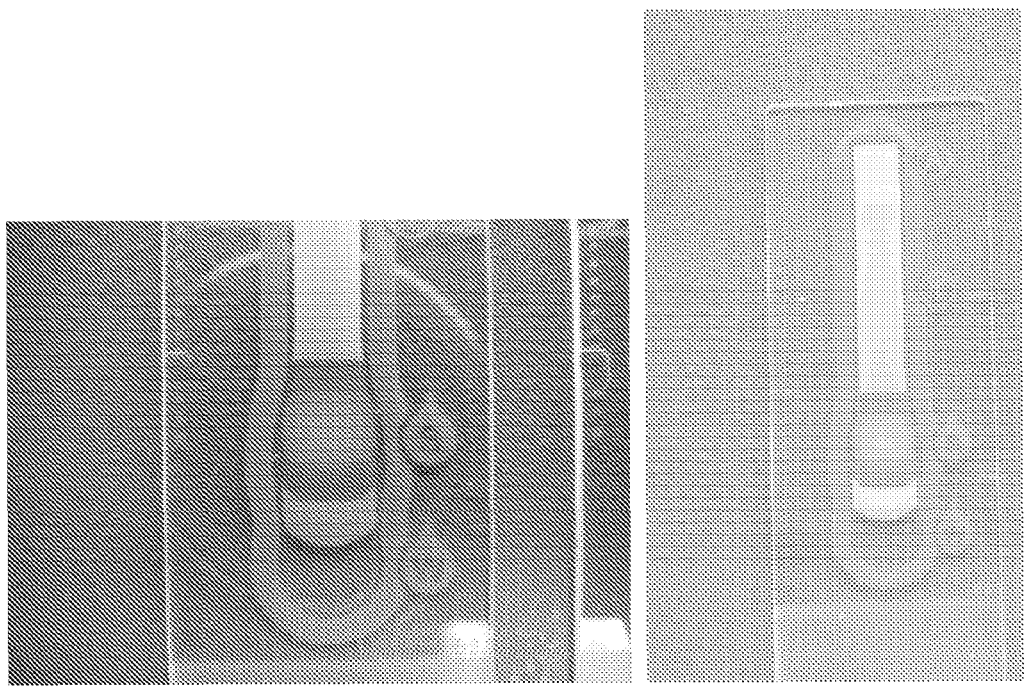
FIG. 35 is an image of the flow arrestment occurring as a result of the plasma clot formation induced by 100 U/mL of thrombin immobilised on the surface (10 µL).

FIG. 35 shows an image of the flow arrestment occurring as a result of the plasma clot formation induced by 100 U/mL of thrombin immobilised on the surface (10 µL).

The distances travelled by whole blood in channels coated with the formulation optimised for plasma appeared to be much shorter than for plasma. A normal whole blood sample travelled only 4.7 mm in comparison to approx. 15 mm for the normal plasma sample in a channel containing 25 U/mL of thrombin. To compensate for this, the concentration of thrombin was decreased in order to achieve a longer travel distance for whole blood control samples. Table 2 shows the values obtained from the measurement of normal whole blood on platforms coated with thrombin at 0, 5, and 25 U/mL. Due to the increased viscosity of whole blood in comparison to plasma, the distance travelled by normal, citrated whole blood in the channel with no thrombin (no clotting) was only 16.3 mm. Therefore, a concentration of 5 U/mL (9 mm for normal whole blood sample) was taken as being optimal for whole blood testing.

Standardisation of Thrombin Activity

The enzymatic activity of thrombin can vary according to source, batch or even within the same lot. Moreover, it can be influenced by several factors, including storage time and conditions. Deposition of a constant thrombin activity had to be maintained in order to obtain satisfactory reproducibility and to be able to reliably measure fibrinogen content. Therefore, it was necessary to develop a method that would allow quick measurement of thrombin activity. The activity of thrombin (Hyphen BioMed) used for the assay calibration was 100 U/mL after reconstitution, as claimed by the manufacturer and this was adopted as the standard. The normal control plasma CTs were 35±1 s and 19±1 s for 10 and 20 U/mL of thrombin, respectively, measured using the tilting tube test under ideal conditions of fresh reagent. The activity test could then be performed with any thrombin solution of unknown activity. Once these CT values were obtained, accordingly, the solutions of 25 and 5 U/mL (optimum for fibrinogen measurement in plasma and whole blood, respectively) could be prepared and deposited onto test chips. (Note: those CTs and thrombin activity values were only used for the purpose of assay chemistry standardisation. The thrombin concentrations stated above did not necessarily correlate with literature thrombin activity values or corresponding plasma CTs). As the exact enzymatic activity was unknown, the achievement of a CT of 35 s or 19 s was a way of normalising the thrombin solutions and were here then assumed to equate to 10 and 20 U/mL. An alternative method was to measure the normal plasma distance travelled in a channel coated with thrombin of unknown activity and compare to one with known activity. The thrombin concentration that yielded an identical distance travelled to that of a normal sample (shown in a calibration curve), could be used. Both methods of thrombin activity standardisation were shown to be viable. The first, "gold standard" tilting tube thrombin time measurement was especially useful where there was no limitation on the volume of normal control plasma (at least 300 μL of plasma per measurement). The method was quick and the thrombin concentration could be found within a few minutes. The second method used the actual fibrinogen determination assay system. This required only 15 μL of plasma sample per test. However, reference to the calibration curve and at least a few hours were necessary for preparation of the dried-chemistry test strips. In the following work, the thrombin activity was measured using the tilting tube test and then verified with an estimation of the distance travelled by normal control plasma in a channel coated with a fixed thrombin concentration.

Plasma and Whole Blood Assay Calibration

Figure 28:
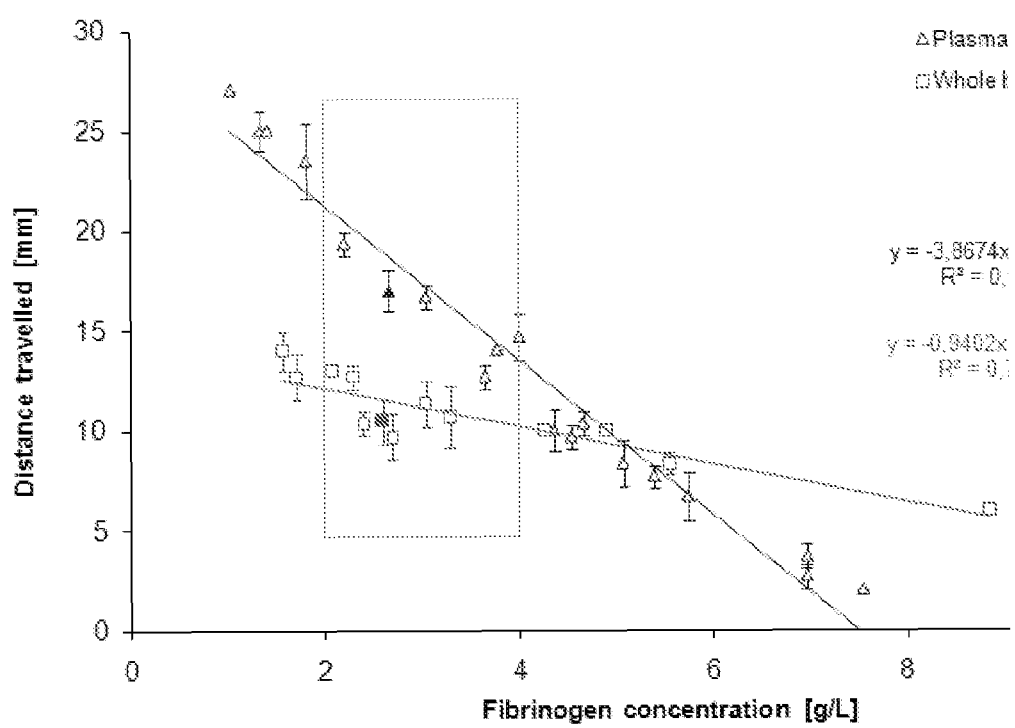
FIG. 28. Calibration curves generated using plasma (triangles) and whole blood (squares) samples containing a range of fibrinogen concentrations between 1.03-7.55 g/L and 1.56-8.86 g/L for plasma and whole blood, respectively (n=3). The linear correlation between the sample fibrinogen content and the distance traversed on the thrombin-coated assay chips was found to be y=−3.8674x+28.967 and y=−0.9402x+13.971 for plasma and whole blood, respectively with $R^2$=0.965 for plasma and $R^2$=0.797 for whole blood. The filled symbols indicate normal calibration samples, while the empty symbols were samples which were depleted or supplemented with fibrinogen. The box indicates the normal fibrinogen range in humans from 2-4 g/L.

An assay calibration was performed using plasma and whole blood samples containing a broad range of fibrinogen levels. In order to obtain elevated fibrinogen samples, control plasma and normal whole blood obtained from a healthy individual were supplemented with lyophilised fibrinogen. Low fibrinogen content control plasma was purchased from Hemosil, while low fibrinogen content whole blood was prepared by centrifugation and partial or total replacing of a plasma part with an equal volume of the low fibrinogen content control plasma from Hemosil. Exact fibrinogen content was determined using a routine hospital method based on the Clauss assay, the ACLtop® coagulation system (Instrumentation Laboratory) and Fibrinogen-C reagent (Hemosil). Tables 3 and 4 illustrate the distances travelled by plasma and whole blood samples, respectively with low, normal and elevated levels of fibrinogen. Separate calibration curves were generated on the basis of 19 plasma and 13 whole blood samples tested on platforms modified with 10 μL of 25 and 5 U/mL of thrombin, respectively (FIG. 28).

Table 3 below shows the distances travelled by plasma samples with a range of fibrinogen concentrations on chips coated with 25 U/mL thrombin reagent (n=3). Fibrinogen concentration determined by routine hospital method (ACLTop®, Instrumentation Laboratory) with Hemosil Fibrinogen-C reagent.

| Fibrinogen conc. [g/L] | Distance travelled [mm] | SD | RSD % |
|---|---|---|---|
| 1.03 | 27.0 | 0.0 | 0 |
| 1.34 | 25.0 | 1.0 | 4.0 |
| 1.41 | 25.0 | 0.0 | 0.0 |
| 1.81 | 23.5 | 1.9 | 8.1 |
| 2.2 | 19.3 | 0.6 | 3.0 |
| 2.66 | 17.0 | 1.0 | 5.9 |
| 3.04 | 16.7 | 0.6 | 3.5 |
| 3.65 | 12.7 | 0.6 | 4.6 |
| 3.77 | 14.0 | 0.0 | 0.0 |
| 4 | 14.7 | 1.2 | 7.9 |
| 4.36 | 10.0 | 1.0 | 10.0 |
| 4.54 | 9.7 | 0.6 | 6.0 |
| 4.66 | 10.3 | 0.6 | 5.6 |
| 5.07 | 8.3 | 1.2 | 13.9 |
| 5.39 | 7.7 | 0.6 | 7.5 |
| 5.74 | 6.7 | 1.2 | 17.3 |
| 6.97 | 3.7 | 0.6 | 15.7 |
| 6.97 | 2.7 | 0.6 | 21.7 |
| 7.55 | 2.0 | 0.0 | 0.0 |

Table 4 below shows the distances travelled by whole blood samples with a range of fibrinogen concentrations on chips coated with 5 U/mL thrombin reagent (n=3). Fibrinogen concentration determined by routine hospital method (ACLTop®, Instrumentation Laboratory) with Hemosil Fibrinogen-C reagent.

| Fibrinogen conc. [g/L] | Distance travelled [mm] | SD | RSD % |
|---|---|---|---|
| 1.56 | 14.0 | 1.0 | 7.1 |
| 1.7 | 12.7 | 1.2 | 9.1 |
| 2.07 | 13.0 | 0.0 | 0.0 |
| 2.29 | 12.7 | 0.6 | 4.6 |
| 2.4 | 10.3 | 0.6 | 5.6 |
| 2.6 | 10.4 | 1.1 | 10.9 |
| 2.7 | 9.7 | 1.2 | 11.9 |
| 3.04 | 11.3 | 1.2 | 10.2 |
| 3.29 | 10.7 | 1.5 | 14.3 |
| 4.27 | 10.0 | 0.0 | 0.0 |
| 4.9 | 10.0 | 0.0 | 0.0 |
| 5.55 | 8.3 | 0.6 | 6.9 |
| 8.86 | 6.0 | 0.0 | 0.0 |

FIG. 28 is a calibration curves generated using plasma (triangles) and whole blood (squares) samples containing a range of fibrinogen concentrations between 1.03-7.55 g/L and 1.56-8.86 g/L for plasma and whole blood, respectively (n=3). The linear correlation between the sample fibrinogen content and the distance traversed on the thrombin-coated assay chips was found to be y=−3.8674x+28.967 and y=−0.9402x+13.971 for plasma and whole blood, respectively with $R^2$=0.965 for plasma and $R^2$=0.797 for whole blood. The filled symbols indicate normal calibration samples, while the empty symbols were samples which were depleted or supplemented with fibrinogen. The box indicates the normal fibrinogen range in humans from 2-4 g/L.

From the calibration curves obtained, it would suggest that the fibrinogen concentration in plasma and whole blood appeared to be the major factor dictating the distances travelled by the samples on the thrombin-coated chips. The correlation for plasma samples of 0.97 was significantly better than that for whole blood being 0.80. However, spiked and depleted control plasmas possess a homogeneity not present in the natural population and testing would be required on a range of real patient plasma samples to ensure the validity of the method. The assay sensitivity and descrimination between concentrations of fibrinogen were also better for plasma than for whole blood. Nonetheless, the assay showed excellent potential as both a plasma and whole blood assay, the latter which would significantly simplify any potential clinical test. This assay demonstrated itself to be a valid method for the determination of plasma fibrinogen content between approx. 1-7 g/L. Fibrinogen concentrations lower than 2 g/L and higher than 4 g/L are considered as abnormal. Therefore, the distance travelled above 21.2 mm and below 13.5 mm has to be considered as an indication of a declined or elevated fibrinogen level, respectively.

Analysis of Patient Samples

Figure 29:
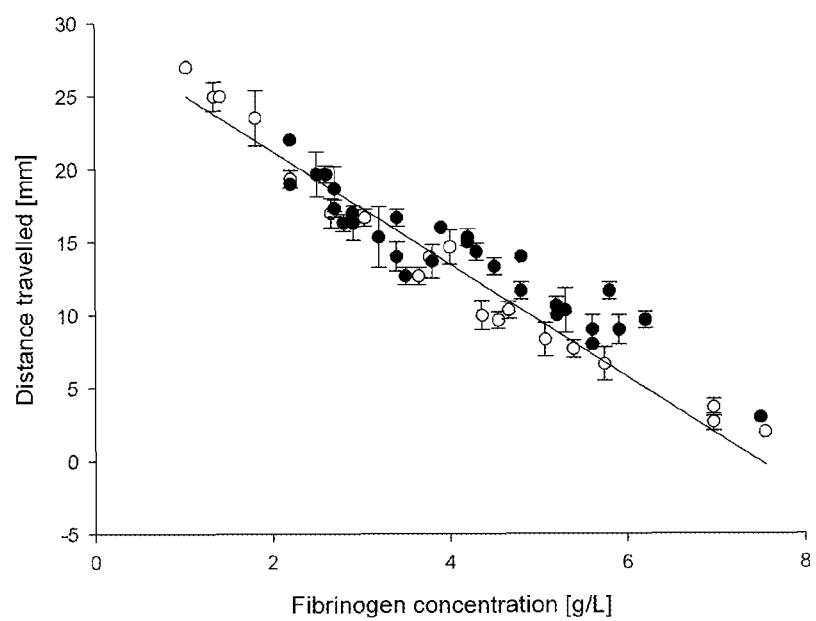
FIG. 29 shows the results of the determination of fibrinogen content in patient plasma samples using the lateral flow assay device. Distance traversed was plotted against the concentration of fibrinogen obtained from routine laboratory measurement. Patient samples (filled symbols) (n=3) are shown to follow the trend of the calibration samples.

It was shown above that the lateral flow assay based on a chip with a dried thrombin-based reagent chemistry was a viable method for the determination of a fibrinogen concentration in control plasma and whole blood samples. To further validate the assay, patient samples containing a wide range of fibrinogen concentrations were tested on the optimised assay platform in parallel with the routine hospital laboratory method described above. Table 5 summarises the fibrinogen concentrations for 31 patient samples determined by ACLtop®, the distances travelled in the developed system and the derived fibrinogen values based on the calibration curve established above. Since the exact fibrinogen content of those samples was known, it was possible to directly correlate it to the distance travelled and estimate the accuracy of the fibrinogen measurement using the developed technique (FIG. 29). Table 5 below shows the distance travelled in thrombin-coated chips was measured for 31 patient plasma samples with identified fibrinogen content (ACLtop®). Using calibration curve equation and the distance travelled, fibrinogen concentrations were re-calculated (n=3). The sample with the value in italics (9.3 g/L fibrinogen) gave an erroneous result.

| Fibrinogen conc. [g/L] by reference method | Distance travelled [mm] | SD | CV [%] | Fibrinogen conc. [g/L] by developed method | SD | CV [%] |
|---|---|---|---|---|---|---|
| 2.2 | 19.0 | 0.0 | 0.0 | 2.6 | 0.0 | 0.0 |
| 2.2 | 22.0 | 0.0 | 0.0 | 1.8 | 0.0 | 0.0 |
| 2.5 | 19.7 | 1.5 | 7.8 | 2.4 | 0.4 | 16.4 |
| 2.6 | 19.7 | 0.6 | 2.9 | 2.4 | 0.1 | 6.2 |
| 2.7 | 17.3 | 0.6 | 3.3 | 3.0 | 0.1 | 5.0 |
| 2.7 | 18.7 | 1.5 | 8.2 | 2.7 | 0.4 | 14.8 |
| 2.8 | 16.3 | 0.6 | 3.5 | 3.3 | 0.1 | 4.6 |
| 2.9 | 17.0 | 0.0 | 0.0 | 3.1 | 0.0 | 0.0 |
| 2.9 | 16.3 | 1.2 | 7.1 | 3.3 | 0.3 | 9.1 |
| 3.2 | 15.3 | 2.1 | 13.6 | 3.5 | 0.5 | 15.3 |
| 3.4 | 14.0 | 1.0 | 7.1 | 3.9 | 0.3 | 6.7 |
| 3.4 | 16.7 | 0.6 | 3.5 | 3.2 | 0.1 | 4.7 |
| 3.5 | 12.7 | 0.6 | 4.6 | 4.2 | 0.1 | 3.5 |
| 3.8 | 13.7 | 1.2 | 8.4 | 4.0 | 0.3 | 7.5 |
| 3.9 | 16.0 | 0.0 | 0.0 | 3.4 | 0.0 | 0.0 |
| 4.2 | 15.0 | 0.0 | 0.0 | 3.6 | 0.0 | 0.0 |
| 4.2 | 15.3 | 0.6 | 3.8 | 3.5 | 0.1 | 4.2 |
| 4.3 | 14.3 | 0.6 | 4.0 | 3.8 | 0.1 | 3.9 |
| 4.5 | 13.3 | 0.6 | 4.3 | 4.0 | 0.1 | 3.7 |
| 4.8 | 11.7 | 0.6 | 4.9 | 3.9 | 0.0 | 0.0 |
| 4.8 | 14.0 | 0.0 | 0.0 | 4.5 | 0.1 | 3.3 |
| 5.2 | 10.0 | 0.0 | 0.0 | 4.9 | 0.0 | 0.0 |
| 5.2 | 10.7 | 0.6 | 5.4 | 4.7 | 0.1 | 3.2 |
| 5.3 | 10.3 | 1.5 | 14.8 | 4.8 | 0.4 | 8.2 |
| 5.6 | 9.0 | 1.0 | 11.1 | 5.2 | 0.3 | 5.0 |
| 5.6 | 8.0 | 0.0 | 0.0 | 5.4 | 0.0 | 0.0 |
| 5.8 | 11.7 | 0.6 | 4.9 | 4.5 | 0.1 | 3.3 |
| 5.9 | 9.0 | 1.0 | 11.1 | 5.2 | 0.3 | 5.0 |
| 6.2 | 9.7 | 0.6 | 6.0 | 5.0 | 0.1 | 3.0 |
| 7.5 | 3.0 | 0.0 | 0.0 | 6.7 | 0.0 | 0.0 |
| *9.3* | *6.3* | *0.6* | *9.1* | *5.9* | *0.1* | *2.6* |

FIG. 29 shows the results of the determination of fibrinogen content in patient plasma samples using the lateral flow assay device (filled circles) (n=3). Distance traversed was plotted against the concentration of fibrinogen obtained from the routine laboratory method (ACLtop®). The results shown are combined with the calibration data generated in FIG. 28 above (empty circles) (y=−3.8674x+28.967). Patient samples are shown to follow the trend of the calibration samples with an equation: y=−2.8569x+25.768.

Patient samples (y=−2.8569x+25.768) followed a similar trend to that of the calibration curve (y=−3.8674x+28.967) with relatively low variability ($R^2$=0.89). Testing of the real patient samples introduced only minor variability in comparison to the uniform control calibration samples where an excellent correlation was obtained ($R^2$=0.97). For most tested samples, the deviation in the distance travelled was acceptably low (±1 mm). The maximum CV was 14.8%, but for the majority of tests was below 5%. From the rate of thrombin action on fibrinogen which dictates the distance travelled, the fibrinogen concentration could be readily deduced. Fibrinogen content was calculated on the basis of the distance travelled, using the following calibration curve equation; y=−3.8674x+28.967 and related to the values obtained from the routine hospital method in ACLtop®. Fibrinogen concentrations determined by both methods were correlated in FIGS. 30 and 31.

Figure 30:
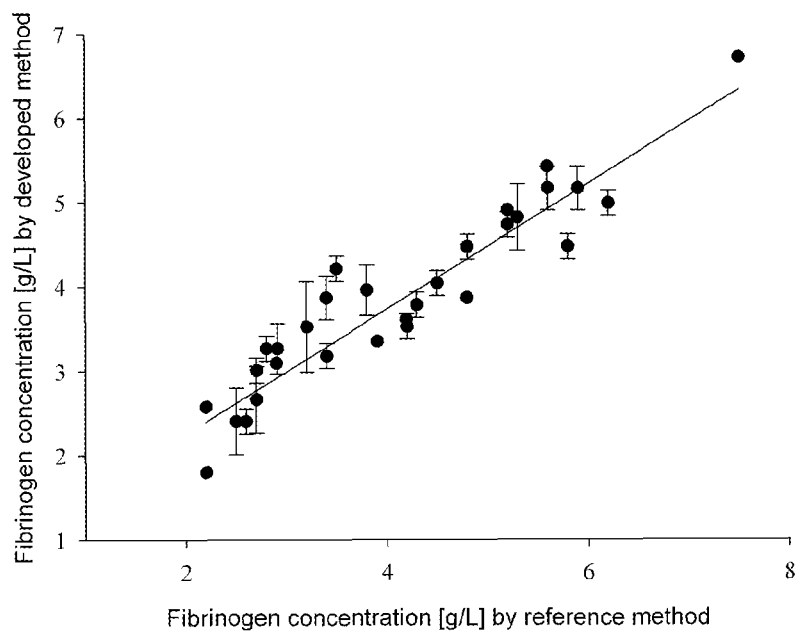
FIG. 30 shows the correlation of fibrinogen determination by reference method with fibrinogen determination by the developed lateral flow method (n=3). The correlation was y=0.7387x+0.8271 with a correlation coefficient of 0.89.

FIG. 30 shows the correlation of fibrinogen determination by reference method (ACLtop®) with fibrinogen determination by the developed lateral flow method (n=3). The correlation was y=0.7387x+0.8271 with a correlation coefficient of 0.89.

Figure 31:
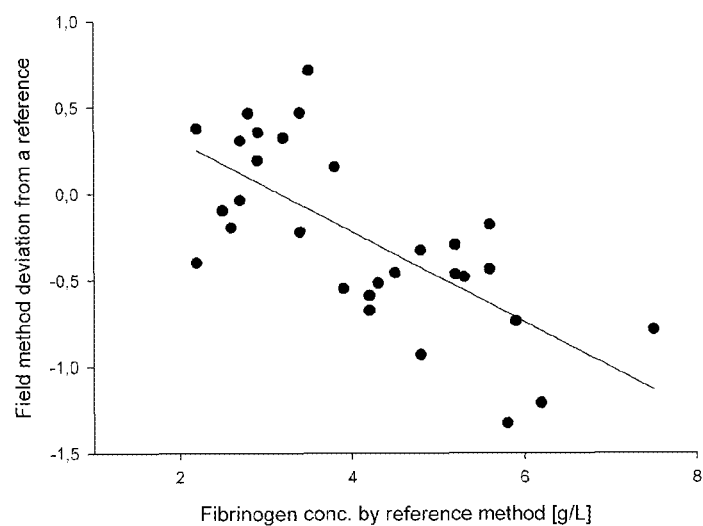
FIG. 31 is a Bland-Altman plot (*Ref. Bland,* J. M.; Altman, D. G. Lancet 1986, 1, 307-310). illustrating increased disparity between the fibrinogen concentrations obtained with the developed assay and the routine method as the fibrinogen level increased (field method deviation from a reference method). Values close to zero were in agreement with the reference values. The trend line shows that with higher fibrinogen concentration the accuracy of measurement was decreasing. The slope value was −0.2613.

FIG. 31 is a Bland-Altman plot (Bland 1986) illustrating increased disparity between the fibrinogen concentrations obtained with the developed assay and the routine method (ACLtop®) as the fibrinogen level increased (field method deviation from reference method). Values close to zero were in agreement with the reference values. The trend line shows that with higher fibrinogen concentration the accuracy of measurement was decreasing. The slope value was −0.2613.

Correlation between the fibrinogen values derived by the developed method and the reference method (ACLtop®) was found to be 0.89 (FIG. 30). However, the slope was 0.74 and the offset 0.82 showing that the developed method overestimates fibrinogen concentration for reference values below approx. 3 g/L and underestimated fibrinogen concentration at higher values compared to the reference method. Further analysis using Bland-Altman plots (FIG. 31), also shows that the deviation from the reference method increased at higher fibrinogen levels. Elevated fibrinogen concentrations resulted in the shortest distances travelled. The additional variability in the detection of these levels could be caused by the inherent variability introduced by the very short reaction time (manufacturer recommendation suggests at least 6 s reaction time be allowed between the thrombin and the sample) and the short distance measurement with an associated error of approximately ±0.25 mm. Further optimisation of the chip design could improve the test precision for the detection of highly elevated fibrinogen levels. Current laboratory tests typically test in the ranges of 0.035-10 g/L.

Figure 32:
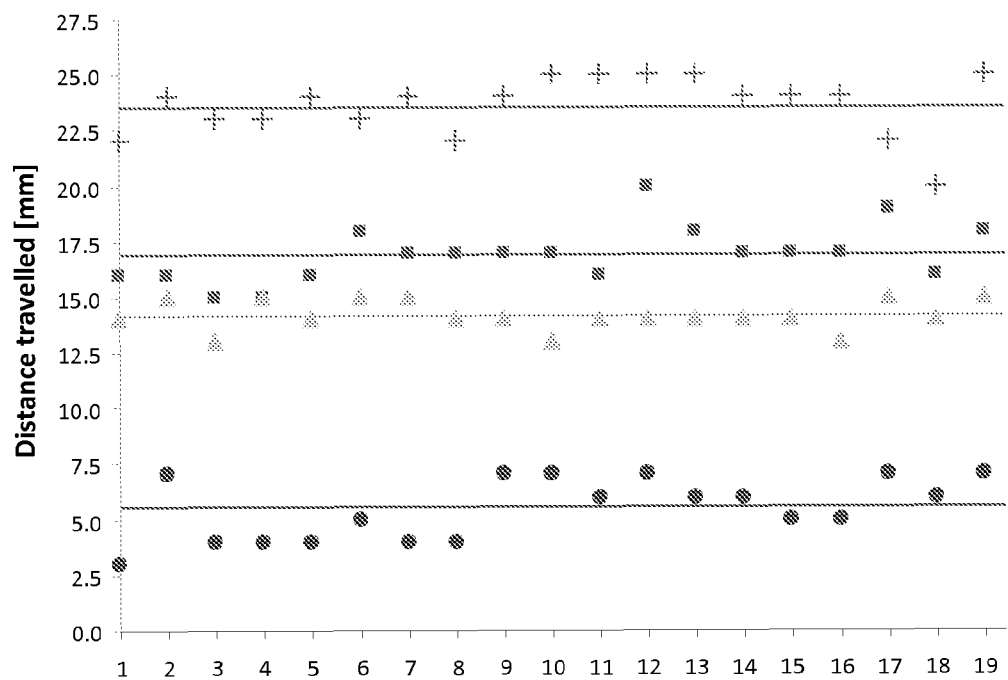
FIG. 32 shows repeats of plasma samples with low 1.4 g/L (crosses), normal 3.1 g/L (squares), elevated 3.8 g/L (triangles) and significantly elevated 6.0 g/L (circles) fibrinogen concentrations. The distances travelled for all repeats are shown. Horizontal lines indicate the average distances travelled.

An assay precision study was conducted by repeated testing (n=20) of plasma samples with low (1.4), normal (3.1), elevated (3.8) and significantly elevated (6.0 g/L) fibrinogen content (FIG. 32). The variation was relatively low for samples with normal, low and elevated fibrinogen content with CVs of less than 10%. The CV for highly elevated samples was higher (24.4%) which indicated a moderate decrease in the assay precision with increased fibrinogen concentrations. However, the variability between particular repeats of this sample was not dramatic. The distance travelled was between 3-7 mm. The detection of plasma or blood components in a patient sample is always associated with significant variability due to variations in haemodilution and many other factors. Hence, the variability exhibited here was acceptable. Strongly elevated fibrinogen level, with some variability, could still be measured. For clinical use the need for precision is higher for low concentrations as here, a decrease of 0.5 g/L could trigger the requirement for transfusion in the operating theatre or intensive care. However, a change of even 2 g/L at the high end would most likely not change the treatment and is more an issue of long term management. Thus the assay can be considered appropriate for both elevated and reduced fibrinogen level detection. Due to its speed, simplicity and performance, the format of the assay is suitable for point-of-care settings from the ambulance to the emergency room operating theatre or doctor's surgery.

FIG. 32 shows repeats of plasma samples with low 1.4 g/L (crosses), normal 3.1 g/L (squares), elevated 3.8 g/L (triangles) and significantly elevated 6.0 g/L (circles) fibrinogen concentrations. The distances travelled for all repeats are shown. Horizontal lines indicate the average distances travelled.

Device Stability

Figure 33:
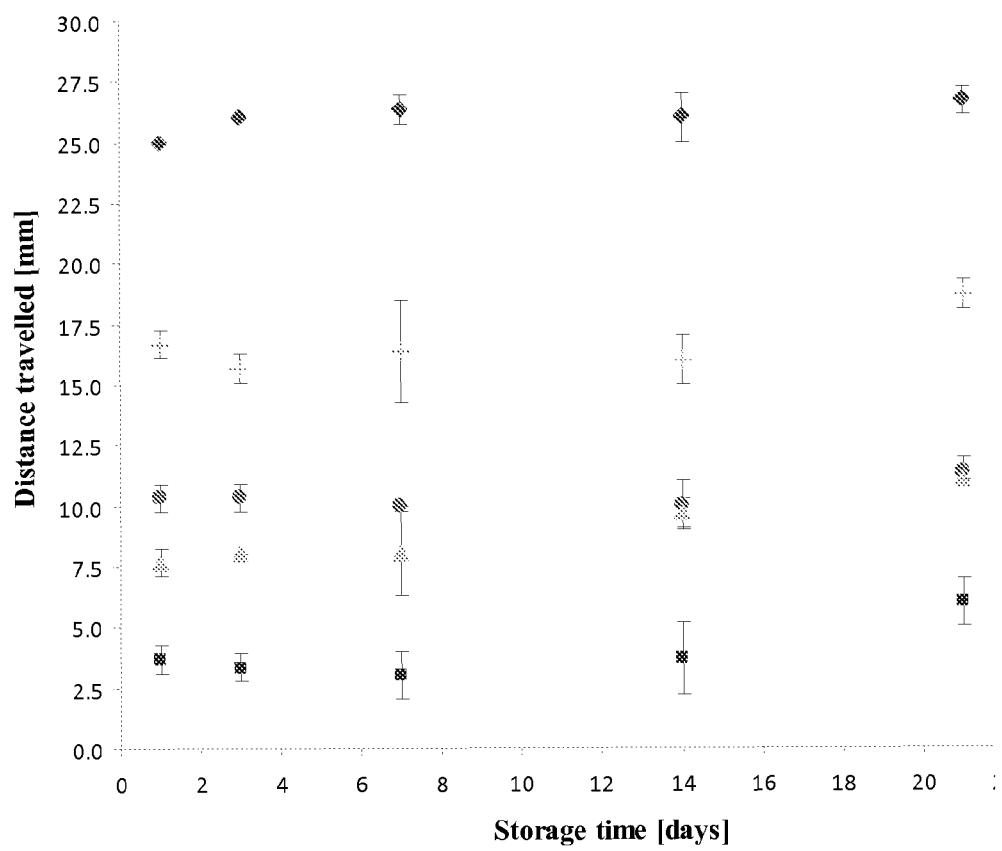
FIG. 33 shows the results of a storage stability study of thrombin-coated chips and their response in the fibrinogen assay device: 1.41 g/L (diamonds), normal: 3.04 g/L (crosses) and elevated: 4.66 (circles), 5.39 (triangles) and 6.97 g/L (squares) fibrinogen level (n=3).

Platforms coated with the optimised thrombin-based reagent were stored at 4° C. for a period of up to 21 days. The distance travelled by plasma samples with different fibrinogen concentrations was measured on days 1, 3, 7, 14 and 21 (FIG. 33). There was no significant differences in the distance travelled (25-27 mm) by a sample with abnormally low fibrinogen concentration (1.41 g/L), which was insignificantly higher than the expected distance travelled, 23.5 mm, calculated using the calibration curve equation: $y=-3.8674x+28.967$. The obtained distance travelled allowed recognition of declined fibrinogen level. Normal fibrinogen content sample (3.04 g/L) travelled 15.7-16.7 mm in the first 2 weeks and 18.7 mm on the 3 week old platform. Using the calibration curve equation could be deduced that a sample that travelled 15.7-16.7 mm contains 3.2-3.4 g/L of fibrinogen, which was within the normal range expected for normal plasma control, while 18.7 mm would be an indicator of decreased fibrinogen level, 2.6 g/L (calculated on the basis of the calibration curve). This suggests that the 21 day old platforms could not be used as this could introduce a false result. Three samples with marginally and significantly elevated fibrinogen content: 4.66, 5.39 and 6.97 g/L were also tested. The following distances travelled were obtained for these samples, respectively: 10.0-10.3 mm, 7.7-9.7 mm and 3.0-3.7 mm on 1-14 day old platforms and prolonged distances travelled on 21 day platforms: 11.3 mm, 11.0 mm and 6.0 mm. The results suggest that devices containing immobilised thrombin can be readily stored at 4° C. for a period of up to 14 days without any special treatment as there was little statistical difference in the distance travelled by samples throughout this period of storage. The thrombin enzymatic activity appeared to have declined slightly after 3 weeks of storage. In consequence the distances travelled were slightly increased for all tested samples. The use of chips stored for more than 2 weeks may result in an underestimation of the fibrinogen level. Therefore, chips older than 2 weeks were not used for testing. Special storage conditions i.e. decreased or controlled humidity, vacuum conditions or the addition of preservatives and/or lyophilisation of the thrombin immobilised in a chip could be easily employed in order to increase device stability.

FIG. 33 shows the results of a storage stability study of thrombin-coated chips and their response in the fibrinogen assay device: 1.41 g/L (diamonds), normal: 3.04 g/L (crosses) and elevated: 4.66 (circles), 5.39 (triangles) and 6.97 g/L (squares) fibrinogen level (n=3).

Conclusion from Example 5

An assay device was developed which was capable of measuring fibrinogen in whole blood and plasma at physiologically relevant levels. The device was based on a simple but reliable lateral flow principle with fibrinogen being determined by the distance travelled before cessation of flow as a result of clotting. The assay device possessed several advantages over traditional methods including the low sample volume required (15 μL), the absence of any pre-analytical steps including dilution or separation and the speed of the measurement with a result available within 5 min. The assay is a modification of the Clauss method which is mostly commonly used in laboratory practice and frequently referred as the most reliable method for clottable, active fibrinogen content determination. Both elevated and reduced levels of fibrinogen could be detected using the same test platform. The assay was capable of fibrinogen determination in the range from 1 to 7 g/L.

The invention claimed is:

1. A lateral capillary flow device for monitoring and/or measurement of coagulation in a liquid sample wherein the device is an open lateral flow device which comprises a non-porous substrate with a zone for receiving a sample and a defined flow path zone wherein a fibrinogen or thrombin clotting agent or a derivative thereof is deposited on at least part of the defined flow path zone to accelerate coagulation of the liquid sample, to enable formation of an evenly distributed clot along the defined flow path zone and to result in a change in flow rate or cessation of flow of the liquid sample along the defined flow path zone, wherein the surface area to volume ratio between the sample and defined flow path of the device is improved or increased such that the flow path zone comprises a planar surface with a plurality of regularly spaced projections which induce capillary action in the liquid sample along the defined flow path, wherein said regularly spaced projections extend along substantially the entire length of the flow path zone,
wherein the flow path zone of the substrate comprises a plurality of vertical projections or micropillars protruding from the surface of the substrate which define the flow path zone along the substrate, and
wherein the vertical projections consist of areas of projections substantially vertical to said surface, and having a height (H), diameter (D), and reciprocal spacing such that lateral capillary flow of the liquid sample in the flow path zone is achieved.

2. A lateral capillary flow device for monitoring and/or measurement of coagulation in a liquid sample wherein the device is an open lateral flow device which comprises a non-porous substrate with a zone for receiving a sample and a defined flow path zone wherein a fibrinogen or thrombin clotting agent or a derivative thereof is deposited on at least part of the defined flow path zone to accelerate coagulation of the liquid sample, to enable formation of an evenly distributed clot along the defined flow path zone and to result in a change in flow rate or cessation of flow of the liquid sample along the defined flow path zone, wherein the surface area to volume ratio between the sample and defined flow path of the device is improved or increased such that the flow path zone comprises a planar surface with a plurality of regularly spaced projections which induce capillary action in the liquid sample along the defined flow path, wherein said regularly spaced projections extend along substantially the entire length of the flow path zone wherein the clotting agent is deposited on the entire surface of the defined flow path zone.

3. A lateral capillary flow device for monitoring and/or measurement of coagulation in a liquid sample wherein the device is an open lateral flow device which comprises a non-porous substrate with a zone for receiving a sample and a defined flow path zone wherein a fibrinogen or thrombin clotting agent or a derivative thereof is deposited on at least part of the defined flow path zone to accelerate coagulation of the liquid sample, to enable formation of an evenly distributed clot along the defined flow path zone and to result in a change in flow rate or cessation of flow of the liquid sample along the defined flow path zone, wherein the surface area to volume ratio between the sample and defined flow path of the device is improved or increased such that the flow path zone comprises a planar surface with a plurality of regularly spaced projections which induce capillary action in the liquid sample along the defined flow path, wherein said regularly spaced projections extend along substantially the entire length of the flow path zone wherein the clotting agent also comprises a supporting reagent material selected from poly(ethylene glycol) (PEG), sugars, non-ionic surfactants, and combinations thereof.

4. The device according to claim 1 wherein blood coagulation is monitored and/or measured.

5. The device according to claim 1 wherein the substrate is a plastic material, preferably a thermoplastic material, more preferably a cyclic polyolefin, polystyrene, polyethylene terephthalate (polyester) (PET) or polymethylmethacrylate (PMMA).

6. The device according to claim 1 wherein the substrate is a silicon or glass substrate.

7. The device according to claim 1 comprising a coating of SiOx deposited on the surface of the substrate.

8. The device according to claim 1 wherein the surface of the substrate is modified with a polyelectrolyte.

9. The device according to claim 1 comprising an additional layer of one or more reagent materials.

10. The device according to claim 9 wherein the reagent material is selected from one or more of the following tissue factors, phospholipids, additional materials that can induce or/and accelerate coagulation including clotting factors and/or procoagulants, micronized silica materials including glass fibres, ground glass and glass microparticles, and/or coagulation surface activators including kaolin, celite, ellagic acid, and/or calcium chloride.

11. The device according to claim 1 wherein the substrate is a cyclic polyolefin substrate comprising micropillar projections extending vertically from one surface of the substrate wherein the cyclic polyolefin substrate comprises a layer of SiOx.

12. A method for monitoring and/or measuring clotting in a liquid sample using a lateral capillary flow device according claim 1 wherein the sample is added to the receiving zone on the substrate and is transported through capillary action from the receiving zone through a flow path such that lateral capillary flow of said liquid sample is achieved characterized in that prior to the addition of the sample, the clotting agent fibrinogen or thrombin is deposited on at least part of the surface of the defined flow path zone to accelerate the coagulation of the liquid sample, to form an evenly distributed clot along the flow path zone and to modify flow rate or stop the flow of the liquid sample along the defined flow path zone.

13. The method according to claim 12 wherein the clotting agent is deposited on the entire surface of the defined flow path zone.

14. The method according to claim 12 wherein the clotting agent also comprises a supporting reagent material, including poly(ethylene glycol) (PEG), sugars and/or non-ionic surfactants.

15. The method according to claim 12 wherein blood coagulation is monitored and/or measured.

16. The device according to claim 1 wherein the liquid sample is blood or plasma.

17. The device according to claim 1 suitable for the carrying out one of the following coagulation assays: activated clotting time [ACT], activated partial thromboplastin time [aPTT], prothrombin assay [PT]; thrombin clotting time (TCT); and/or fibrinogen assay.

18. The method according to claim 12 wherein prior to use the surface of the substrate is modified to increase surface activity and hydrophilicity to facilitate improved liquid fluid flow through the device comprising the steps of
depositing a coating of SiOx on the surface of the substrate; and/or modifying the surface of the substrate with a poly electrolyte.

19. The device according to claim 1 wherein the change in flow rate or cessation of flow of the liquid sample along the defined flow path zone is a cessation of flow.

20. The device according to claim 1 wherein the projections have a height in the interval of about 15 to about 150 μm, a diameter of about 10 to about 160 μm, and a distance between projections of about 5 to about 200μm.

21. The device according to claim 1 comprising a coating of SiOx on the surface of the substrate, and/or the surface of the substrate is modified with a poly electrolyte.

* * * * *